(12) United States Patent
Unkefer et al.

(10) Patent No.: US 8,865,451 B2
(45) Date of Patent: Oct. 21, 2014

(54) TRANSGENIC ALGAE ENGINEERED FOR HIGHER PERFORMANCE

(75) Inventors: Pat J. Unkefer, Los Alamos, NM (US); Penelope S. Anderson, Los Alamos, NM (US); Thomas J. Knight, Raymond, ME (US)

(73) Assignees: Los Alamos National Security, LLC, Los Alamos, NM (US); University of Maine System Board of Trustees, Bangor, ME (US)

(*) Notice: Subject to any disclaimer, the term of this patent is extended or adjusted under 35 U.S.C. 154(b) by 548 days.

(21) Appl. No.: 13/037,149

(22) Filed: Feb. 28, 2011

(65) Prior Publication Data

US 2011/0217780 A1    Sep. 8, 2011

Related U.S. Application Data

(60) Provisional application No. 61/308,974, filed on Feb. 28, 2010.

(51) Int. Cl.
| | | |
|---|---|---|
| *C12N 1/13* | (2006.01) | |
| *C12N 9/10* | (2006.01) | |
| *C07H 21/04* | (2006.01) | |
| *C12N 1/12* | (2006.01) | |
| *C12N 15/82* | (2006.01) | |
| *C12N 9/00* | (2006.01) | |

(52) U.S. Cl.
CPC .............. *C12N 1/12* (2013.01); *C12N 15/8261* (2013.01); *C12Y 603/01002* (2013.01); *C12N 9/1096* (2013.01); *C12Y 206/01064* (2013.01); *C12N 9/93* (2013.01)
USPC ...... 435/257.2; 435/193; 536/23.2; 536/23.6; 536/23.7

(58) Field of Classification Search
None
See application file for complete search history.

(56) References Cited

U.S. PATENT DOCUMENTS

| | | |
|---|---|---|
| 5,145,777 A | 9/1992 | Goodman et al. |
| 6,555,500 B1 * | 4/2003 | Martinez et al. .............. 504/138 |
| 6,831,040 B1 | 12/2004 | Unkefer et al. |
| 2009/0070897 A1 | 3/2009 | Goldman et al. |

OTHER PUBLICATIONS

Mosca et al 1994 FEBS Letters 353: p. 21-24.*
Chow and Tung 1998 Plant Cell Reports 18: p. 778-780.*
Akama et al 1992 Plant Cell Reports 12: p. 7-11.*
Sato et al 2000 Accession # Q9LVI8, Uniprot data base.*
UniProKB/TrEMBL. A8HQU6_CHLR. Dec. 4, 2007 (http://www.uniprot.org/uniprot/A8HQU6.txt?version=*), May 1, 2011.
International Search Report for PCT/US2011/26503 mailed Jun. 14, 2011.
International Preliminary Report on Patenatbility, Written Opinion of the International Searching Authority for PCT/US2011/26503 mailed Sep. 13, 2012.

* cited by examiner

*Primary Examiner* — Brent T Page
*Assistant Examiner* — Matthew Keogh
(74) *Attorney, Agent, or Firm* — Kilpatrick Townsend & Stockton LLP

(57) ABSTRACT

The present disclosure relates to transgenic algae having increased growth characteristics, and methods of increasing growth characteristics of algae. In particular, the disclosure relates to transgenic algae comprising a glutamine phenylpyruvate transaminase transgene and to transgenic algae comprising a glutamine phenylpyruvate transaminase transgene and a glutamine synthetase.

10 Claims, 1 Drawing Sheet

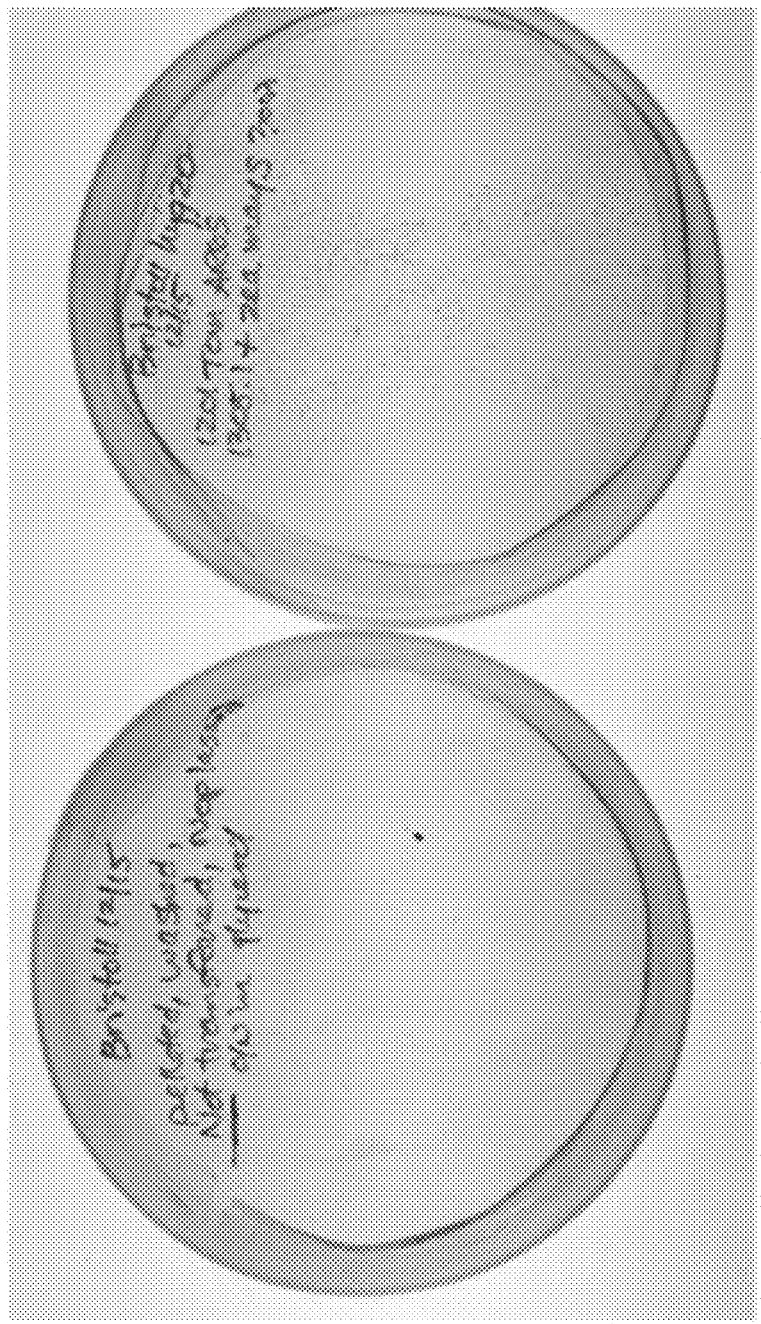

TRANSGENIC ALGAE ENGINEERED FOR HIGHER PERFORMANCE

CROSS REFERENCE TO RELATED APPLICATION

This application claims the benefit of U.S. Provisional Application No. 61/308,974, filed Feb. 28, 2010, which is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under Contract No. DE-AC52-06NA25396, awarded by the United States Department of Energy to Los Alamos National Security, LLC. The government has certain rights in this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 686522000500SEQLIST.txt, date recorded: Feb. 25, 2011, size: 132 KB).

FIELD

The present disclosure relates to transgenic algae having increased growth characteristics, and methods of increasing growth characteristics of algae. The disclosure also relates to recombinant polynucleotides for the generation of transgenic algae having increased growth characteristics.

BACKGROUND OF THE INVENTION

The global biodiesel market demand is estimated to reach 37 billion gallons by 2016, growing at an average annual growth rate of 42%. Europe will be the major market for the next decade or so, closely followed by the US market. To meet this increased market demand, additional oil sources, especially non-edible oils, need to be explored (Li et al., 2008 Appl. Microbiol. Biotechnol. 80:749-756). Microalgae seems to be the only source of renewable biodiesel that has the potential to displace petroleum-derived transportation fuels without the controversial argument "Food or Fuel" and to help the nation reach the 2003 Biofuels Directive target of achieving greenhouse gas savings (Christi, 2007, Biotechnol. Adv. 25:294-306; Christi, 2008, Trends Biotechnol. 26:126-131; Cockerill and Martin, 2008, Biotechnol. Biofuels 1:9).

The most advanced biotechnology being applied to algal growth has been the creation of the antennae mutants that have less light harvesting machinery in the cell, which allows a greater fraction of the light to pass through an individual cell. This light then strikes other cells deeper in the culture. This is viewed as advantageous because some of the light energy striking a normal cell is in excess and is lost as fluorescence. These mutants do not suffer this loss of excess energy; it is available to other deeper cells in the culture. Thus the overall culture accumulates biomass faster. These mutants then grow using their normal rates of metabolism. In addition, some are attempting to engineer herbicide resistance genes into the production strains to allow competing algae in a production bioreactor to be controlled with the herbicide.

Numerous algal biofuels companies populate the landscape; it is reasonable to expect at least 20 of them will be producing algal oil at large scale within a year. Microalgal biodiesel is technically feasible (Gouveia et al. 2009 J. Ind. Microbiol. Biotechnol 36:269-274). However technoeconomic analyses show that for microalgal biofuels to be economically competitive with petrodiesel, the production, harvesting and extraction steps must be optimized and costs reduced. The production step must be increased substantially to increase the overall total biomass production. The degree to which the production rate can be improved within the constraints of the fixed costs of the production reactor, will dictate how much other costs must be reduced to achieve profitability or even the bottom line. The technology described herein can be expected to address that need.

In plants, the organic compound 2-oxoglutaramate is a powerful signal metabolite which regulates the function of a large number of genes involved in the photosynthesis apparatus, carbon fixation and nitrogen metabolism. A number of transaminase and hydrolyase enzymes known to be involved in the synthesis of 2-hydroxy-5-oxoproline in animals have been identified in animal liver and kidney tissues (Cooper and Meister, 1977, CRC Critical Reviews in Biochemistry, pages 281-303; Meister, 1952, J. Biochem. 197:304). In algae, the biochemical synthesis of 2-hydroxy-5-oxoproline has not been established. Moreover, the function of 2-hydroxy-5-oxoproline in algae is unknown.

Unkefer et al., U.S. Pat. No. 6,593,275, disclose a dramatic increase in the growth rate of algae when treated with 2-hydroxy-5-oxoproline. Continuously culturing the algae in the presence of this compound or mixtures of this compound with other prolines will enrich sub-strains of the algae that respond well to the prolines.

SUMMARY OF THE INVENTION

The present disclosure relates to transgenic algae having increased growth characteristics. In one embodiment, the invention relates to transgenic algae having enhanced (faster) growth rates. Applicants have recently identified the enzyme glutamine phenylpyruvate transaminase (GPT) as a catalyst of 2-hydroxy-5-oxoproline (2-oxoglutaramate) synthesis in plants, and here disclose that transgenic algae engineered to over-express plant-derived GPT and glutamine synthetase (GS1) genes grow faster and produce higher amounts of chlorophyll compared to wild type algae.

In one embodiment, the disclosure provides the generation of GPT+GS1 *Chlorella*. The double-transgenic *Chlorella* demonstrated substantially faster growth rates that the untransformed *Chlorella* grown under identical conditions for the same amount of time. Methods for the generation of the transgenic algae of the invention are provided.

In one embodiment, the disclosure provides a transgenic algae including a GPT transgene and a GS transgene, wherein each of said GPT transgene and said GS transgene is operably linked to a promoter.

In one embodiment, the disclosure provides a transgenic algae including a GPT transgene and a GS transgene, wherein each of said GPT transgene and said GS transgene is operably linked to a promoter, and wherein the algae is a green algae.

In one embodiment, the disclosure provides a transgenic algae including a GPT transgene and a GS transgene, wherein each of said GPT transgene and said GS transgene is operably linked to a promoter, and wherein the algae is selected from a *Chlorella* or *Chlamydomonas* species.

In one embodiment, the disclosure provides a transgenic algae including a GPT transgene and a GS transgene, wherein each of said GPT transgene and said GS transgene is operably linked to a promoter, and wherein the GPT transgene is a plant-derived GPT.

In one embodiment, the disclosure provides a transgenic algae including a GPT transgene and a GS transgene, wherein each of said GPT transgene and said GS transgene is operably linked to a promoter, and wherein the GPT is an algal-derived GPT.

In one embodiment, the disclosure provides a transgenic algae including a GPT transgene and a GS transgene, wherein each of said GPT transgene and said GS transgene is operably linked to a promoter, wherein the GPT transgene is a plant-derived GPT, and wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47.

In one embodiment, the disclosure provides a transgenic algae including a GPT transgene and a GS transgene, wherein each of said GPT transgene and said GS transgene is operably linked to a promoter, wherein the GPT is an algal-derived GPT, and wherein the GPT transgene encodes a polypeptide having an amino acid sequence selected from the group consisting of: SEQ ID NO: 48, and an amino acid sequence that is at least 75% identical to SEQ ID NO: 48.

In one embodiment, the disclosure provides a transgenic algae including a GPT transgene and a GS transgene, wherein each of said GPT transgene and said GS transgene is operably linked to a promoter, and wherein the GS transgene encodes a polypeptide having an amino acid sequence selected from the group consisting of: SEQ ID NO: 4, SEQ ID NO: 7, SEQ ID NO: 39, an amino acid sequence that is at least 75% identical to SEQ ID NO: 4, an amino acid sequence that is at least 75% identical to SEQ ID NO: 7, and an amino acid sequence that is at least 75% identical to SEQ ID NO: 39.

In one embodiment, the disclosure provides a transgenic algae including a GPT transgene and a GS transgene, wherein each of said GPT transgene and said GS transgene is operably linked to a promoter, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the algae is a green algae, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the algae is selected from a *Chlorella* or *Chlamydomonas* species, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the GPT transgene is a plant-derived GPT, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the GPT is an algal-derived GPT, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the GPT transgene is a plant-derived GPT, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the GPT is an algal-derived GPT, wherein the GPT transgene encodes a polypeptide having an amino acid sequence selected from the group consisting of: SEQ ID NO: 48, and an amino acid sequence that is at least 75% identical to SEQ ID NO: 48, and wherein the GPT and GS transgenes are incorporated into the genome of the algae.

In one embodiment, the disclosure provides a transgenic algae including a GPT transgene and a GS transgene, wherein each of said GPT transgene and said GS transgene is operably linked to a promoter, wherein the GS transgene encodes a polypeptide having an amino acid sequence selected from the group consisting of: SEQ ID NO: 4, SEQ ID NO: 7, SEQ ID NO: 39, an amino acid sequence that is at least 75% identical to SEQ ID NO: 4, an amino acid sequence that is at least 75% identical to SEQ ID NO: 7, and an amino acid sequence that is at least 75% identical to SEQ ID NO: 39, and wherein the GPT and GS transgenes are incorporated into the genome of the algae.

In one embodiment, the disclosure provides the progeny of any generation of a transgenic algae including a GPT transgene and a GS transgene, wherein each of said GPT transgene and said GS transgene is operably linked to a promoter, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the algae is a green algae, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the algae is selected from a *Chlorella* or *Chlamydomonas* species, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the GPT transgene is a plant-derived GPT, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the GPT is an algal-derived GPT, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the GPT transgene is a plant-derived GPT, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the GPT is an algal-derived GPT, wherein the GPT transgene encodes a polypeptide having an amino acid sequence selected from the group consisting of: SEQ ID NO: 48, and an amino acid sequence that is at least 75% identical to SEQ ID NO: 48, wherein the GPT and GS transgenes are incorporated into the genome of the algae, and wherein said progeny comprises said GPT transgene and said GS transgene.

In one embodiment, the disclosure provides the progeny of any generation of a transgenic algae including a GPT transgene and a GS transgene, wherein each of said GPT transgene and said GS transgene is operably linked to a promoter, wherein the GS transgene encodes a polypeptide having an amino acid sequence selected from the group consisting of: SEQ ID NO: 4, SEQ ID NO: 7, SEQ ID NO: 39, an amino acid sequence that is at least 75% identical to SEQ ID NO: 4, an amino acid sequence that is at least 75% identical to SEQ ID NO: 7, and an amino acid sequence that is at least 75% identical to SEQ ID NO: 39, wherein the GPT and GS transgenes are incorporated into the genome of the algae, and wherein said progeny comprises said GPT transgene and said GS transgene.

In one embodiment, the disclosure provides a transgenic algae including a GPT transgene and a GS transgene, wherein each of said GPT transgene and said GS transgene is operably linked to a promoter, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the algae is a green algae, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the algae is selected from a *Chlorella* or *Chlamydomonas* species, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the GPT transgene is a plant-derived GPT, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the GPT is an algal-derived GPT, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the GPT transgene is a plant-derived GPT, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the GPT is an algal-derived GPT, wherein the GPT transgene encodes a polypeptide having an amino acid sequence selected from the group consisting of: SEQ ID NO: 48, and an amino acid sequence that is at least 75% identical to SEQ ID NO: 48, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene and a GS transgene, wherein each of said GPT transgene and said GS transgene is operably linked to a promoter, wherein the GS transgene encodes a polypeptide having an amino acid sequence selected from the group consisting of: SEQ ID NO: 4, SEQ ID NO: 7, SEQ ID NO: 39, an amino acid sequence that is at least 75% identical to SEQ ID NO: 4, an amino acid sequence that is at least 75% identical to SEQ ID NO: 7, and an amino acid sequence that is at least 75% identical to SEQ ID NO: 39, wherein the GPT and GS transgenes are incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a method for increasing growth characteristics of an algae relative to a wild type or progenitor algae of the same species, the method including: (a) introducing a GPT transgene into the algae; (b) introducing a GS transgene into the algae or a progeny of the algae; (c) expressing the GPT transgene and the GS transgene in the algae or the progeny of the algae; and, (d) selecting an algae having an increased growth characteristic relative to an algae of the same species that does not contain a GPT transgene or a GS transgene.

In one embodiment, the disclosure provides a method for increasing growth characteristics of an algae relative to a wild type or progenitor algae of the same species, the method including: (a) introducing a GPT transgene into the algae; (b) introducing a GS transgene into the algae or a progeny of the algae; (c) expressing the GPT transgene and the GS transgene in the algae or the progeny of the algae; and, (d) selecting an algae having an increased growth characteristic relative to an algae of the same species that does not contain a GPT transgene or a GS transgene, and wherein the increased growth characteristic is selected from the group consisting of: faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions.

In one embodiment, the disclosure provides a transgenic algae including a GPT transgene, wherein said GPT transgene is operably linked to a promoter.

In one embodiment, the disclosure provides a transgenic algae including a GPT transgene, wherein said GPT transgene is operably linked to a promoter, and wherein the algae is a green algae.

In one embodiment, the disclosure provides a transgenic algae including a GPT transgene, wherein said GPT transgene is operably linked to a promoter, and wherein the algae is selected from a *Chlorella* or *Chlamydomonas* species.

In one embodiment, the disclosure provides a transgenic algae including a GPT transgene, wherein said GPT transgene is operably linked to a promoter, and wherein the GPT transgene is a plant-derived GPT.

In one embodiment, the disclosure provides a transgenic algae including a GPT transgene, wherein said GPT transgene is operably linked to a promoter, and wherein the GPT is an algal-derived GPT.

In one embodiment, the disclosure provides a transgenic algae including a GPT transgene, wherein said GPT transgene is operably linked to a promoter, wherein the GPT transgene is a plant-derived GPT, and wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47.

In one embodiment, the disclosure provides a transgenic algae including a GPT transgene, wherein said GPT transgene is operably linked to a promoter, and wherein the GPT is an algal-derived GPT, and wherein the GPT transgene encodes a polypeptide having an amino acid sequence selected from the group consisting of: SEQ ID NO: 48, and an amino acid sequence that is at least 75% identical to SEQ ID NO: 48.

In one embodiment, the disclosure provides a transgenic algae including a GPT transgene, wherein said GPT transgene is operably linked to a promoter, and wherein the GPT transgene is incorporated into the genome of the algae.

In one embodiment, the disclosure provides a transgenic algae including a GPT transgene, wherein said GPT transgene is operably linked to a promoter, wherein the algae is a green algae, and wherein the GPT transgene is incorporated into the genome of the algae.

In one embodiment, the disclosure provides a transgenic algae including a GPT transgene, wherein said GPT transgene is operably linked to a promoter, wherein the algae is selected from a *Chlorella* or *Chlamydomonas* species, and wherein the GPT transgene is incorporated into the genome of the algae.

In one embodiment, the disclosure provides a transgenic algae including a GPT transgene, wherein said GPT transgene is operably linked to a promoter, wherein the GPT transgene is a plant-derived GPT, and wherein the GPT transgene is incorporated into the genome of the algae.

In one embodiment, the disclosure provides a transgenic algae including a GPT transgene, wherein said GPT transgene is operably linked to a promoter, wherein the GPT is an algal-derived GPT, and wherein the GPT transgene is incorporated into the genome of the algae.

In one embodiment, the disclosure provides a transgenic algae including a GPT transgene, wherein said GPT transgene is operably linked to a promoter, wherein the GPT transgene is a plant-derived GPT, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47, and wherein the GPT transgene is incorporated into the genome of the algae.

In one embodiment, the disclosure provides a transgenic algae including a GPT transgene, wherein said GPT transgene is operably linked to a promoter, and wherein the GPT is an algal-derived GPT, wherein the GPT transgene encodes a polypeptide having an amino acid sequence selected from the group consisting of: SEQ ID NO: 48, and an amino acid sequence that is at least 75% identical to SEQ ID NO: 48, and wherein the GPT transgene is incorporated into the genome of the algae.

In one embodiment, the disclosure provides a progeny of any generation of a transgenic algae including a GPT transgene, wherein said GPT transgene is operably linked to a promoter, wherein the GPT transgene is incorporated into the genome of the algae, and wherein said progeny comprises said GPT transgene.

In one embodiment, the disclosure provides a progeny of any generation of a transgenic algae including a GPT transgene, wherein said GPT transgene is operably linked to a promoter, wherein the algae is a green algae, wherein the GPT transgene is incorporated into the genome of the algae, and wherein said progeny comprises said GPT transgene.

In one embodiment, the disclosure provides a progeny of any generation of a transgenic algae including a GPT transgene, wherein said GPT transgene is operably linked to a promoter, wherein the algae is selected from a *Chlorella* or *Chlamydomonas* species, wherein the GPT transgene is incorporated into the genome of the algae, and wherein said progeny comprises said GPT transgene.

In one embodiment, the disclosure provides a progeny of any generation of a transgenic algae including a GPT transgene, wherein said GPT transgene is operably linked to a promoter, wherein the GPT transgene is a plant-derived GPT, wherein the GPT transgene is incorporated into the genome of the algae, and wherein said progeny comprises said GPT transgene.

In one embodiment, the disclosure provides a progeny of any generation of a transgenic algae including a GPT transgene, wherein said GPT transgene is operably linked to a promoter, wherein the GPT is an algal-derived GPT, wherein the GPT transgene is incorporated into the genome of the algae, and wherein said progeny comprises said GPT transgene.

In one embodiment, the disclosure provides a progeny of any generation of a transgenic algae including a GPT transgene, wherein said GPT transgene is operably linked to a promoter, wherein the GPT transgene is a plant-derived GPT, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47, wherein the GPT transgene is incorporated into the genome of the algae, and wherein said progeny comprises said GPT transgene.

In one embodiment, the disclosure provides a progeny of any generation of a transgenic algae including a GPT transgene, wherein said GPT transgene is operably linked to a promoter, and wherein the GPT is an algal-derived GPT, wherein the GPT transgene encodes a polypeptide having an amino acid sequence selected from the group consisting of: SEQ ID NO: 48, and an amino acid sequence that is at least 75% identical to SEQ ID NO: 48, wherein the GPT transgene is incorporated into the genome of the algae, and wherein said progeny comprises said GPT transgene.

In one embodiment, the disclosure provides a transgenic algae including a GPT transgene, wherein said GPT transgene is operably linked to a promoter, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene, wherein said GPT transgene is operably linked to a promoter, wherein the algae is a green algae, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene, wherein said GPT transgene is operably linked to a promoter, wherein the algae is selected from a *Chlorella* or *Chlamydomonas* species, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene, wherein said GPT transgene is operably linked to a promoter, wherein the GPT transgene is a plant-derived GPT, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene, wherein said GPT transgene is operably linked to a promoter, wherein the GPT is an algal-derived GPT, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene, wherein said GPT transgene is operably linked to a promoter, wherein the GPT transgene is a plant-derived GPT, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 35, SEQ ID NO: 36, SEQ ID NO: 44, SEQ ID NO: 47, an amino acid sequence that is at least 75% identical to SEQ ID NO: 2, an amino acid sequence that is at least 75% identical to SEQ ID NO: 9, an amino acid sequence that is at least 75% identical to SEQ ID NO: 15, an amino acid sequence that is at least 75% identical to SEQ ID NO: 19, an amino acid sequence that is at least 75% identical to SEQ ID NO: 21, an amino acid sequence that is at least 75% identical to SEQ ID NO 24, an amino acid sequence that is at least 75% identical to SEQ ID NO: 30, an amino acid sequence that is at least 75% identical to SEQ ID NO:31, an amino acid sequence that is at least 75% identical to SEQ ID NO: 32, an amino acid sequence that is at least 75% identical to SEQ ID NO: 33, an amino acid sequence that is at least 75% identical to SEQ ID NO: 34, an amino acid sequence that is at least 75% identical to SEQ ID NO: 35, an amino acid sequence that is at least 75% identical to SEQ ID NO: 36, an amino acid sequence that is at least 75% identical to SEQ ID NO: 44, and an amino acid sequence that is at least 75% identical to SEQ ID NO: 47, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a transgenic algae including a GPT transgene, wherein said GPT transgene is operably linked to a promoter, and wherein the GPT is an algal-derived GPT, wherein the GPT transgene encodes a polypeptide having an amino acid sequence selected from the group consisting of: SEQ ID NO: 48, and an amino acid sequence that is at least 75% identical to SEQ ID NO: 48, wherein the GPT transgene is incorporated into the genome of the algae, and wherein the transgenic algae displays a faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions when compared to an analogous wild-type or untransformed algae.

In one embodiment, the disclosure provides a method for increasing growth characteristics of an algae relative to an wild type or progenitor algae of the same species, the method including: (a) introducing a GPT transgene into the algae; (b) expressing the GPT transgene in the algae or the progeny of the algae; and, (c) selecting an algae having an increased growth characteristic relative to an algae of the same species that does not comprise a GPT transgene.

In one embodiment, the disclosure provides a method for increasing growth characteristics of an algae relative to an wild type or progenitor algae of the same species, the method including: (a) introducing a GPT transgene into the algae; (b) expressing the GPT transgene in the algae or the progeny of the algae; and, (c) selecting an algae having an increased growth characteristic relative to an algae of the same species that does not comprise a GPT transgene, wherein the increased growth characteristic is selected from the group consisting of: faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions.

BRIEF DESCRIPTION OF THE DRAWINGS

FIG. 1. Photograph of tissue culture plates, showing GPT+ GS1 transformed *Chlorella vulgaris* on the right, and untransformed *Chlorella vulgaris* (control) on the left. See, Example 1, infra.

DETAILED DESCRIPTION OF THE INVENTION

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y.; Current Protocols in Molecular Biology (Ausbel et al., eds., John Wiley & Sons, Inc. 2001). As appropriate, procedures involving the use of commercially available kits and reagents are generally carried out in accordance with manufacturer defined protocols and/or parameters unless otherwise noted.

The term "nucleic acid" refers to deoxyribonucleotides or ribonucleotides and polymers thereof ("polynucleotides") in either single- or double-stranded form. Unless specifically limited, the term "polynucleotide" encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991, Nucleic Acid Res. 19:5081; Ohtsuka et al., 1985 J. Biol. Chem. 260:2605-2608; and Cassol et al., 1992; Rossolini et al., 1994, Mol. Cell. Probes 8:91-98). The term nucleic acid is used interchangeably with gene, cDNA, and mRNA encoded by a gene.

The term "promoter" refers to a nucleic acid control sequence or sequences that direct transcription of an operably linked nucleic acid. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "algae" refers to photosynthetic organisms of multiple phylogenetic groups, and includes numerous unicellular and multicellular species. The term "algae" as used herein includes organisms of the following phylogenetic groups: Chlorophyta (green algae; includes mostly fresh water species); Phaeophyta (brown algae; includes mostly marine species); Rhodophyta (red algae; includes mostly marine species); Chrysophyta; Xanthophyta; Bacillariophyta; Euglenophyta; Cryptophyta; Pyrrophyta; Raphidophyta; Haptophyta; Eustigmatophyta; Prasinophyta; Glaucophyta and Cyanobacteria (prokaryotic, blue-green algae). The class of algae which can be used in the methods of the invention is generally as broad as the class of algae amenable to transformation techniques.

Algae of the present disclosure include but are not limited to organisms of the following genera: *Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanidioschyzon, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium, Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Kappaphycus Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Laminaria, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Nae-*

*geliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Ostreococcus, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodactylum Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyra, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symbiodinium, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis*, and *Zygonium*.

The terms "GPT polynucleotide" and "GPT nucleic acid" are used interchangeably herein, and refer to a full length or partial length polynucleotide sequence of a gene which encodes a polypeptide involved in catalyzing the synthesis of 2-oxoglutaramate, and includes polynucleotides containing both translated (coding) and un-translated sequences, as well as the complements thereof. The term "GPT coding sequence" refers to the part of the gene which is transcribed and encodes a GPT protein. The term "targeting sequence" refers to the amino terminal part of a protein which directs the protein into a subcellular compartment of a cell, such as a chloroplast. GPT polynucleotides are further defined by their ability to hybridize under defined conditions to the GPT polynucleotides specifically disclosed herein, or to PCR products derived therefrom.

A "GPT transgene" is a nucleic acid molecule including a GPT polynucleotide which is exogenous to a transgenic algae harboring the nucleic acid molecule, or which is exogenous to an ancestor algae, of a transgenic algae harboring the GPT polynucleotide. More particularly, the exogenous GPT transgene will be heterogeneous with any GPT polynucleotide sequence present in wild-type algae into which the GPT transgene is inserted. To this extent, the scope of the heterogeneity required need only be a single nucleotide difference. However, preferably the heterogeneity will be in the order of an identity between sequences selected from the following identities: 0.01%, 0.05%, 0.1%, 0.5%, 1%, 5%, 10%, 15%, and 20%.

The terms "GS polynucleotide" and "GS nucleic acid" are used interchangeably herein, and refer to a full length or partial length polynucleotide sequence of a gene which encodes a glutamine synthetase protein, and includes polynucleotides containing both translated (coding) and un-translated sequences, as well as the complements thereof. The term "GS coding sequence" refers to the part of the gene which is transcribed and encodes a GS protein. The terms "GS1 polynucleotide" and "GS1 nucleic acid" are used interchangeably herein, and refer to a full length or partial length polynucleotide sequence of a gene which encodes a glutamine synthetase isoform 1 protein, and includes polynucleotides containing both translated (coding) and un-translated sequences, as well as the complements thereof. The term "GS1 coding sequence" refers to the part of the gene which is transcribed and encodes a GS1 protein.

A "GS transgene" is a nucleic acid molecule including a GS polynucleotide which is exogenous to a transgenic algae, or which is exogenous to an ancestor algae of a transgenic algae harboring the GS polynucleotide. A "GS1 transgene" is a nucleic acid molecule including a GS1 polynucleotide which is exogenous to a transgenic algae harboring the nucleic acid molecule, or which is exogenous to an ancestor algae of a transgenic algae harboring the GS1 polynucleotide. More particularly, the exogenous GS or GS1 transgene will be heterogeneous with any GS or GS1 polynucleotide sequence present in wild-type algae into which the GS or GS1 transgene is inserted. To this extent the scope of the heterogeneity required need only be a single nucleotide difference. However, preferably the heterogeneity will be in the order of an identity between sequences selected from the following identities: 0.01%, 0.05%, 0.1%, 0.5%, 1%, 5%, 10%, 15%, and 20%.

Exemplary GPT from algae, higher plants and a fish are presented herein, and include GPT sequences derived from *Chlorella*, *Arabidopsis*, Rice, Barley, Bamboo°, Soybean, Grape, and Zebra Fish. GS and GS1 proteins are known; exemplary GS1 sequences provided herein include *Arabidopsis* and *Hordeum*.

Partial length GPT polynucleotides include polynucleotide sequences encoding N- or C-terminal truncations of GPT, mature GPT (without targeting sequence) as well as sequences encoding domains of GPT. Exemplary GPT polynucleotides encoding N-terminal truncations of GPT include

*Arabidopsis* −30, −45 and −56 constructs, in which coding sequences for the first 30, 45, and 56, respectively, amino acids of the full length GPT structure of SEQ ID NO: 2 are eliminated.

In employing the GPT polynucleotides of the invention in the generation of transformed algal cells and transgenic algae, one of skill will recognize that the inserted polynucleotide sequence need not be identical, but may be only "substantially identical" to a sequence of the gene from which it was derived, as further defined below. The term "GPT polynucleotide" specifically encompasses such substantially identical variants. Similarly, one of skill will recognize that because of codon degeneracy, a number of polynucleotide sequences will encode the same polypeptide, and all such polynucleotide sequences are meant to be included in the term GPT polynucleotide. In addition, the term specifically includes those sequences substantially identical (determined as described below) with a GPT polynucleotide sequence disclosed herein and that encode polypeptides that are either mutants of wild type GPT polypeptides or retain the function of the GPT polypeptide (e.g., resulting from conservative substitutions of amino acids in a GPT polypeptide). The term "GPT polynucleotide" therefore also includes such substantially identical variants.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., Molecular Biology of the Cell (3$^{rd}$ ed., 1994) and Cantor and Schimmel, *Biophysical Chemistry Part 1: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the non-covalent association of independent tertiary units. Anisotropic terms are also known as energy terms.

The term "isolated" refers to material which is substantially or essentially free from components which normally accompany the material as it is found in its native or natural state. However, the term "isolated" is not intended refer to the components present in an electrophoretic gel or other separation medium. An isolated component is free from such separation media and in a form ready for use in another application or already in use in the new application/milieu. An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "heterologous" when used with reference to portions of a nucleic acid indicates that the nucleic acid comprises two or more subsequences that are not found in the same relationship to each other in nature. For instance, a nucleic acid is typically recombinantly produced, having two or more sequences from unrelated genes arranged to make a new functional nucleic acid, e.g., a nucleic acid encoding a protein from one source and a nucleic acid encoding a peptide sequence from another source. Similarly, a heterologous protein indicates that the protein comprises two or more subsequences that are not found in the same relationship to each other in nature (e.g., a fusion protein).

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, or 95% identity over a specified region, when compared and aligned for maximum correspondence over a comparison window, or designated region as measured using a sequence comparison algorithms, or by manual alignment and visual inspection. This definition also refers to the complement of a test sequence, which has substantial sequence or subsequence complementarity when the test sequence has substantial identity to a reference sequence. This definition also refers to the complement of a test sequence, which has substantial sequence or subsequence complementarity when the test sequence has substantial identity to a reference sequence.

When percentage of sequence identity is used in reference to polypeptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the polypeptide. Where sequences differ in conservative substitutions, the percent sequence identity may be adjusted upwards to correct for the conservative nature of the substitution.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned.

Methods of alignment of sequences for comparison are well-known in the art. Optimal alignment of sequences for comparison can be conducted, e.g., by the local homology algorithm of Smith & Waterman, 1981, Adv. Appl. Math. 2:482, by the homology alignment algorithm of Needleman & Wunsch, 1970, J. Mol. Biol. 48:443, by the search for similarity method of Pearson & Lipman, 1988, Proc. Narl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., 1977, Nue. Acids Res. 25:3389-3402 and Altschul et al., 1990, J. Mol. Biol. 215:403-410, respectively. BLAST and BLAST 2.0 are used, typically with the default parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, Proc. Nat'l. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5-10° C. lower than the thermal melting point (Tm) for the specific sequence at a defined ionic strength pH. Low stringency conditions are generally selected to be about 15-30° C. below the Tm. Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0M sodium ion, typically about 0.01 to 1.0M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide For selective or specific hybridization, a positive signal is at least two times background, preferably 10 times background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

Genomic DNA or cDNA including GPT polynucleotides may be identified in standard Southern blots under stringent conditions using the GPT polynucleotide sequences disclosed here. For this purpose, suitable stringent conditions for such hybridizations are those which include a hybridization in a buffer of 40% formamide, 1M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions may be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

Transgenic Algae:

The invention provides novel transgenic algae exhibiting faster growth and increased chlorophyll production. The transgenic algae of the invention are generated by introducing into algae cells one or more expressible genetic constructs capable of driving the expression of one or more polynucleotides encoding glutamine phenylpyruvate transaminase (GPT), and in some embodiments, one or more polynucleotides encoding glutamine synthetase (GS) and GPT.

The transgenic algae of the invention may be of any species capable of transformation, including those from the subphyla Chlorophyta, Chrysophyta, Phaeophyta, Rhodophyta, as well as the Cyanobacteria. In the last few years, successful genetic transformation of ~25 algal species has been demonstrated, mostly via nuclear transformation (Hallmann, 2007, Transgenic Plant Journal 1:81-98). Among these, at least ten green algae species have been successfully transformed (mostly all unicellular species). Several species of red algae, brown algae and diatom species has also been reported (Hallmann, 2007, supra).

Improving the production step of algal biofuels production is being approached in more or less the standard ways of improving biological production, i.e., by optimizing nutrients, growth conditions and light/energy supply. Mineral nutrient supplies are being optimized through detailed studies of the need for each nutrient, and at what stoichiometry relative to other nutrients. The availability of carbon dioxide is being maximized typically with various delivery systems, each designed to maximize the amount of carbon dioxide dissolved in the water. As well, pH is being maintained at or near the optimum for growth.

Some attempts have been made to grow algal faster and more economically by establishing heterotrophic growth conditions. This has been achieved by providing fixed carbon, such as sugars, for the algae to use as carbon and energy sources. Algae also require an optimal amount of light to provide the energy for growth. The light impinging upon an algal cell is converted to chemical energy and used to drive the algal metabolism and cell growth. The amount of light striking algal cells in growing cultures is impacted by culture density, the distance the light must penetrate into the culture (i.e., the cells at the surface receive more light than cells further from the surface), and the amount of light receptors within an algal cell. Algal bioreactor designs are being tested that range from deep or shallow horizontal ponds to vertical glass/plastic reactors.

Alga cells over-expressing GPT and GS transgenes can be expected to take much better advantage of the optimized nutrients and the high availability of carbon dioxide, because they can be expected to increase their carbon dioxide fixing machinery, the ribulose bisphosphate carboxylase (RUBISCO) enzyme protein and activity state. If algae respond in the same way GPT+GS1 transgenic plants do (see co-owned, co-pending U.S. patent application Ser. No. 12/551,271), the over-expression of the GPT and GS transgenes in algae may be accompanied by increased expression of genes encoding RUBISCO subunits and the RUBISCO activase enzyme which controls the activity state of RUBISCO. The transgenic algae of the invention may also increase their capacity for and rate of uptake of nitrogen-based nutrients such as nitrate and ammonia. Such increased carbon fixation will result in increased flux through central metabolism and the incumbent increase in the concentration of organic acids that are known to induce production of the nitrogen uptake transporters.

In stable transformation embodiments of the invention, one or more copies of the expressible genetic construct become integrated into the host algae genome, thereby providing increased GS and/or GPT enzyme capacity into the algae, which may serve to mediate increased synthesis of 2-oxoglutaramate therein, which in turn signals metabolic gene expression, resulting in increased algal growth. 2-oxoglutaramate is a metabolite which is an extremely potent effector of gene expression, metabolism and plant growth (U.S. Pat. No. 6,555,500), and which may play a pivotal role in the coordination of the carbon and nitrogen metabolism systems in plants (Lancien et al., 2000, Enzyme Redundancy and the Importance of 2-Oxoglutarate in *Higher Plants Ammonium Assimilation*, Plant Physiol. 123:817-824).

The invention also provides methods of generating transgenic algae having faster growth rates. In one embodiment, a method of generating a transgenic algae having a faster growth rate, introducing into an algal cell an expression cassette including a nucleic acid molecule encoding a GPT transgene, under the control of a suitable promoter capable of driving the expression of the transgene, so as to yield a transformed algal cell, and obtaining a transgenic algae which expresses the encoded GPT. In another embodiment, a method of generating a transgenic algae having a faster growth rate comprises introducing into an algal cell one or more nucleic acid constructs or expression cassettes including nucleic acid molecules encoding a GPT transgene and an GS transgene, under the control of one or more suitable promoters (and, optionally, other regulatory elements) capable of driving the expression of the transgenes, so as to yield an algal cell transformed thereby, and obtaining a transgenic algae which expresses the GPT and GS transgenes.

GPT and GS transgenes suitable for use in generating the transgenic algae of the invention are described in co-owned, co-pending U.S. patent application Ser. No. 12/551,271. Other GPT polynucleotides suitable for use as GPT transgenes in the practice of the invention may be obtained by various means, as will be appreciated by one skilled in the art, tested for the ability to direct the expression of a GPT with GPT activity in a recombinant expression, or in a transient in planta expression system (U.S. Ser. No. 12/551,271, supra), or preferably in a transgenic algae.

Transgene Constructs/Algal Expression Vectors

In order to generate the transgenic algae of the invention, the gene coding sequence for the desired transgene(s) must be incorporated into a nucleic acid construct (also interchangeably referred to herein as a/an (transgene) expression vector, expression cassette, expression construct or expressible genetic construct), which can direct the expression of the transgene sequence in transformed algal cells. Such nucleic acid constructs carrying the transgene(s) of interest may be introduced into an algal cell or cells using a number of methods known in the art, including but not limited to electroporation, DNA bombardment or biolistic approaches, microinjection, and via the use of various DNA-based vectors. Once introduced into the transformed algal cell, the nucleic acid construct may direct the expression of the incorporated transgene(s) (i.e., GPT), either in a transient or stable fashion. Stable expression is preferred, and is achieved by utilizing transformation vectors which are able to direct the chromosomal integration of the transgene construct.

The basic elements of a nucleic acid construct for use in generating the transgenic algae of the invention are: a suitable promoter capable of directing the functional expression of the transgene(s) in a transformed algae cell, the transgene(s) (i.e., GPT coding sequence) operably linked to the promoter, preferably a suitable transcription termination sequence (i.e., nopaline synthetic enzyme gene terminator) operably linked to the transgene, and sometimes other elements useful for controlling the expression of the transgene, as well as one or more selectable marker genes suitable for selecting the desired transgenic product (i.e., antibiotic resistance genes).

Various plant, algae and animal GPT protein sequences and encoding DNA and GPT transgene expression constructs are presented in the Table of Sequences, infra. Similarly, various GS1 protein sequences and encoding DNA and GS1 transgene expression constructs are provided. These sequences are provided as examples and should not be considered limiting.

Typically, algae is transformed by causing the temporal permeabilization of the cell membrane, there by enabling vector DNA to enter the algal cell. DNA integration occurs naturally, by recombination events, resulting in ectopic integration into the algal genome, resulting in stable events. Biolistic approaches, such as particle bombardment, are typically used to transform algal cells. Polyethylene glycol mixtures using DNA coated particle has also been successfully utilized. Additionally, certain wall-reduced algae strains have been employed, in order to achieve protoplast transformation in the presence of polyethylene glycol and the transgene construct. Electroporation and even *Agrobacterium*-mediated transformation of algae has been reported. For details, and references to published reports of various transformation protocols and vector systems, see Hallmann, 2007, supra for review.

Any promoter capable of being functional in algae may be used to direct the expression of the GPT or GPT+GS transgene constructs. In preferred embodiments, the promoter may be an endogenous algal promoter. Various vectors used to transform algae are known, including plasmid vectors which become integrated into the nucleus of algal cells and there direct the cytoplasmic expression of the transgene products (i.e., plasmid pSSCR7, Davies et al., 1994, Plant Cell 6:53-63). Other nuclear-directed vectors direct transgene expression products to the periplasm. One such vector is a derivative of pSSCR7, modified to incorporate a 5' aryl sulfatase periplasmic targeting transit sequence (Davies et al., 1994, supra). Still other vectors direct transgene integration to the chloroplast plastome by homologous recombination, whereby transgene expression is localized to the chloroplast (Hutchinson, et al., 1996, In: Molecular Genetics of Photosynthesis, Frontiers in Molecular Biology. Anderson B., Salter A H, and Barber J. eds., Oxford University Press, pp. 180-196).

EXAMPLES

Various aspects of the invention are further described and illustrated by way of the example which follows, which is not intended to limit the scope of the invention.

Example 1

Generation of Transgenic *Chlorella*

Materials and Methods:

*Chlorella vulgaris* strain #259 was purchased from Culture Collection of Algae at the University of Texas (UTEX, Austin, Tex.), and maintained as recommended on Bristol medium.

Two transgene expression vectors were assembled and used to transform the algae with electroporation. The first vector was the Cambia 1201 vector containing Tomato Rubisco small subunit promoter and *Arabidopsis* GS (SEQ ID NO: 45). The second vector was the Cambia 1305.1 vector containing 35S CMV promoter *Zea mays* full length GPT gene sequence [SEQ ID NO: 46]

Electrotransformation was used to insert these vectors simultaneously into the *Chlorella* culture; this was carried out according to the method of K. C. Chow and W. L. Tung. (Electrotransformation of *Chlorella vulgaris*. Plant Cell Reports 1999 18:778-780). The antibiotic selection was Hygromycin B at a concentration of 20 micrograms/ml. Bristol peptone digest media (UTEX web site) was used to culture the cells on plates.

Results:

Transformed and control algae were plated out identically. Twelve days later, 15 dark green colonies were observed growing on the transformed plate and none on the control plate. FIG. 1 shows a photograph of the transformed (right) and untransformed (control, left) *Chlorella*, taken 23 days post-plating. Vigorous green cultures were seen only on the transformed algae plate. In addition, the transformed algae colonies showed far greener and darker coloration compared the control algae. The dark green is chlorophyll, and the increase in chlorophyll per cell has been observed as a characteristic of the faster growing plants. Finally, the colony count at day 15 post-plating, and the much greater colony numbers at 23 days post-plating, are consistent with faster growth.

All publications, patents, and patent applications cited in this specification are herein incorporated by reference as if each individual publication or patent application were specifically and individually indicated to be incorporated by reference.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLE OF SEQUENCES:

SEQ ID NO: 1 Arabidopsis glutamine phenylpyruvate
transaminase DNA coding sequence:
ATGTACCTGGACATAAATGGTGTGATGATCAAACAGTTTAGCTTCAAAGCCTCTCTT
CTCCCATTCTCTTCTAATTTCCGACAAAGCTCCGCCAAAATCCATCGTCCTATCGGAG
CCACCATGACCACAGTTTCGACTCAGAACGAGTCTACTCAAAAACCCGTCCAGGTG
GCGAAGAGATTAGAGAAGTTCAAGACTACTATTTTCACTCAAATGAGCATATTGGCA
GTTAAACATGGAGCGATCAATTTAGGCCAAGGCTTTCCCAATTTCGACGGTCCTGAT
TTTGTTAAAGAAGCTGCGATCCAAGCTATTAAAGATGGTAAAAACCAGTATGCTCGT
GGATACGGCATTCCTCAGCTCAACTCTGCTATAGCTGCGCGGTTTCGTGAAGATACG
GGTCTTGTTGTTGATCCTGAGAAAGAAGTTACTGTTACATCTGGTTGCACAGAAGCC
ATAGCTGCAGCTATGTTGGGTTTAATAAACCCTGGTGATGAAGTCATTCTCTTTGCA
CCGTTTTATGATTCCTATGAAGCAACACTCTCTATGGCTGGTGCTAAAGTAAAAGGA
ATCACTTTACGTCCACCGGACTTCTCCATCCCTTTGGAAGAGCTTAAAGCTGCGGTA
ACTAACAAGACTCGAGCCATCCTTATGAACACTCCGCACAACCCGACCGGGAAGAT
GTTCACTAGGGAGGAGCTTGAAACCATTGCATCTCTCTGCATTGAAAACGATGTGCT
TGTGTTCTCGGATGAAGTATACGATAAGCTTGCGTTTGAAATGGATCACATTTCTAT
AGCTTCTCTTCCCGGTATGTATGAAAGAACTGTGACCATGAATTCCCTGGGAAAGAC
TTTCTCTTTAACCGGATGGAAGATCGGCTGGGCGATTGCGCCGCCTCATCTGACTTG
GGGAGTTCGACAAGCACACTCTTACCTCACATTCGCCACATCAACACCAGCACAATG
GGCAGCCGTTGCAGCTCTCAAGGCACCAGAGTCTTACTTCAAAGAGCTGAAAAGAG
ATTACAATGTGAAAAAGGAGACTCTGGTTAAGGGTTTGAAGGAAGTCGGATTTACA
GTGTTCCCATCGAGCGGGACTTACTTTGTGGTTGCTGATCACACTCCATTTGGAATG
GAGAACGATGTTGCTTTCTGTGAGTATCTTATTGAAGAAGTTGGGGTCGTTGCGATC
CCAACGAGCGTCTTTTATCTGAATCCAGAAGAAGGGAAGAATTTGGTTAGGTTTGCG
TTCTGTAAAGACGAAGAGACGTTGCGTGGTGCAATTGAGAGGATGAAGCAGAAGCT
TAAGAGAAAAGTCTGA SEQ ID NO: 2 Arabidopsis GPT amino acid sequence
MYLDINGVMIKQFSFKASLLPFSSNFRQSSAKIHRPIGATMTTVSTQNESTQKPVQVAKR
LEKFKTTIFTQMSILAVKHGAINLGQGFPNFDGPDFVKEAAIQAIKDGKNQYARGYGIPQ
LNSAIAARFREDTGLVVDPEKEVTVTSGCTEAIAAAMLGLINPGDEVILFAPFYDSYEAT
LSMAGAKVKGITLRPPDFSIPLEELKAAVTNKTRAILMNTPHNPTGKMFTREELETIASL
CIENDVLVFSDEVYDKLAFEMDHISIASLPGMYERTVTMNSLGKTFSLTGWKIGWAIAPP
HLTWGVRQAHSYLTFATSTPAQWAAVAALKAPESYFKELKRDYNVKKETLVKGLKEV
GFTVFPSSGTYFVVADHTPFGMENDVAFCEYLIEEVGVVAIPTSVFYLNPEEGKNLVRFA
FCKDEETLRGAIERMKQKLKRKV SEQ ID NO: 3 Alfalfa GS1 DNA coding sequence (upper case)
with 5' and 3' untranslated
sequences (indicated in lower case).
Atttccgttttcgttttcatttgattcattgaatcaaatcgaatcgaatctttaggat
tcaatacagattccttagattttactaagtttgaaaccaaaaccaaaacATGTCTCT
CCTTTCAGATCTTATCAACCTTGACCTCTCCGAAACCACCGAGAAAATCATCGCCGAA
TACATATGGATTGGTGGATCTGGTTTGGACTTGAGGAGCAAAGCAAGGACTCTACCAGG
ACCAGTTACTGACCCTTCACAGCTTCCCAAGTGGAACTATGATGGTTCCAGCACAGGT
CAAGCTCCTGGAGAAGATAGTGAAGTTATTATCTACCCACAAGCCATTTTCAAGGACCC
ATTTAGAAGGGGTAACAATATCTTGGTTATGTGTGATGCATACACTCCAGCTGGAGAGC
CCATTCCCACCAACAAGAGACATGCAGCTGCCAAGATTTTCAGCCATCCTGATGTTGTTG
CTGAAGTACCATGGTATGGTATTGAGCAAGAATACACCTTGTTGCAGAAAGACATCAATT
GGCCTCTTGGTTGGCCAGTTGGTGGTTTTCCTGGACCTCAGGGACCATACTATTGTGGAG
CTGGTGCTGACAAGGCATTTGGCCGTGACATTGTTGACTCACATTACAAAGCCTGTCTTT
ATGCCGGCATCAACATCAGTGGAATCAATGGTGAAGTGATGCCTGGTCAATGGGAATTCC
AAGTTGGTCCCTCAGTTGGTATCTCTGCTGGTGATGAGATATGGGTTGCTCGTTACATTT
TGGAGAGGATCACTGAGGTTGCTGGTGTGGTGCTTTCCTTTGACCCAAAACCAATTAAGG
GTGATTGGAATGGTGCTGGTGCTCACACAAATTACAGCACCAAGTCTATGAGAGAAGATG
GTGGCTATGAAGTCATCTTGAAAGCAATTGAGAAGCTTGGGAAGAAGCACAAGGAGCACA
TTGCTGCTTATGGAGAAGGCAACGAGCGTAGATTGACAGGGCGACATGAGACAGCTGACA
TTAACACCTTCTTATGGGGTGTTGCAAACCGTGGTGCGTCGATTAGAGTTGGAAGGGACA
CAGAGAAAGCAGGGAAAGGTTATTTCGAGGATAGGAGGCCATCATCTAACATGGAT
CCATATGTTGTTACTTCCATGATTGCAGACACCACCATTCTCTGGAAACCATAAgccac
cacacacacatgcattgaagtatttgaaagtcattgttgattccgcattagaatttggt
cattgtttttctaggatttggatttgtgttattgttatggttcacactttgtttgt
ttgaatttgaggccttgttataggtttcatatttctttctcttgttctaagtaaatg
tcagaataataatgtaat SEQ ID NO: 4 Alfalfa GS1 amino acid sequence
MSLLSDLINLDLSETTEKIIAEYIWIGGSGLDLRSKARTLPGPVTDPSQLPKWNYDGSSTG
QAPGEDSEVIIYPQAIFKDPFRRGNNILVMCDAYTPAGEPIPTNKRHAAAKIFSHPDVVAE
VPWYGIEQEYTLLQKDINWPLGWPVGGFPGPQGPYYCGAGADKAFGRDIVDSHYKACL
YAGINISGINGEVMPGQWEFQVGPSVGISAGDEIWVARYILERITEVAGVVLSFDPKPIKG
DWNGAGAHTNYSTKSMREDGGYEVILKAIEKLGKKHKEHIAAYGEGNERRLTGRHETA
DINTFLWGVANRGASIRVGRDTEKAGKGYFEDRRPSSNMDPYVVTSMIADTTILWKP SEQ ID NO: 5 Alfalfa GS1 DNA coding sequence (upper case)
with 5' and 3' untranslated sequences (indicated in lower
case) and vector sequences from Cla1 to Sma1/Ssp1 and
Ssp1/Sma1 to Sal1/Xho1 (lower case, underlined).
<u>atcgatgaattcgagctcggtaccc</u>atttccgttttcgttttcatttgattcattgaatca
aatcgaatcgaatctttaggattcaatacagattccttagattttactaagttt

TABLE OF SEQUENCES:

gaaaccaaaaccaaaacATGTCTCTCCTTTCAGATCTTATCAACCTTGACCTCTCC
GAAACCACCGAGAAATCATCGCCGAATACATATGGATTGGTGGATCTGGTTTGGA
CTTGAGGAGCAAAGCAAGGACTCTACCAGGACCAGTTACTGACCCTTCACAGCTTCC
CAAGTGGAACTATGATGGTTCCAGCACAGGTCAAGCTCCTGGAGAAGATAGTGAAG
TTATTATCTACCCACAAGCCATTTTCAAGGACCCATTTAGAAGGGGTAACAATATCT
TGGTTATGTGTGATGCATACACTCCAGCTGGAGAGCCCATTCCCACCAACAAGAGAC
ATGCAGCTGCCAAGATTTTCAGCCATCCTGATGTTGTTGCTGAAGTACCATGGTATG
GTATTGAGCAAGAATACACCTTGTTGCAGAAAGACATCAATTGGCCTCTTGGTTGGC
CAGTTGGTGGTTTTCCTGGACCTCAGGGACCATACTATTGTGGAGCTGGTGCTGACA
AGGCATTTGGCCGTGACATTGTTGACTCACATTACAAAGCCTGTCTTTATGCCGGCA
TCAACATCAGTGGAATCAATGGTGAAGTGATGCCTGGTCAATGGGAATTCCAAGTTG
GTCCCTCAGTTGGTATCTCTGCTGGTGATGAGATATGGGTTGCTCGTTACATTTTGGA
GAGGATCACTGAGGTTGCTGGTGTGGTGCTTTCCTTTGACCCAAAACCAATTAAGGG
TGATTGGAATGGTGCTGGTGCTCACACAAATTACAGCACCAAGTCTATGAGAGAAG
ATGGTGGCTATGAAGTCATCTTGAAAGCAATTGAGAAGCTTGGGAAGAAGCACAAG
GAGCACATTGCTGCTTATGGAGAAGGCAACGAGCGTAGATTGACAGGGCGACATGA
GACAGCTGACATTAACACCTTCTTATGGGGTGTTGCAAACCGTGGTGCGTCGATTAG
AGTTGGAAGGGACACAGAGAAAGCAGGGAAAGGTTATTTCGAGGATAGGAGGCCA
TCATCTAACATGGATCCATATGTTGTTACTTCCATGATTGCAGACACCACCATTCTCT
GGAAACCATAAgccaccacacacacatgcattgaagtatttgaaagtcattgttgatt
ccgcattagaatttggtcattgttttttctaggatttggatttgtgttattgttatgg
ttcacactttgtttgtttgaatttgaggccttgttataggtttcatatttctttctct
tgttctaagtaaatgtcagaataataatgtaatgggatcctctagagtcgag SEQ ID NO: 6 *Arabidopsis* GS1 coding sequence
Cambia 1201 vector + rbcS3C + *arabidopsis* GS1Bold ATG is
the start site,
AAAAAAGAAAAAAAAAACATATCTTGTTTGTCAGTATGGGAAGTTTGAGATAAGGA
CGAGTGAGGGGTTAAAATTCAGTGGCCATTGATTTTGTAATGCCAAGAACCACAAA
ATCCAATGGTTACCATTCCTGTAAGATGAGGTTTGCTAACTCTTTTTGTCCGTTAGAT
AGGAAGCCTTATCACTATATATACAAGGCGTCCTAATAACCTCTTAGTAACCAATTA
TTTCAGC*ACCATG*TCTCTGCTCTCAGATCTCGTTAACCTCAACCTCACCGAGCCACC
GGGAAAATCATCGCCGAATACATATGGATCGGTGGATCTGGAATGGATATCAGAAG
CAAAGCCAGGACACTACCAGGACCAGTGACTGATCCATCAAAGCTTCCCAAGTGGA
ACTACGACGGATCCAGCACCGGTCAGGCTGCTGGAGAAGACAGTGAAGTCATTCTA
TACCCTCAGGCAATATTCAAGGATCCCTTCAGGAAAGGCAACAACATCCTGGTGATG
TGTGATGCTTACACACCAGCTGGTGATCCTATTCCAACCAACAAGAGGCACAACGCT
GCTAAGATCTTCAGCCACCCCGACGTTGCCAAGGAGGAGCCTTGGTATGGGATTGA
GCAAGAATACACTTTGATGCAAAAGGATGTGAACTGGCCAATTGGTTGGCCTGTTGG
TGGCTACCCTGGCCCTCAGGGACCTTACTACTGTGGTGTGGGAGCTGACAAAGCCAT
TGGTCGTGACATTGTGGATGCTCACTACAAGGCCTGTCTTTACGCCGGTATTGGTATT
TCTGGTATCAATGGAGAAGTCATGCCAGGCCAGTGGGAGTTCCAAGTCGGCCCTGTT
GAGGGTATTAGTTCTGGTGATCAAGTCTGGGTTGCTCGATACCTTCTCGAGAGGATC
ACTGAGATCTCTGGTGTAATTGTCAGCTTCGACCCGAAACCAGTCCCGGGTGACTGG
AATGGAGCTGGAGCTCACTGCAACTACAGCACTAAGACAATGAGAAACGATGGAGG
ATTAGAAGTGATCAAGAAAGCGATAGGGAAGCTTCAGCTGAAACACAAAGAACAC
ATTGCTGCTTACGGTGAAGGAAACGAGCGTCGTCTCACTGGAAAGCACGAAACCGC
AGACATCAACACATTCTCTTGGGGAGTCGCGAACCGTGGAGCGTCAGTGAGAGTGG
GACGTGACACAGAGAAGGAAGGTAAAGGGTACTTCGAAGACAGAAGGCCAGCTTCT
AACATGGATCCTTACGTTGTCACCTCCATGATCGCTGAGACGACCATACTCGGTTGA SEQ ID NO: 7 *Arabidopsis* GS1 amino acid sequence
Vector sequences at N-terminus in italics
*MVDLRNRRTS*MSLLSDLVNLNLTDATGKIIAEYIWIGGSGMDIRSKARTLPGPVTDPSKLP
KWNYDGSSTGQAAGEDSEVILYPQAIFKDPFRKGNNILVMCDAYTPAGDPIPTNKRHNA
AKIFSHPDVAKEEPWYGIEQEYTLMQKDVNWPIGWPVGGYPGPQGPYYCGVGADKAIG
RDIVDAHYKACLYAGIGISGINGEVMPGQWEFQVGPVEGISSGDQVWVARYLLERITEIS
GVIVSFDPKPVPGDWNGAGAHCNYSTKTMRNDGGLEVIKKAIGKLQLKHKEHIAAYGE
GNERRLTGKHETADINTFSWGVANRGASVRVGRDTEKEGKGYFEDRRPASNMDPYVV
TSMIAETTILG SEQ ID NO: 8 Grape GPT coding DNA sequence
Showing Cambia 1305.1 with (3' end of) rbcS3C + *Vitis*
*vinifera* GPT (Grape).
Bold ATG is the start site, parentheses are the cat1 intron
and the underlined
actagt is the spe1 cloning site used to splice in the GPT gene.
AAAAAAGAAAAAAAAAACATATCTTGTTTGTCAGTATGGGAAGTTTGAGATAAGGA
CGAGTGAGGGGTTAAAATTCAGTGGCCATTGATTTTGTAATGCCAAGAACCACAAA
ATCCAATGGTTACCATTCCTGTAAGATGAGGTTTGCTAACTCTTTTTGTCCGTTAGAT
AGGAAGCCTTATCACTATATATACAAGGCGTCCTAATAACCTCTTAGTAACCAATTA
TTTCAGC*CCATGG*TAGATCTGAGG(GTAAATTTCTAGTTTTTCTCCTTCATTTTCTTG
GTTAGGACCCTTTTCTCTTTTTATTTTTTGAGCTTTGATCTTTCTTTAAACTGATCTA
TTTTTTAATTGATTGGTTATGGTGTAAATATTACATAGCTTTAACTGATAATCTGATT
ACTTTATTTCGTGTGTCTATGATGATGATGATAGTTACAG)AACCGACGA*ACTAGT*AT
GCAGCTCTCTCAATGTACCTGGACATTCCCAGAGTTGCTAAAAGACCAGCCTTTTT
AAGGAGGAGTATTGATAGTATTTCGAGTAGAAGTAGGTCCAGCTCCAAGTATCCATC

TABLE OF SEQUENCES:

```
TTTCATGGCGTCCGCATCAACGGTCTCCGCTCCAAATACGGAGGCTGAGCAGACCCA
TAACCCCCCTCAACCTCTACAGGTTGCAAAGCGCTTGGAGAAATTCAAAACAACAA
TCTTTACTCAAATGAGCATGCTTGCCATCAAACATGGAGCAATAAACCTTGGCCAAG
GGTTTCCCAACTTTGATGGTCCTGAGTTTGTCAAAGAAGCAGCAATTCAAGCCATTA
AGGATGGGAAAAACCAATATGCTCGTGGATATGGAGTTCCTGATCTCAACTCTGCTG
TTGCTGATAGATTCAAGAAGGATACAGGACTCGTGGTGGACCCCGAGAAGGAAGTT
ACTGTTACTTCTGGATGTACAGAAGCAATTGCTGCTACTATGCTAGGCTTGATAAAT
CCTGGTGATGAGGTGATCCTCTTTGCTCCATTTTATGATTCCTATGAAGCCACTCTAT
CCATGGCTGGTGCCCAATAAAATCCATCACTTTACGTCCTCCGGATTTTGCTGTGCC
CATGGATGAGCTCAAGTCTGCAATCTCAAAGAATACCCGTGCAATCCTTATAAACAC
TCCCCATAACCCCACAGGAAAGATGTTCACAAGGGAGGAACTGAATGTGATTGCAT
CCCTCTGCATTGAGAATGATGTGTTGGTGTTTACTGATGAAGTTTACGACAAGTTGG
CTTTCGAAATGGATCACATTTCCATGCTTCTCTTCCTGGGATGTACGAGAGGACCG
TGACTATGAATTCCTTAGGGAAAACTTTCTCCCTGACTGGATGGAAGATTGGTTGGA
CAGTAGCTCCCCCACACCTGACATGGGGAGTGAGGCAAGCCCACTCATTCCTCACGT
TTGCTACCTGCACCCCAATGCAATGGGCAGCTGCAACAGCCCTCCGGGCCCCAGACT
CTTACTATGAAGAGCTAAAGAGAGATTACAGTGCAAAGAAGGCAATCCTGGTGGAG
GGATTGAAGGCTGTCGGTTTCAGGGTATACCCATCAAGTGGGACCTATTTTGTGGTG
GTGGATCACACCCCATTTGGGTTGAAAGACGATATTGCGTTTTGTGAGTATCTGATC
AAGGAAGTTGGGGTGGTAGCAATTCCGACAAGCGTTTTCTACTTACACCCAGAAGAT
GGGAAAGAACCTTGTGAGGTTTACCTTCTGTAAAGACGAGGGAACTCTGAGAGCTGC
AGTTGAAAGGATGAAGGAGAAACTGAAGCCTAAACAATAGGGGCACGTGA

SEQ ID NO: 9 Grape GPT amino acid sequence
MVDLRNRRTSMQLSQCTWTFPELLKRPAFLRRSIDSISSRSRSSSKYPSFMASASTVSAPN
TEAEQTHNPPQPLQVAKRLEKFKTTIFTQMSMLAIKHGAINLGQGFPNFDGPEFVKEAAI
QAIKDGKNQYARGYGVPDLNSAVADRFKKDTGLVVDPEKEVTVTSGCTEAIAATMLGL
INPGDEVILFAPFYDSYEATLSMAGAQIKSITLRPPDFAVPMDELKSAISKNTRAILINTPH
NPTGKMFTREELNVIASLCIENDVLVFTDEVYDKLAFEMDHISMASLPGMYERTVTMNS
LGKTFSLTGWKIGWTVAPPHLTWGVRQAHSFLTFATCTPMQWAAATALRAPDSYYEEL
KRDYSAKKAILVEGLKAVGFRVYPSSGTYFVVVDHTPFGLKDDIAFCEYLIKEVGVVAIP
TSVFYLHPEDGKNLVRFTFCKDEGTLRAAVERMKEKLKPKQ SEQ ID NO: 10 Rice GPT DNA coding sequence
Rice GPT codon optimized for E. coli expression; untranslated
sequences shown in lower case
atgtggATGAACCTGGCAGGCTTTCTGGCAACCCCGGCAACCGCAACCGCAACCCGTCA
TGAAATGCCGCTGAACCCGAGCAGCAGCGCGAGCTTTCTGCTGAGCAGCCTGCGTC
GTAGCCTGGTGGCGAGCCTGCGTAAAGCGAGCCCGGCAGCAGCAGCAGCACTGAGC
CCGATGGCAAGCGCAAGCACCGTGGCAGCAGAAAACGGTGCAGCAAAAGCAGCAG
CAGAAAAACAGCAGCAGCAGCCGGTGCAGGTGGCGAAACGTCTGGAAAAATTTAA
AACCACCATTTTTACCCAGATGAGCATGCTGGCGATTAAACATGGCGCGATTAACCT
GGGCCAGGGCTTTCCGAACTTTGATGGCCCGGATTTTGTGAAAGAAGCGGCGATTCA
GGCGATTAACGCGGGCAAAAACCAGTATGCGCGTGGCTATGGCGTGCCGGAACTGA
ACAGCGCGATTGCGGAACGTTTTCTGAAAGATAGCGGCCTGCAGGTGGATCCGGAA
AAAGAAGTGACCGTGACCAGCGGCTGCACCGAAGCGATTGCGGCGACCATTCTGGG
CCTGATTAACCCGGGCGATGAAGTGATTCTGTTTGCGCCGTTTTATGATAGCTATGA
AGCGACCCTGAGCATGGCGGGCGCGAACGTGAAAGCGATTACCCTGCGTCCGCCGG
ATTTTAGCGTGCCGCTGGAAGAACTGAAAGCGGCCGTGAGCAAAAACACCCGTGCG
ATTATGATTAACACCCCGCATAACCCGACCGGCAAAATGTTTACCCGTGAAGAACTG
GAATTTATTGCGACCCTGTGCAAAGAAAACGATGTGCTGCTGTTTGCGGATGAAGTG
TATGATAAACTGGCGTTTGAAGCGGATCATATTAGCATGGCGAGCATTCCGGGCATG
TATGAACGTACCGTGACCATGAACAGCCTGGGCAAAACCTTTAGCCTGACCGGCTG
GAAAATTGGCTGGGCGATTGCGCCGCCGCATCTGACCTGGGGCGTGCGTCAGGCAC
ATAGCTTTCTGACCTTTGCAACCTGCACCCCGATGCAGGCAGCCGCCGCAGCAGCAC
TGCGTGCACCGGATAGCTATTATGAAGAACTGCGTCGTGATTATGGCGCGAAAAAA
GCGCTGCTGGTGAACGGCCTGAAAGATGCGGGCTTTATTGTGTATCCGAGCAGCGGC
ACCTATTTTGTGATGGTGGATCATACCCCGTTTGGCTTTGATAACGATATTGAATTTT
GCGAATATCTGATTCGTGAAGTGGGCGTGGTGGCGATTCCGCCGAGCGTGTTTTATC
TGAACCCGGAAGATGGCAAAAACCTGGTGCGTTTTACCTTTTGCAAAGATGATGAA
ACCCTGCGTGCGGCGGTGGAACGTATGAAAACCAAACTGCGTAAAAAAAAGCTTgcg
gccgcactcgagcaccaccaccaccaccactga SEQ ID NO: 11 Rice GPT amino acid sequence
Includes amino terminal amino acids MW for cloning and His
tag sequences from pet28 vector in italics.
MWMNLAGFLATPATATATRHEMPLNPSSSASFLLSSLRRSLVASLRKASPAAAAALSPM
ASASTVAAENGAAKAAAEKQQQQPVQVAKRLEKFKTTIFTQMSMLAIKHGAINLGQGF
PNFDGPDFVKEAAIQAINAGKNQYARGYGVPELNSAIAERFLKDSGLQVDPEKEVTVTS
GCTEAIAATILGLINPGDEVILFAPFYDSYEATLSMAGANVKAITLRPPDFSVPLEELKAA
VSKNTRAIMINTPHNPTGKMFTREELEFIATLCKENDVLLFADEVYDKLAFEADHISMAS
IPGMYERTVTMNSLGKTFSLTGWKIGWAIAPPHLTWGVRQAHSFLTFATCTPMQAAAA
AALRAPDSYYEELRRDYGAKKALLVNGLKDAGFIVYPSSGTYFVMVDHTPFGFDNDIEF
CEYLIREVGVVAIPPSVFYLNPEDGKNLVRFTFCKDDETLRAAVERMKTKLRKKKLAAA
LEHHHHHH
```

TABLE OF SEQUENCES:

SEQ ID NO: 12 Soybean GPT DNA coding sequence
TOPO 151D WITH SOYBEAN for *E. coli* expression
From starting codon. Vector sequences are italicized
*ATGCATCATCACCATCACCATGGTAAGCCTATCCCTAACCCTCTCCTCGGTCTCGAT
TCTACGGAAAACCTGTATTTTCAGGGAATTGATCCCTTCACCGCGAAACGTCTGGAA*
AAATTTCAGACCACCATTTTTACCCAGATGAGCCTGCTGGCGATTAAACATGGCGCG
ATTAACCTGGGCCAGGGCTTTCCGAACTTTGATGGCCCGGAATTTGTGAAAGAAGCG
GCGATTCAGGCGATTCGTGATGGCAAAAACCAGTATGCGCGTGGCTATGGCGTGCC
GGATCTGAACATTGCGATTGCGGAACGTTTTAAAAAAGATACCGGCCTGGTGGTGG
ATCCGGAAAAAGAAATTACCGTGACCAGCGGCTGCACCGAAGCGATTGCGGCGACC
ATGATTGGCCTGATTAACCCGGGCGATGAAGTGATTATGTTTGCGCCGTTTTATGAT
AGCTATGAAGCGACCCTGAGCATGGCGGGCGCGAAAGTGAAAGGCATTACCCTGCG
TCCGCCGGATTTTGCGGTGCCGCTGGAAGAACTGAAAAGCACCATTAGCAAAACA
CCCGTGCGATTCTGATTAACACCCCGCATAACCCGACCGGCAAAATGTTTACCCGTG
AAGAACTGAACTGCATTGCGAGCCTGTGTGCATTGAAAACGATGTGCTGGTGTTTACCG
ATGAAGTGTATGATAAACTGGCGTTTGATATGGAACATATTAGCATGGCGAGCCTGC
CGGGCATGTTTGAACGTACCGTGACCCTGAACAGCCTGGGCAAAACCTTTAGCCTGA
CCGGCTGGAAAATTGGCTGGGCGATTGCGCCGCCGCATCTGAGCTGGGGCGTGCGT
CAGGCGCATGCGTTTCTGACCTTTGCAACCGCACATCCGTTTCAGTGCGCAGCAGCA
GCAGCACTGCGTGCACCGGATAGCTATTATGTGGAACTGAAACGTGATTATATGGCG
AAACGTGCGATTCTGATTGAAGGCCTGAAAGCGGTGGGCTTTAAAGTGTTTCCGAGC
AGCGGCACCTATTTTGTGGTGGTGGATCATACCCCGTTTGGCCTGGAAAACGATGTG
GCGTTTTGCGAATATCTGGTGAAAGAAGTGGGCGTGGTGGCGATTCCGACCAGCGT
GTTTTATCTGAACCCGGAAGAAGGCAAAAACCTGGTGCGTTTTACCTTTTGCAAAGA
TGAAGAAACCATTCGTAGCGCGGTGGAACGTATGAAAGCGAAACTGCGTAAAGTCG
ACTAA SEQ ID NO: 13 Soybean GPT amino acid sequence
Translated protein product, vector sequences italicized
*MHHHHHHGKPIPNPLLGLDSTENLYFQGIDPFT*AKRLEKFQTTIFTQMSLLAIKHGAINLG
QGFPNFDGPEFVKEAAIQAIRDGKNQYARGYGVPDLNIAIAERFKKDTGLVVDPEKEITV
TSGCTEAIAATMIGLINPGDEVIMFAPFYDSYEATLSMAGAKVKGITLRPPDFAVPLEEL
KSTISKNTRAILINTPHNPTGKMFTREELNCIASLCIENDVLVFTDEVYDKLAFDMEHISM
ASLPGMFERTVTLNSLGKTFSLTGWKIGWAIAPPHLSWGVRQAHAFLTFATAHPFQCAA
AAALRAPDSYYVELKRDYMAKRAILIEGLKAVGFKVFPSSGTYFVVVDHTPFGLENDV
AFCEYLVKEVGVVAIPTSVFYLNPEEGKNLVRFTFCKDEETIRSAVERMKAKLRKVD SEQ ID NO: 14 Barley GPT DNA coding sequence
Coding sequence from start with intron removed
ATGGTAGATCTGAGGAACCGACGA*ACTAG*TATGGCATCCGCCCCCGCCTCCGCCTCC
GCGGCCCTCTCCACCGCCGCCCCCGCCGACAACGGGGCCGCCAAGCCCACGGAGCA
GCGGCCGGTACAGGTGGCTAAGCGATTGGAGAAGTTCAAAACAACCAATTTTCACAC
AGATGAGCATGCTCGCAGTGAAGCATGGAGCAATAAACCTTGGACAGGGGTTTCCC
AATTTTGATGGCCCTGACTTTGTCAAAGATGCTGCTATTGAGGCTATCAAAGCTGGA
AAGAATCAGTATGCAAGAGGATATGGTGTGCCTGAATTGAACTCAGCTGTTGCTGA
GAGATTTCTCAAGGACAGTGGATTGCACATCGATCCTGATAAGGAAGTTACTGTTAC
ATCTGGGTGCACAGAAGCAATAGCTGCAACGATATTGGGTCTGATCAACCCTGGGG
ATGAAGTCATACTGTTTGCTCCATTCTATGATTCTTATGAGGCTACACTGTCCATGGC
TGGTGCGAATGTCAAAGCCATTACACTCCGCCCTCCGGACTTTGCAGTCCCTCTTGA
AGAGCTAAAGGCTGCAGTCTCGAAGAATACCAGAGCAATAATGATTAATACACCTC
ACAACCCTACCGGGAAAATGTTCACAAGGGAGGAACTTGAGTTCATTGCTGATCTCT
GCAAGGAAAATGACGTGTTGCTCTTTGCCGATGAGGTCTACGACAAGCTGGCGTTTG
AGGCGGATCACATATCAATGGCTTCTATTCCTGGCATGTATGAGAGGACCGTCACTA
TGAACTCCCTGGGGAAGACGTTCTCCTTGACCGGATGGAAGATCGGCTGGGCGATA
GCACCACCGCACCTGACATGGGCGTAAGGCAGGCACACTCCTTCCTCACATTCGCC
ACCTCCACGCCGATGCAATCAGCAGCGGCGGCGGCCCTGAGAGCACCGGACAGCTA
CTTTGAGGAGCTGAAGAGGGACTACGGCGCAAAGAAAGCGCTGCTGGTGGACGGGC
TCAAGGCGGCGGGCTTCATCGTCTACCCTTCGAGCGGAACCTACTTCATCATGGTCG
ACCACACCCCGTTCGGGTTCGACAACGACGTCGAGTTCTGCGAGTACTTGATCCGCG
AGGTCGGCGTCGTGGCCATCCCGCCAAGCGTGTTCTACCTGAACCCGGAGGACGGG
AAGAACCTGGTGAGGTTCACCTTCTGCAAGGACGACGACACGCTAAGGGCGGCGGT
GGACAGGATGAAGGCCAAGCTCAGGAAGAAATGA SEQ ID NO: 15 Barley GPT amino acid sequence
Translated sequence from start site (intron removed)
MVDLRNRRTSMASAPASASAALSTAAPADNGAAKPTEQRPVQVAKRLEKFKTTIFTQM
SMLAVKHGAINLGQGFPNFDGPDFVKDAAIEAIKAGKNQYARGYGVPELNSAVAERFL
KDSGLHIDPDKEVTVTSGCTEAIAATILGLINPGDEVILFAPFYDSYEATLSMAGANVKAI
TLRPPDFAVPLEELKAAVSKNTRAIMINTPHNPTGKMFTREELEFIADLCKENDVLLFAD
EVYDKLAFEADHISMASIPGMYERTVTMNSLGKTFSLTGWKIGWAIAPPHLTWGVRQA
HSFLTFATSTPMQSAAAAALRAPDSYFEELKRDYGAKKALLVDGLKAAGFIVYPSSGTY
FIMVDHTPFGFDNDVEFCEYLIREVGVVAIPPSVFYLNPEDGKNLVRFTFCKDDDTLRAA
VDRMKAKLRKK SEQ ID NO: 16 Zebra fish GPT DNA coding sequence
*Danio renio* sequence designed for expression in *E coli*. Bold,
italicized nucleotides added for cloning or from pET28b vector.

TABLE OF SEQUENCES:

*ATGTCC*GTGGCGAAACGTCTGGAAAAATTTAAAACCACCATTTTTACCCAGATGAGC
ATGCTGGCGATTAAACATGGCGCGATTAACCTGGGCCAGGGCTTTCCGAACTTTGAT
GGCCCGGATTTTGTGAAAGAAGCGGCGATTCAGGCGATTCGTGATGGCAACAACCA
GTATGCGCGTGGCTATGGCGTGCCGGATCTGAACATTGCGATTAGCGAACGTTATAA
AAAAGATACCGGCCTGGCGGTGGATCCGGAAAAAGAAATTACCGTGACCAGCGGCT
GCACCGAAGCGATTGCGGCGACCGTGCTGGGCCTGATTAACCCGGGCGATGAAGTG
ATTGTGTTTGCGCCGTTTTATGATAGCTATGAAGCGACCCTGAGCATGGCGGGCGCG
AAAGTGAAAGGCATTACCCTGCGTCCGCCGGATTTTGCGCTGCCGATTGAAGAACTG
AAAAGCACCATTAGCAAAAACACCCGTGCGATTCTGCTGAACACCCCGCATAACCC
GACCGGCAAAATGTTTACCCCGGAAGAACTGAACACCATTGCGAGCCTGTGCATTG
AAAACGATGTGCTGGTGTTTAGCGATGAAGTGTATGATAAACTGGCGTTTGATATGG
AACATATTAGCATTGCGAGCCTGCCGGGCATGTTTGAACGTACCGTGACCATGAACA
GCCTGGGCAAAACCTTTAGCCTGACCGGCTGGAAAATTGGCTGGGCGATTGCGCCG
CCGCATCTGACCTGGGGCGTGCGTCAGGCGCATGCGTTTCTGACCTTTGCAACCAGC
AACCCGATGCAGTGGGCAGCAGCAGTGGCACTGCGTGCACCGGATAGCTATTATAC
CGAACTGAAACGTGATTATATGGCGAAACGTAGCATTCTGGTGGAAGGCCTGAAAG
CGGTGGGCTTTAAAGTGTTTCCGAGCAGCGGCACCTATTTTGTGGTGGTGGATCATA
CCCCGTTTGGCCATGAAACGATATTGCGTTTTGCGAATATCTGGTGAAAGAAGTGG
GCGTGGTGGCGATTCCGACCAGCGTGTTTTATCTGAACCCGGAAGAAGGCAAAAAC
CTGGTGCGTTTTACCTTTTGCAAAGATGAAGGCACCCTGCGTGCGGCGGTGGATCGT
ATGAAAGAAAAACTGCGTAAAGTCGACAA***GCTTGCGGCCGCACTCGAGCACCACCA
CCACCACCACTGA***

SEQ ID NO: 17 Zebra fish GPT amino acid sequence
Amino acid sequence of *Danio renio* cloned and expressed in
*E. coli* (bold, italicized amino acids are added from
vector/cloning and His tag on C-terminus)
*MS*VAKRLEKFKTTIFTQMSMLAIKHGAINLGQGFPNFDGPDFVKEAAIQAIRDGNNQYA
RGYGVPDLNIAISERYKKDTGLAVDPEKEITVTSGCTEAIAATVLGLINPGDEVIVFAPFY
DSYEATLSMAGAKVKGITLRPPDFALPIEELKSTISKNTRAILLNTPHNPTGKMFTPEELN
TIASLCIENDVLVFSDEVYDKLAFDMEHISIASLPGMFERTVTMNSLGKTFSLTGWKIGW
AIAPPHLTWGVRQAHAFLTFATSNPMQWAAAVALRAPDSYYTELKRDYMAKRSILVEG
LKAVGFKVFPSSGTYFVVVDHTPFGHENDIAFCEYLVKEVGVVAIPTSVFYLNPEEGKN
LVRFTFCKDEGTLRAAVDRMKEKLRK*VDKLAAALEHHHHHH*

SEQ ID NO: 18 *Arabidopsis* truncated GPT -30 construct DNA
sequence *Arabidopsis* GPT coding sequence with 30 amino
acids removed from the targeting sequence.
ATGGCCAAAATCCATCGTCCTATCGGAGCCACCATGACCACAGTTTCGACTCAGAAC
GAGTCTACTCAAAAACCCGTCCAGGTGGCGAAGAGATTAGAGAAGTTCAAGACTAC
TATTTTCACTCAAATGAGCATATTGGCAGTTAAACATGGAGCGATCAATTTAGGCCA
AGGCTTTCCCAATTTCGACGGTCCTGATTTTGTTAAAGAAGCTGCGATCCAAGCTAT
TAAAGATGGTAAAAACCAGTATGCTCGTGGATACGGCATTCCTCAGCTCAACTCTGC
TATAGCTGCGCGGTTTCGTGAAGATACGGGTCTTGTTGTTGATCCTGAGAAAGAAGT
TACTGTTACATCTGGTTGCACAGAAGCCATAGCTGCAGCTATGTTGGGTTTAATAAA
CCCTGGTGATGAAGTCATTCTCTTTGCACCGTTTTATGATTCCTATGAAGCAACACTC
TCTATGGCTGGTGCTAAAGTAAAGGGAATCACTTTACGTCCACCGGACTTCTCCATC
CCTTTGGAAGAGCTTAAAGCTGCGGTAACTAACAAGACTCGAGCCATCCTTATGAAC
ACTCCGCACAACCCGACCGGGAAGATGTTCACTAGGGAGGAGCTTGAAACCATTGC
ATCTCTCTGCATTGAAAACGATGTGCTTGTGTTCTCGGATGAAGTATACGATAAGCT
TGCGTTTGAAATGGATCACATTTCTATAGCTTCTCTTCCCGGTATGTATGAAAGAACT
GTGACCATGAATTCCCTGGGAAAGACTTTCTCTTTAACCGGATGGAAGATCGGCTGG
GCGATTGCGCCGCCTCATCTGACTTGGGGAGTTCGACAAGCACACTCTTACCTCACA
TTCGCCACATCAACACCAGCACAATGGGCAGCCGTTGCAGCTCTCAAGGCACCAGA
GTCTTACTTCAAAGAGCTGAAAAGAGATTACAATGTGAAAAAGGAGACTCTGGTTA
AGGGTTTGAAGGAAGTCGGATTTACAGTGTTCCCATCGAGCGGGACTTACTTTGTGG
TTGCTGATCACACTCCATTTGGAATGGAGAACGATGTTGCTTTCTGTGAGTATCTTAT
TGAAGAAGTTGGGGTCGTTGCGATCCCAACGAGCGTCTTTTATCTGAATCCAGAAGA
AGGGAAGAATTTGGTTAGGTTTGCGTTCTGTAAAGACGAAGAGACGTTGCGTGGTG
CAATTGAGAGGATGAAGCAGAAGCTTAAGAGAAAAGTCTGA SEQ ID NO: 19 *Arabidopsis* truncated GPT -30 construct
amino acid sequence
MAKIHRPIGATMTTVSTQNESTQKPVQVAKRLEKFKTTIFTQMSILAVKHGAINLGQGFP
NFDGPDFVKEAAIQAIKDGKNQYARGYGIPQLNSAIAARFREDTGLVVDPEKEVTVTSG
CTEAIAAAMLGLINPGDEVILFAPFYDSYEATLSMAGAKVKGITLRPPDFSIPLEELKAAV
TNKTRAILMNTPHNPTGKMFTREELETIASLCIENDVLVFSDEVYDKLAFEMDHISIASLP
GMYERTVTMNSLGKTFSLTGWKIGWAIAPPHLTWGVRQAHSYLTFATSTPAQWAAVA
ALKAPESYFKELKRDYNVKKETLVKGLKEVGFTVFPSSGTYFVVADHTPFGMENDVAF
CEYLIEEVGVVAIPTSVFYLNPEEGKNLVRFAFCKDEETLRGAIERMKQKLKRKV SEQ ID NO: 20: *Arabidopsis* truncated GPT -45 construct
DNA sequence *Arabidopsis* GPT coding sequence with 45
residues in the targeting sequence removed
ATGGCGACTCAGAACGAGTCTACTCAAAAACCCGTCCAGGTGGCGAAGAGATTAGA
GAAGTTCAAGACTACTATTTTCACTCAAATGAGCATATTGGCAGTTAAACATGGAGC
GATCAATTTAGGCCAAGGCTTTCCCAATTTCGACGGTCCTGATTTTGTTAAAGAAGC -continued

TABLE OF SEQUENCES:

TGCGATCCAAGCTATTAAAGATGGTAAAAACCAGTATGCTCGTGGATACGGCATTCC
TCAGCTCAACTCTGCTATAGCTGCGCGGTTTCGTGAAGATACGGGTCTTGTTGTTGAT
CCTGAGAAGAAGTTACTGTTACATCTGGTTGCACAGAAGCCATAGCTGCAGCTATG
TTGGGTTTAATAAACCCTGGTGATGAAGTCATTCTCTTTGCACCGTTTTATGATTCCT
ATGAAGCAACACTCTCTATGGCTGGTGCTAAAGTAAAAGGAATCACTTTACGTCCAC
CGGACTTCTCCATCCCTTTGGAAGAGCTTAAAGCTGCGGTAACTAACAAGACTCGAG
CCATCCTTATGAACACTCCGCACAACCCGACCGGGAAGATGTTCACTAGGGAGGAG
CTTGAAACCATTGCATCTCTCTGCATTGAAAACGATGTGCTTGTGTTCTCGGATGAA
GTATACGATAAGCTTGCGTTTGAAATGGATCACATTTCTATAGCTTCTCTTCCCGGTA
TGTATGAAAGAACTGTGACCATGAATTCCCTGGGAAAGACTTTCTCTTTAACCGGAT
GGAAGATCGGCTGGGCGATTGCGCCGCCTCATCTGACTTGGGGAGTTCGACAAGCA
CACTCTTACCTCACATTCGCCACATCAACACCAGCACAATGGGCAGCCGTTGCAGCT
CTCAAGGCACCAGAGTCTTACTTCAAAGAGCTGAAAAGAGATTACAATGTGAAAAA
GGAGACTCTGGTTAAGGGTTTGAAGGAAGTCGGATTTACAGTGTTCCCATCGAGCGG
GACTTACTTTGTGGTTGCTGATCACACTCCATTTGGAATGGAAACGATGTTGCTTTC
TGTGAGTATCTTATTGAAGAAGTTGGGGTCGTTGCGATCCCAACGAGCGTCTTTTAT
CTGAATCCAGAAGAAGGGAAGAATTTGGTTAGGTTTGCGTTCTGTAAAGACGAAGA
GACGTTGCGTGGTGCAATTGAGAGGATGAAGCAGAAGCTTAAGAGAAAAGTCTGA

SEQ ID NO: 21: Arabidopsis truncated GPT -45 construct
amino acid sequence
MATQNESTQKPVQVAKRLEKFKTTIFTQMSILAVKHGAINLGQGFPNFDGPDFVKEAAI
QAIKDGKNQYARGYGIPQLNSAIAARFREDTGLVVDPEKEVTVTSGCTEAIAAAMLGLI
NPGDEVILFAPFYDSYEATLSMAGAKVKGITLRPPDFSIPLEELKAAVTNKTRAILMNTP
HNPTGKMFTREELETIASLCIENDVLVFSDEVYDKLAFEMDHISIASLPGMYERTVTMNS
LGKTFSLTGWKIGWAIAPPHLTWGVRQAHSYLTFATSTPAQWAAVAALKAPESYFKEL
KRDYNVKKETLVKGLKEVGFTVFPSSGTYFVVADHTPFGMENDVAFCEYLIEEVGVVAI
PTSVFYLNPEEGKNLVRFAFCKDEETLRGAIERMKQKLKRKV SEQ ID NO: 22: Tomato Rubisco promoter
TOMATO RuBisCo rbcS3C promoter sequence from Kpn1 to Nco1
GGTACCGTTTGAATCCTCCTTAAAGTTTTTCTCTGGAGAAACTGTAGTAATTTTACTT
TGTTGTGTTCCCTTCATCTTTTGAATTAATGGCATTTGTTTTAATACTAATCTGCTTCT
GAAACTTGTAATGTATGTATATCAGTTTCTTATAATTTATCCAAGTAATATCTTCCAT
TCTCTATGCAATTGCCTGCATAAGCTCGACAAAAGAGTACATCAACCCCTCCTCCTC
TGGACTACTCTAGCTAAACTTGAATTTCCCCTTAAGATTATGAAATTGATATATCCTT
AACAAACGACTCCTTCTGTTGGAAAATGTAGTACTTGTCTTTCTTCTTTTGGGTATAT
ATAGTTTATATACACCATACTATGTACAACATCCAAGTAGAGTGAAATGGATACATG
TACAAGACTTATTTGATTGATTGATGACTTGAGTTGCCTTAGGAGTAACAAATTCTT
AGGTCAATAAATCGTTGATTTGAAATTAATCTCTCTGTCTTAGACAGATAGGAATTA
TGACTTCCAATGGTCCAGAAAGCAAAGTTCGCACTGAGGGTATACTTGGAATTGAG
ACTTGCACAGGTCCAGAAACCAAAGTTCCCATCGAGCTCTAAAATCACATCTTTGGA
ATGAAATTCAATTAGAGATAAGTTGCTTCATAGCATAGGTAAAATGGAAGATGTGA
AGTAACCTGCAATAATCAGTGAAATGACATTAATACACTAAATACTTCATATGTAAT
TATCCTTTCCAGGTTAACAATACTCTATAAAGTAAGAATTATCAGAAATGGGCTCAT
CAAACTTTTGTACTATGTATTTCATATAAGGAAGTATAACTATACATAAGTGTATAC
ACAACTTTATTCCTATTTTGTAAAGGTGGAGAGACTGTTTTCGATGGATCTAAAGCA
ATATGTCTATAAAATGCATTGATATAATAATTATCTGAGAAAATCCAGAATTGGCGT
TGGATTATTTCAGCCAAATAGAAGTTTGTACCATACTTGTTGATTCCTTCTAAGTTAA
GGTGAAGTATCATTCATAAACAGTTTTCCCCAAAGTACTACTCACCAAGTTTCCCTTT
GTAGAATTAACAGTTCAAATATATGGCGCAGAAATTACTCTATGCCCAAAACCAAA
CGAGAAAGAAACAAAATACAGGGGTTCAGACTTTATTTTCGTGTTAGGGTGTGTTT
TTTCATGTAATTAATCAAAAAATATTATGACAAAAACATTTATACATATTTTTACTCA
ACACTCTGGGTATCAGGGTGGGTTGTGTTCGACAATCAATATGGAAAGGAAGTATTT
TCCTTATTTTTTTAGTTAATATTTTCAGTTATACCAAACATACCTTGTGATATTATTTT
TAAAAATGAAAAACTCGTCAGAAAGAAAAGCAAAAGCAACAAAAAAATTGCAAG
TATTTTTTAAAAAAGAAAAAAAAACATATCTTGTTTGTCAGTATGGGAAGTTTGAG
ATAAGGACGAGTGAGGGGTTAAAATTCAGTGGCCATTGATTTTGTAATGCCAAGAA
CCACAAAATCCAATGGTTACCATTCCTGTAAGATGAGGTTTGCTAACTCTTTTTGTCC
GTTAGATAGGAAGCCTTATCACTATATATACAAGGCGTCCTAATAACCTCTTAGTAA
CCAATTATTTCAGCACCATGG SEQ ID NO: 23: Bamboo GPT DNA coding sequence
ATGGCCTCCGCGGCCGTCTCCACCGTCGCCACCGCCGCCGACGGCGTCGCGAAGCC
GACGGAGAAGCAGCCGGTACAGGTCGCAAAGCGTTTGGAAAAGTTTAAGACAACAA
TTTTCACACAGATGAGCATGCTTGCCATCAAGCATGGAGCAATAAACCTCGGCCAGG
GCTTTCCGAATTTTGATGGCCCTGACTTTGTGAAAGAAGCTGCTATTCAAGCTATCA
ATGCTGGGAAGAATCAGTATGCAAGAGGATATGGTGTGCCTGAACTGAACTCGGCT
GTTGCTGAAAGGTTCCTGAAGGACAGTGGCTTGCAAGTCGATCCCGAGAAGGAAGT
TACTGTCACATCTGGGTGCACGGAAGCGATAGCTGCAACGATATTGGGTCTTATCAA
CCCTGGCGATGAAGTGATCTTGTTTGCTCCATTCTATGATTCATACGAGGCTACGCTG
TCGATGGCTGGTGCCAATGTAAAAGCCATTACTCTCCGTCCTCCCAGATTTTGCAGTC
CCTCTTGAGGAGCTAAAGGCCACAGTCTCTAAGAACACCAGAGCGATAATGATAAA
CACACCACACAATCCTACTGGGAAATGTTTTCTAGGGAAGAACTTGAATTCATTGC
TACTCTCTGCAAGAAAAATGATGTGTTGCTTTTTGCTGATGAGGTCTATGACAAGTT
GGCATTTGAGGCAGATCATATATCAATGGCTTCTATTCCTGGCATGTATGAGAGGAC
TGTGACTATGAACTCTCTGGGGAAGACATTCTCTCTAACAGGATGGAAGATCGGTTG

TABLE OF SEQUENCES:

```
GGCAATAGCACCACCACACCTGACATGGGGTGTAAGGCAGGCACACTCATTCCTCA
CATTTGCCACCTGCACACCAATGCAATCGGCGGCGGCGGCGGCTCTTAGAGCACCA
GATAGCTACTATGGGGAGCTGAAGAGGGATTACGGTGCAAAGAAAGCGATACTAGT
CGACGGACTCAAGGCTGCAGGTTTTATTGTTTACCCTTCAAGTGGAACATACTTTGT
CATGGTCGATCACACCCCGTTTGGTTTCGACAATGATATTGAGTTCTGCGAGTATTTG
ATCCGCGAAGTCGGTGTTGTCGCCATACCACCAAGCGTATTTTATCTCAACCCTGAG
GATGGGAAGAACTTGGTGAGGTTCACCTTCTGCAAGGATGATGATACGCTGAGAGC
CGCAGTTGAGAGGATGAAGACAAAGCTCAGGAAAAAATGA
```

SEQ ID NO: 24: Bamboo GPT amino acid sequence
```
MASAAVSTVATAADGVAKPTEKQPVQVAKRLEKFKTTIFTQMSMLAIKHGAINLGQGF
PNFDGPDFVKEAAIQAINAGKNQYARGYGVPELNSAVAERFLKDSGLQVDPEKEVTVTS
GCTEAIAATILGLINPGDEVILFAPFYDSYEATLSMAGANVKAITLRPPDFAVPLEELKAT
VSKNTRAIMINTPHNPTGKMFSREELEFIATLCKKNDVLLFADEVYDKLAFEADHISMAS
IPGMYERTVTMNSLGKTFSLTGWKIGWAIAPPHLTWGVRQAHSFLTFATCTPMQSAAA
AALRAPDSYYGELKRDYGAKKAILVDGLKAAGFIVYPSSGTYFVMVDHTPFGFDNDIEF
CEYLIREVGVVAIPPSVFYLNPEDGKNLVRFTFCKDDDTLRAAVERMKTKLRKK
```

SEQ ID NO: 25: 1305.1 + rbcS3C promoter + cat1 intron with rice GPT gene.
Cambia 1305.1 with (3' end of) rbcS3C + rice GPT coding sequence. Underlined ATG is start site, parentheses are the cat1 intron and the underlined actagt is the spe1 cloning site used to splice in the rice gene.
```
AAAAAAGAAAAAAAAAACATATCTTGTTTGTCAGTATGGGAAGTTTGAGATAAGGA
CGAGTGAGGGGTTAAAATTCAGTGGCCATTGATTTTGTAATGCCAAGAACCACAAA
ATCCAATGGTTACCATTCCTGTAAGATGAGGTTTGCTAACTCTTTTTGTCCGTTAGAT
AGGAAGCCTTATCACTATATATACAAGGCGTCCTAATAACCTCTTAGTAACCAATTA
TTTCAGCACCATGGTAGATCTGAGG(GTAAATTTCTAGTTTTTCTCCTTCATTTTCTTG
GTTAGGACCCTTTTCTCTTTTTATTTTTTTGAGCTTTGATCTTTCTTTAAACTGATCTA
TTTTTTAATTGATTGGTTATGGTGTAAATATTACATAGCTTTAACTGATAATCTGATT
ACTTTATTTCGTGTGTCTATGATGATGATAGTTACAG)AACCGACGAACTAGTAT
GAATCTGGCCGGCTTTCTCGCCACGCCCGCGACCGCGACCGCGACGCGGCATGAGA
TGCCGTTAAATCCCTCCTCCTCCGCCTCCTTCCTCCTCTCCTCGCTCCGCCGCTCGCTC
GTCGCGTCGCTCCGGAAGGCCTCGCCGGCGGCGGCCGCGGCGCTCTCCCCCATGGCC
TCCGCGTCCACCGTCGCCGCCGAGAACGGCGCCGCCAAGGCGGCGGCGGAGAAGCA
GCAGCAGCAGCCTGTGCAGGTTGCAAAGCGGTTGGAAAAGTTTAAGACGACCATTT
TCACACAGATGAGTATGCTTGCCATCAAGCATGGAGCAATAAACCTTGGCCAGGGTT
TTCCGAATTTCGATGGCCCTGACTTTGTAAAAGAGGCTGCTATTCAAGCTATCAATG
CTGGGAAGAATCAGTACGCAAGAGGATATGGTGTGCCTGAACTGAACTCAGCTATT
GCTGAAAGATTCCTGAAGGACAGCGGACTGCAAGTCGATCCGGAGAAGGAAGTTAC
TGTCACATCTGGATGCACAGAAGCTATAGCTGCAACAATTTTAGGTCTAATTAATCC
AGGCGATGAAGTGATATTGTTTGCTCCATTCTATGATTCATATGAGGCTACCCTGTC
AATGGCTGGTGCCAACGTAAAAGCCATTACTCTCCGTCCTCCAGATTTTTCAGTCCCT
CTTGAAGAGCTAAAGGCTGCAGTCTCGAAGAACACCAGAGCTATTATGATAAACAC
CCCGCACAATCCTACTGGGAAAATGTTTACAAGGGAAGAACTTGAGTTTATTGCCAC
TCTCTGCAAGGAAAATGATGTGCTGCTTTTTGCTGATGAGGTCTACGACAAGTTAGC
TTTTGAGGCAGATCATATATCAATGGCTTCTATTCCTGGCATGTATGAGAGGACCGT
GACCATGAACTCTCTTGGGAAGACATTCTCTCTTACAGGATGGAAGATCGGTTGGGC
AATCGCACCGCCACACCTGACATGGGGTGTAAGGCAGGCACACTCATTCCTCACGTT
TGCGACCTGCACACCAATGCAAGCAGCTGCAGCTGCAGCTCTGAGAGCACCAGATA
GCTACTATGAGGAACTGAGGAGGGATTATGGAGCTAAGAAGGCATTGCTAGTCAAC
GGACTCAAGGATGCAGGTTTCATTGTCTATCCTTCAAGTGGAACATACTTCGTCATG
GTCGACCACACCCCATTTGGTTTCGACAATGATATTGAGTTCTGCGAGTATTTGATTC
GCGAAGTCGGTGTTGTCGCCATACCACCTAGTGTATTTTATCTCAACCCTGAGGATG
GGAAGAACTTGGTGAGGTTCACCTTTTGCAAGGATGATGAGACGCTGAGAGCCGCG
GTTGAGAGGATGAAGACAAAGCTCAGGAAAAAATGA
```

SEQ D NO: 26: HORDEUM GPT SEQUENCE IN VECTOR
Cambia1305.1 with (3' end of) rbcS3C + hordeum (IDI4) coding sequence. Underlined ATG is start site, parentheses are the cat1 intron and the underlined actagt is the spe1 cloning site used to splice in the hordeum gene.
```
AAAAAAGAAAAAAAAAACATATCTTGTTTGTCAGTATGGGAAGTTTGAGATAAGGA
CGAGTGAGGGGTTAAAATTCAGTGGCCATTGATTTTGTAATGCCAAGAACCACAAA
ATCCAATGGTTACCATTCCTGTAAGATGAGGTTTGCTAACTCTTTTTGTCCGTTAGAT
AGGAAGCCTTATCACTATATATACAAGGCGTCCTAATAACCTCTTAGTAACCAATTA
TTTCAGCACCATGGTAGATCTGAGG(GTAAATTTCTAGTTTTTCTCCTTCATTTTCTTG
GTTAGGACCCTTTTCTCTTTTTATTTTTTTGAGCTTTGATCTTTCTTTAAACTGATCTA
TTTTTTAATTGATTGGTTATGGTGTAAATATTACATAGCTTTAACTGATAATCTGATT
ACTTTATTTCGTGTGTCTATGATGATGATAGTTACAG)AACCGACGAACTAGTAT
GGCATCCGCCCCCGCCTCCGCCTCCGCGGCCCTCTCCACCGCGCCCCGCCGACAA
CGGGGCCGCCAAGCCCACGGAGCAGCGGCCGGTACAGGTGGCTAAGCGATTGGAG
AAGTTCAAAACAACAATTTTCACACAGATGAGCATGCTCGCAGTGAAGCATGGAGC
AATAAACCTTGGACAGGGGTTTCCCAATTTTGATGGCCCTGACTTTGTCAAAGATGC
TGCTATTGAGGCTATCAAAGCTGGAAAGAATCAGTATGCAAGAGGATATGGTGTGC
CTGAATTGAACTCAGCTGTTGCTGAGAGATTTCTCAAGGACAGTGGATTGCACATCG
```

-continued

TABLE OF SEQUENCES:

ATCCTGATAAGGAAGTTACTGTTACATCTGGGTGCACAGAAGCAATAGCTGCAACG
ATATTGGGTCTGATCAACCCTGGGGATGAAGTCATACTGTTTGCTCCATTCTATGATT
CTTATGAGGCTACACTGTCCATGGCTGGTGCGAATGTCAAAGCCATTACACTCCGCC
CTCCGGACTTTGCAGTCCCTCTTGAAGAGCTAAAGGCTGCAGTCTCGAAGAATACCA
GAGCAATAATGATTAATACACCTCACAACCCTACCGGGAAAATGTTCACAAGGGAG
GAACTTGAGTTCATTGCTGATCTCTGCAAGGAAAATGACGTGTTGCTCTTTGCCGAT
GAGGTCTACGACAAGCTGGCGTTTGAGGCGGATCACATATCAATGGCTTCTATTCCT
GGCATGTATGAGAGGACCGTCACTATGAACTCCCTGGGGAAGACGTTCTCCTTGACC
GGATGGAAGATCGGCTGGGCGATAGCACCACCGCACCTGACATGGGCGTAAGGCA
GGCACACTCCTTCCTCACATTCGCCACCTCCACGCCGATGCAATCAGCAGCGGCGGC
GGCCCTGAGAGCACCGGACAGCTACTTTGAGGAGCTGAAGAGGGACTACGGCGCAA
AGAAAGCGCTGCTGGTGGACGGGCTCAAGGCGGCGGGCTTCATCGTCTACCCTTCG
AGCGGAACCTACTTCATCATGGTCGACCACACCCCGTTCGGGTTCGACAACGACGTC
GAGTTCTGCGAGTACTTGATCCGCGAGGTCGGCGTCGTGGCCATCCCGCCAAGCGTG
TTCTACCTGAACCCGGAGGACGGGAAGAACCTGGTGAGGTTCACCTTCTGCAAGGA
CGACGACACGCTAAGGGCGGCGGTGGACAGGATGAAGGCCAAGCTCAGGAAGAAA
TGATTGAGGGGCG*CACGTGTGA*

SEQ ID NO: 27 Expression cassette, Arabidopsis GPT coding
sequence (ATG underlined) under control of CMV 35S promoter
(italics; promoter from Cambia 1201)
*CATGGAGTCAAAGATTCAAATAGAGGACCTAACAGAACTCGCCGTAAAGACTGGCGAACA
GTTCATACAGAGTCTCTTACGACTCAATGACAAGAAGAAAATCTTCGTCAACATGGTGGAG
CACGACACACTTGTCTACTCCAAAAATATCAAAGATACAGTCTCAGAAGACCAAAGGGCAA
TTGAGACTTTTCAACAAAGGGTAATATCCGGAAACCTCCTCGGATTCCATTGCCCAGCTAT
CTGTCACTTTATTGTGAAGATAGTGGAAAAGGAAGGTGGCTCCTACAAATGCCATCATTGC
GATAAAGGAAAGGCCATCGTTGAAGATGCCTCTGCCGACAGTGGTCCCAAAGATGGACCC
CCACCCACGAGGAGCATCGTGGAAAAAGAAGACGTTCCAACCACGTCTTCAAAGCAAGTG
GATTGATGTGATATCTCCACTGACGTAAGGGATGACGCACAATCCCACTATCCTTCGCAAG
ACCCTTCCTCTATATAAGGAAGTTCATTTCATTTGGAGAGAACACGGGGGACTCTTGACCA*
TGTACCTGGACATAAATGGTGTGATGATCAAACAGTTTAGCTTCAAAGCCTCTCTTC
TCCCATTCTCTTCTAATTTCCGACAAAGCTCCGCCAAAATCCATCGTCCTATCGGAGC
CACCATGACCACAGTTTCGACTCAGAACGAGTCTACTCAAAAACCCGTCCAGGTGG
CGAAGAGATTAGAGAAGTTCAAGACTACTATTTTCACTCAAATGAGCATATTGGCAG
TTAAACATGGAGCGATCAATTTAGGCCAAGGCTTTCCCAATTTCGACGGTCCTGATT
TTGTTAAAGAAGCTGCGATCCAAGCTATTAAAGATGGTAAAAACCAGTATGCTCGTG
GATACGGCATTCCTCAGCTCAACTCTGCTATAGCTGCGCGGTTTCGTGAAGATACGG
GTCTTGTTGTTGATCCTGAGAAAGAAGTTACTGTTACATCTGGTTGCACAGAAGCCA
TAGCTGCAGCTATGTTGGGTTTAATAAACCCTGGTGATGAAGTCATTCTCTTTGCACC
GTTTTATGATTCCTATGAAGCAACACTCTCTATGGCTGGTGCTAAAGTAAAAGGAAT
CACTTTACGTCACCGGACTTCTCCATCCCTTTGGAAGAGCTTAAAGCTGCGGTAAC
TAACAAGACTCGAGCCATCCTTATGAACACTCCGCACAACCCGACCGGGAAGATGT
TCACTAGGGAGGAGCTTGAAACCATTGCATCTCTCTGCATTGAAAACGATGTGCTTG
TGTTCTCGGATGAAGTATACGATAAGCTTGCGTTTGAAATGGATCACATTTCTATAG
CTTCTCTTCCCGGTATGTATGAAAGAACTGTGACCATGAATTCCCTGGGAAAGACTT
TCTCTTTAACCGGATGGAAGATCGGCTGGGCGATTGCGCCGCCTCATCTGACTTGGG
GAGTTCGACAAGCACACTCTTACCTCACATTCGCCACATCAACACCAGCACAATGGG
CAGCCGTTGCAGCTCTCAAGGCACCAGAGTCTTACTTCAAAGAGCTGAAAAGAGAT
TACAATGTGAAAAAGGAGACTCTGGTTAAGGGTTTGAAGGAAGTCGGATTTACAGT
GTTCCCATCGAGCGGGACTTACTTTGTGGTTGCTGATCACACTCCATTTGGAATGGA
GAACGATGTTGCTTTCTGTGAGTATCTTATTGAAGAAGTTGGGGTCGTTGCGATCCC
AACGAGCGTCTTTTATCTGAATCCAGAAGAAGGGAAGAATTTGGTTAGGTTTGCGTT
CTGTAAAGACGAAGAGACGTTGCGTGGTGCAATTGAGAGGATGAAGCAGAAGCTTA
AGAGAAAAGTCTGA SEQ ID NO: 28 Cambia p1305.1 with (3' end of) rbcS3C +
Arabidopsis GPT coding sequence.
Underlined ATG is start site, parentheses are the cat1
intron and the underlined actagt is the spe1
cloning site used to splice in the Arabidopsis gene.
AAAAAAGAAAAAAAAAACATATCTTGTTTGTCAGTATGGGAAGTTTGAGATAAGGA
CGAGTGAGGGGTTAAAATTCAGTGGCCATTGATTTTGTAATGCCAAGAACCACAAA
ATCCAATGGTTACCATTCCTGTAAGATGAGGTTTGCTAACTCTTTTTGTCCGTTAGAT
AGGAAGCCTTATCACTATATATACAAGGCGTCCTAATAACCTCTTAGTAACCAATTA
TTTCAGCA*CC**ATGG*TAGATCTGAGG(GTAAATTTCTAGTTTTTCTCCTTCATTTCTTG
GTTAGGACCCTTTTCTCTTTTTATTTTTTTGAGCTTTGATCTTTCTTTAAACTGATCTA
TTTTTTAATTGATTGGTTATGGTGTAAATATTACATAGCTTTAACTGATAATCTGATT
ACTTTATTTCGTGTGTCTATGATGATGATGATAGTTACAG)AACCGACGA*ACTAGT*AT
GTACCTGGACATAAATGGTGTGATGATCAAACAGTTTAGCTTCAAAGCCTCTCTTCT
CCCATTCTCTTCTAATTTCCGACAAAGCTCCGCCAAAATCCATCGTCCTATCGGAGC
CACCATGACCACAGTTTCGACTCAGAACGAGTCTACTCAAAAACCCGTCCAGGTGG
CGAAGAGATTAGAGAAGTTCAAGACTACTATTTTCACTCAAATGAGCATATTGGCAG
TTAAACATGGAGCGATCAATTTAGGCCAAGGCTTTCCCAATTTCGACGGTCCTGATT
TTGTTAAAGAAGCTGCGATCCAAGCTATTAAAGATGGTAAAAACCAGTATGCTCGTG
GATACGGCATTCCTCAGCTCAACTCTGCTATAGCTGCGCGGTTTCGTGAAGATACGG
GTCTTGTTGTTGATCCTGAGAAAGAAGTTACTGTTACATCTGGTTGCACAGAAGCCA
TAGCTGCAGCTATGTTGGGTTTAATAAACCCTGGTGATGAAGTCATTCTCTTTGCACC

TABLE OF SEQUENCES:

```
GTTTTATGATTCCTATGAAGCAACACTCTCTATGGCTGGTGCTAAAGTAAAAGGAAT
CACTTTACGTCCACCGGACTTCTCCATCCCTTTGGAAGAGCTTAAAGCTGCGGTAAC
TAACAAGACTCGAGCCATCCTTATGAACACTCCGCACAACCCGACCGGGAAGATGT
TCACTAGGGAGGAGCTTGAAACCATTGCATCTCTCTGCATTGAAAACGATGTGCTTG
TGTTCTCGGATGAAGTATACGATAAGCTTGCGTTTGAAATGGATCACATTTCTATAG
CTTCTCTTGCCGGTATGTATGAAAGAACTGTGACCATGAATTCCCTGGGAAAGACTT
TCTCTTTAACCGGATGGAAGATCGGCTGGGCGATTGCGCCGCCTCATCTGACTTGGG
GAGTTCGACAAGCACACTCTTACCTCACATTCGCCACATCAACACCAGCACAATGGG
CAGCCGTTGCAGCTCTCAAGGCACCAGAGTCTTACTTCAAAGAGCTGAAAAGAGAT
TACAATGTGAAAAGGAGACTCTGGTTAAGGGTTTGAAGGAAGTCGGATTTACAGT
GTTCCCATCGAGCGGGACTTACTTTGTGGTTGCTGATCACACTCCATTTGGAATGGA
GAACGATGTTGCTTTCTGTGAGTATCTTATTGAAGAAGTTGGGGTCGTTGCGATCCC
AACGAGCGTCTTTTATCTGAATCCAGAAGAAGGGAAGAATTTGGTTAGGTTTGCGTT
CTGTAAAGACGAAGAGACGTTGCGTGGTGCAATTGAGAGGATGAAGCAGAAGCTTA
AGAGAAAAGTCTGA
```

SEQ ID NO: 29 Arabidopsis GPT coding sequence (mature
protein, no targeting sequence)
```
GTGGCGAAGAGATTAGAGAAGTTCAAGACTACTATTTTCACTCAAATGAGCATATTG
GCAGTTAAACATGGAGCGATCAATTTAGGCCAAGGCTTTCCCAATTTCGACGGTCCT
GATTTTGTTAAAGAAGCTGCGATCCAAGCTATTAAAGATGGTAAAAACCAGTATGCT
CGTGGATACGGCATTCCTCAGCTCAACTCTGCTATAGCTGCGCGGTTTCGTGAAGAT
ACGGGTCTTGTTGTTGATCCTGAGAAAGAAGTTACTGTTACATCTGGTTGCACAGAA
GCCATAGCTGCAGCTATGTTGGGTTTAATAAACCCTGGTGATGAAGTCATTCTCTTT
GCACCGTTTTATGATTCCTATGAAGCAACACTCTCTATGGCTGGTGCTAAAGTAAAA
GGAATCACTTTACGTCCACCGGACTTCTCCATCCCTTTGGAAGAGCTTAAAGCTGCG
GTAACTAACAAGACTCGAGCCATCCTTATGAACACTCCGCACAACCCGACCGGGAA
GATGTTCACTAGGGAGGAGCTTGAAACCATTGCATCTCTCTGCATTGAAAACGATGT
GCTTGTGTTCTCGGATGAAGTATACGATAAGCTTGCGTTTGAAATGGATCACATTTC
TATAGCTTCTCTTCCCGGTATGTATGAAAGAACTGTGACCATGAATTCCCTGGGAAA
GACTTTCTCTTTAACCGGATGGAAGATCGGCTGGGCGATTGCGCCGCCTCATCTGAC
TTGGGGAGTTCGACAAGCACACTCTTACCTCACATTCGCCACATCAACACCAGCACA
ATGGGCAGCCGTTGCAGCTCTCAAGGCACCAGAGTCTTACTTCAAAGAGCTGAAAA
GAGATTACAATGTGAAAAGGAGACTCTGGTTAAGGGTTTGAAGGAAGTCGGATTT
ACAGTGTTCCCATCGAGCGGGACTTACTTTGTGGTTGCTGATCACACTCCATTTGGA
ATGGAGAACGATGTTGCTTTCTGTGAGTATCTTATTGAAGAAGTTGGGGTCGTTGCG
ATCCCAACGAGCGTCTTTTATCTGAATCCAGAAGAAGGGAAGAATTTGGTTAGGTTT
GCGTTCTGTAAAGACGAAGAGACGTTGCGTGGTGCAATTGAGAGGATGAAGCAGAA
GCTTAAGAGAAAAGTCTGA
```

SEQ ID NO: 30 Arabidopsis GPT amino acid sequence
(mature protein, no targeting sequence)
```
VAKRLEKFKTTIFTQMSILAVKHGAINLGQGFPNFDGPDFVKEAAIQAIKDGKNQYARG
YGIPQLNSAIAARFREDTGLVVDPEKEVTVTSGCTEAIAAAMLGLINPGDEVILFAPFYDS
YEATLSMAGAKVKGITLRPPDFSIPLEELKAAVTNKTRAILMNTPHNPTGKMFTREELET
IASLCIENDVLVFSDEVYDKLAFEMDHISIASLPGMYERTVTMNSLGKTFSLTGWKIGWA
IAPPHLTWGVRQAHSYLTFATSTPAQWAAVAALKAPESYFKELKRDYNVKKETLVKGL
KEVGFTVFPSSGTYFVVADHTPFGMENDVAFCEYLIEEVGVVAIPTSVFYLNPEEGKNLV
RFAFCKDEETLRGAIERMKQKLKRKV
```

SEQ ID NO: 31 Grape GPT amino acid sequence (mature protein,
no targeting sequence)
```
VAKRLEKFKTTIFTQMSMLAIKHGAINLGQGFPNFDGPEFVKEAAIQAIKDGKNQYARG
YGVPDLNSAVADRFKKDTGLVVDPEKEVTVTSGCTEAIAATMLGLINPGDEVILFAPFY
DSYEATLSMAGAQIKSITLRPPDFAVPMDELKSAISKNTRAILINTPHNPTGKMFTREELN
VIASLCIENDVLVFTDEVYDKLAFEMDHISMASLPGMYERTVTMNSLGKTFSLTGWKIG
WTVAPPHLTWGVRQAHSFLTFATCTPMQWAAATALRAPDSYYEELKRDYSAKKAILV
EGLKAVGFRVYPSSGTYFVVVDHTPFGLKDDIAFCEYLIKEVGVVAIPTSVFYLHPEDGK
NLVRFTFCKDEGTLRAAVERMKEKLKPKQ
```

SEQ ID NO: 32 Rice GPT amino acid sequence (mature protein,
no targeting sequence)
```
VAKRLEKFKTTIFTQMSMLAIKHGAINLGQGFPNFDGPDFVKEAAIQAINAGKNQYARG
YGVPELNSAIAERFLKDSGLQVDPEKEVTVTSGCTEAIAATILGLINPGDEVILFAPFYDS
YEATLSMAGANVKAITLRPPDFSVPLEELKAAVSKNTRAIMINTPHNPTGKMFTREELEF
IATLCKENDVLLFADEVYDKLAFEADHISMASIPGMYERTVTMNSLGKTFSLTGWKIGW
AIAPPHLTWGVRQAHSFLTFATCTPMQAAAAAALRAPDSYYEELRRDYGAKKALLVNG
LKDAGFIVYPSSGTYFVMVDHTPFGFDNDIEFCEYLIREVGVVAIPPSVFYLNPEDGKNL
VRFTFCKDDETLRAAVERMKTLRKK
```

SEQ ID NO: 33 Soybean GPT amino acid sequence (-1 mature
protein, no targeting sequence)
```
AKRLEKFQTTIFTQMSLLAIKHGAINLGQGFPNFDGPEFVKEAAIQAIRDGKNQYARGYG
VPDLNIAIAERFKKDTGLVVDPEKEITVTSGCTEAIAATMIGLINPGDEVIMFAPFYDSYE
ATLSMAGAKVKGITLRPPDFAVPLEELKSTISKNTRAILINTPHNPTGKMFTREELNCIAS
LCIENDVLVFTDEVYDKLAFDMEHISMASLPGMFERTVTLNSLGKTFSLTGWKIGWAIA
PPHLSWGVRQAHAFLTFATAHPFQCAAAAALRAPDSYYVELKRDYMAKRAILIEGLKA
```

TABLE OF SEQUENCES:

VGFKVFPSSGTYFVVVDHTPFGLENDVAFCEYLVKEVGVVAIPTSVFYLNPEEGKNLVR
FTFCKDEETIRSAVERMKAKLRKVD

SEQ ID NO: 34 Barley GPT amino acid sequence (mature protein,
no targeting sequence)
VAKRLEKFKTTIFTQMSMLAVKHGAINLGQGFPNFDGPDFVKDAAIEAIKAGKNQYAR
GYGVPELNSAVAERFLKDSGLHIDPDKEVTVTSGCTEAIAATILGLINPGDEVILFAPFYD
SYEATLSMAGANVKAITLRPPDFAVPLEELKAAVSKNTRAIMINTPHNPTGKMFTREELE
FIADLCKENDVLLFADEVYDKLAFEADHISMASIPGMYERTVTMNSLGKTFSLTGWKIG
WAIAPPHLTWGVRQAHSFLTFATSTPMQSAAAAALRAPDSYFEELKRDYGAKKALLVD
GLKAAGFIVYPSSGTYFIMVDHTPFGFDNDVEFCEYLIREVGVVAIPPSVFYLNPEDGKN
LVRFTFCKDDDTLRAAVDRMKAKLRKK SEQ ID NO: 35 Zebra fish GPT amino acid sequence (mature pro-
tein,
no targeting sequence)
VAKRLEKFKTTIFTQMSMLAIKHGAINLGQGFPNFDGPDFVKEAAIQAIRDGNNQYARG
YGVPDLNIAISERYKKDTGLAVDPEKEITVTSGCTEAIAATVLGLINPGDEVIVFAPFYDS
YEATLSMAGAKVKGITLRPPDFALPIEELKSTISKNTRAILLNTPHNPTGKMFTPEELNTIA
SLCIENDVLVFSDEVYDKLAFDMEHISIASLPGMFERTVTMNSLGKTFSLTGWKIGWAIA
PPHLTWGVRQAHAFLTFATSNPMQWAAAVALRAPDSYYTELKRDYMAKRSILVEGLK
AVGFKVFPSSGTYFVVVDHTPFGHENDIAFCEYLVKEVGVVAIPTSVFYLNPEEGKNLV
RFTFCKDEGTLRAAVDRMKEKLRK SEQ ID NO: 36 Bamboo GPT amino acid sequence (mature protein,
no targeting sequence)
VAKRLEKFKTTIFTQMSMLAIKHGAINLGQGFPNFDGPDFVKEAAIQAINAGKNQYARG
YGVPELNSAVAERFLKDSGLQVDPEKEVTVTSGCTEAIAATILGLINPGDEVILFAPFYDS
YEATLSMAGANVKAITLRPPDFAVPLEELKATVSKNTRAIMINTPHNPTGKMFSREELEF
IATLCKKNDVLLFADEVYDKLAFEADHISMASIPGMYERTVTMNSLGKTFSLTGWKIGW
AIAPPHLTWGVRQAHSFLTFATCTPMQSAAAAALRAPDSYYGELKRDYGAKKAILVDG
LKAAGFIVYPSSGTYFVMVDHTPFGFDNDIEFCEYLIREVGVVAIPPSVFYLNPEDGKNL
VRFTFCKDDDTLRAAVERMKTKLRKK SEQ ID NO: 37 Rice rubisco promoter deposited in NCBI
GenBank: AF143510.1
Pst1 cloning sites in bold; Nco1 cloning site in italics,
cat1 intron and part of Gus plus protein from Cambia 1305.1
vector in bold underline (sequence removed and not translated),
3' terminal Spe1 cloning site in double underline. The
construct also includes a PmlI 1305.1 cloning site
CACGTG (also cuts in rice rbsc promoter), and a Zra1 cloning
site GACGTC, which can be added by PCR to clone into PmlI
site of vector).
CTGCAGCAAAGAAACGTTATTAGTTGGTGCTTTTGGTGGTAGGAATGTAGTTTTCTG
ACAAAGTCAATTACTGAATATAAAAAAAATCTGCACAGCTCTGCGTCAACAGTTGTC
CAAGGGATGCCTCAAAAATCTGTGCAGATTATCAGTCGTCACGCAGAAGCAGAACA
TCATGGTGTGCTAGGTCAGCTTCTTGCATTGGGCCATGAATCCGGTTGGTTGTTAATC
TCTCCTCTCTTATTCTCTTATATTAAGATGCATAACTCTTTTATGTAGTCTAAAAAAA
AATCCAGTGGATCGGATAGTAGTACGTCATGGTGCCATTAGGTACCGTTGAACCTAA
CAGATATTTATGCATGTGTATATATATAGCTATATAGACAAAATTGATGCCGATTAT
AGACCCAAAAGCAATAGGTATATATAATATAATACAGACCACACCACCAAACTAAG
AATCGATCAAATAGACAAGGCATGTCTCCCAAATTGTCTTAAACTATTTCCGTAGGTT
CAGCCGTTCAGGAGTCGAATCAGCCTCTGCCGGCGTTTTCTTTGCACGTACGACGGA
CACACATGGGCATACCATATAGCTGGTCCATGACATTAGGAGAGAGAACGTACGTG
TTGACCTGTAGCTGAGATATAACAAGGTTGATTATAATATCACCAAACATGAAATCA
TCCAAGGATGACCCATAACTATCACTACTATAGTACTGCATCTGGTAAAAGAAATTG
TATAGACTCTATTTCGAGCACTACCACATAACGCCTGCAATGTGACACCCTACCTAT
TCACTAATGTGCCTCTTCCCACACGCTTTCCACCCGTACTGCTCACAGCTTTAAGAAC
CAGAACAAATGAGTAATATTAGTGTCGGTTCATGGCTAAAACCAGCACTGATGTAC
ATGACCACATATGTCAAATGCTGCTTCTAGGCATGACCCCGCTCTTACTAATACCTAC
TCATCGCTAGAAGAATTTTCGGCTGATAAATTTTCAATTTAAGCAAGAGTTATCTGC
GTTGGTTCATAACTCAAACTGATGGCCCCAACCATATTAGTGCAAATTTCACATATG
ATCATAACCTTTTCATATGAAATCGGATCGAGATGAACTTTATATAAACATTGTAGC
TGTCGATGATACCTACAATTTTATAGTTCACAACCTTTTTATTTCAAGTCATTTAAAT
GCCCAAATAGGTGTTTCAAATCTCAGATAGAAATGTTCAAAAGTAAAAAAGGTCCC
TATCATAACATAATTGATATGTAAGTGAGTTGGAAAAAGATAAGTACGTGTGAGAG
AGATCGGGGATCAAATTCTGGTGTAATAATGTATGTATTTCAGTCATAAAAATTGGT
AGCAGTAGTTGGGGCTCTGTATATATACCGGTAAGGATGGGATGGTAGTAGAATAA
TTCTTTTTTTGTTTTTAGTTTTTTCTGGTCCAAAATTTCAAATTTGGATCCCTTACTTG
TACCAACTAATATTAATGAGTGTTGAGGGTAGTAGAGGTGCAACTTTACCATAATCC
CTCTGTTTCAGGTTATAAGACGTTTTGACTTTAAATTTGACCAAGTTTATGCGCAAAT
ATAGTAATATTTATAATACTATATTAGTTTCATTAAATAAATAATTGAATATATTTTC
ATAATAAATTTGTGTTGAGTTCAAAATATTATTAATTTTTTCTACAAACTTGGTCAAA
CTTGAAGCAGTTTGACTTTGACCAAAGTCAAAACGTCTTATAACTTGAAACGGATGG
ATTACTTTTTTTGTGGGGACAAGTTTACAATGTTTAATAAAGCACAATCCATCTTAAT
GTTTTCAAGCTGAATATTGTAAAATTCATGGATAAACCAGCTTCTAAATGTTTAACC
GGGAAAATGTCGAACGACACAAATTAATATTTTTAAGTGATGGGGAGTATTAATTAAG

TABLE OF SEQUENCES:

```
GAGTGACAACTCAACTTTCAATATCGTACTAAACTGTGGGATTTATTTTCTAAAATTT
TATACCCTGCCAATTCACGTGTTGTAGATCTTTTTTTTTCACTAACCGACACCAGGTA
TATCAATTTTATTGAATATAGCAGCAAAAAGAATGTGTTGTACTTGTAAACAAAAAG
CAAACTGTACATAAAAAAAAATGCACTCCTATATAATTAAGCTCATAAAGATGCTTT
GCTTCGTGAGGGCCCAAGTTTTGATGACCTTTTGCTTGATCTCGAAATTAAAATTTAA
GTACTGTTAAGGGAGTTCACACCACCATCAATTTTCAGCCTGAAGAAACAGTTAAAC
AACGACCCCGATGACCAGTCTACTGCTCTCCACATACTAGCTGCATTATTGATCACA
AAACAAAACAAAACGAAATAAAAATCAGCAGCGAGAGTGTGCAGAGAGAGACAAA
GGTGATCTGGCGTGGATATCTCCCCATCCATCCTCACCCGCGCTGCCCATCACTCGC
CGCCGCATACTCCATCATGTGGAGAGAGGAAGACGAGGACCACAGCCAGAGCCCGG
GTCGAGATGCCACCACGGCCACAACCCACGAGCCCGGCGCGACACCACCGCGCGCG
CGTGAGCCAGCCACAAACGCCCGCGGATAGGCGCGCGCACGCCGGCCAATCCTACC
ACATCCCCGGCCTCCGCGGCTCGCGAGCGCCGCTGCCATCCGATCCGCTGAGTTTTG
GCTATTTATACGTACCGCGGGAGCCTGTGTGCAGAGCAGTGCATCTCAAGAAGTACT
CGAGCAAAGAAGGAGAGAGCTTGGTGAGCTGCAGCCATGGTAGATCTGAGGGTAA
ATTTCTAGTTTTTCTCCTTCATTTTCTTGGTTAGGACCCTTTTCTCTTTTTTATTTT
TTTGAGCTTTGATCTTTCTTTAAACTGATCTATTTTTTAATTGATTGGTTATGGT
GTAAATATTACATAGCTTTAACTGATAATCTGATTACTTTATTTCGTGTGTCTAT
GATGATGATGATAGTTACAGAACCGACGAACTAGT

SEQ ID NO: 38 Hordeum GS1 coding sequence
GCGCAGGCGGTTGTGCAGGCGATGCAGTGCCAGGTGGGGGTGAGGGCAGGACGG
CCGTCCCGGCGAGGCAGCCCGCGGGCAGGGTGTGGGGCGTCAGGAGGGCCGCCCGC
GCCACCTCCGGGTTCAAGGTGCTGGCGCTCGGCCCGGAGACCACCGGGGTCATCCA
GAGGATGCAGCAGCTGCTCGACATGGACACCACGCCCTTCACCGACAAGATCATCG
CCGAGTACATCTGGGTTGGAGGATCTGGAATTGACCTCAGAAGCAAATCAAGGACG
ATTTCGAAGCCAGTGGAGGACCCGTCAGAGCTGCCGAAATGGAACTACGACGGATC
GAGCACGGGGCAGGCTCCTGGGGAAGACAGTGAAGTCATCCTATACCCACAGGCCA
TATTCAAGGACCCATTCCGAGGAGGCAACAACATACTGGTTATCTGTGACACCTACA
CACCACAGGGGGAACCCATCCCTACTAACAAACGCCACATGGCTGCACAAATCTTC
AGTGACCCCAAGGTCACTTCACAAGTGCCATGGTTCGGAATCGAACAGGAGTACAC
TCTGATGCAGAGGGATGTGAACTGGCCTCTTGGCTGGCCTGTTGGAGGGTACCCTGG
CCCCCAGGGTCCATACTACTGCGCCGTAGGATCAGACAAGTCATTTGGCCGTGACAT
ATCAGATGCTCACTACAAGGCGTGCCTTTACGCTGGAATTGAAATCAGTGGAACAA
ACGGGGAGGTCATGCCTGGTCAGTGGGAGTACCAGGTTGGACCCAGCGTTGGTATT
GATGCAGGAGACCACATATGGGCTTCCAGATACATTCTCGAGAGAATCACGGAGCA
AGCTGGTGTGGTGCTCACCCTTGACCCAAAACCAATCCAGGGTGACTGGAACGGAG
CTGGCTGCCACACAAACTACAGCACATTGAGCATGCGCGAGGATGGAGGTTTCGAC
GTGATCAAGAAGGCAATCCTGAACCTTTCACTTCGCCATGACTTGCACATAGCCGCA
TATGGTGAAGGAAACGAGCGGAGGTTGACAGGGCTACACGAGACAGCTAGCATATC
AGACTTCTCATGGGGTGTGGCGAACCGTGGCTGCTCTATTCGTGTGGGGCGAGACAC
CGAGGCGAAGGGCAAAGGATACCTGGAGGACCGTCGCCCGGCCTCCAACATGGACC
CGTACACCGTGACGGCGCTGCTGGCCGAGACCACGATCCTGTGGGAGCCGACCCTC
GAGGCGGAGGCCCTCGCTGCCAAGAAGCTGGCGCTGAAGGTATGA SEQ ID NO: 39 Hordeum GS1 amino acid sequence
AQAVVQAMQCQVGVRGRTAVPARQPAGRVWGVRRAARATSGFKVLALGPETTGVIQ
RMQQLLDMDTTPFTDKIIAEYIWVGGSGIDLRSKSRTISKPVEDPSELPKWNYDGSSTGQ
APGEDSEVILYPQAIFKDPFRGGNNILVICDTYTPQGEPIPTNKRHMAAQIFSDPKVTSQV
PWFGIEQEYTLMQRDVNWPLGWPVGGYPGPQGPYYCAVGSDKSFGRDISDAHYKACL
YAGIEISGTNGEVMPGQWEYQVGPSVGIDAGDHIWASRYILERITEQAGVVLTLDPKPIQ
GDWNGAGCHTNYSTLSMREDGGFDVIKKAILNLSRHDLHIAAYGEGNERRLTGLHET
ASISDFSWGVANRGCSIRVGRDTEAKGKGYLEDRRPASNMDPYTVTALLAETTILWEPT
LEAEALAAKKLALKV SEQ ID NO: 40 Expression cassette combining SEQ ID NO: 37
(5') and SEQ ID NO: 38 (3'), encoding the Rice rubisco pro-
moter,
cat1 intron and part of Gus plus protein, and hordeum GS1.
Features shown as in SEQ ID NO: 37. Hordeum GS1 coding
sequence begins after SpeI cloning site (double underline).
CTGCAGCAAAGAAACGTTATTAGTTGGTGCTTTTGGTGGTAGGAATGTAGTTTTCTG
ACAAAGTCAATTACTGAATATAAAAAAAATCTGCACAGCTCTGCGTCAACAGTTGTC
CAAGGGATGCCTCAAAAATCTGTGCAGATTATCAGTCGTCACGCAGAAGCAGAACA
TCATGGTGTGCTAGGTCAGCTTCTTGCATTGGGCCATGAATCCGGTTGGTTGTTAATC
TCTCCTCTCTTATTCTCTTATATTAAGATGCATAACTCTTTTATGTAGTCTAAAAAAA
AATCCAGTGGATCGGATAGTAGTACGTCATGGTGCCATTAGGTACCGTTGAACCTAA
CAGATATTTATGCATGTGTATATATAGCTATATAGACAAAATTGATGCCGATTAT
AGACCCAAAAGCAATAGGTATATATAATATAATACAGACCACACCACCAAACTAAG
AATCGATCAAATAGACAAGGCATGTCTCCAAATTGTCTTAAACTATTTCCGTAGGTT
CAGCCGTTCAGGAGTCGAATCAGCCTCTGCCGGCGTTTTCTTTGCACGTACGACGGA
CACACATGGGCATACCATATAGCTGGTCCATGACATTAGGAGAGAGAACGTACGTG
TTGACCTGTAGCTGAGATATAACAAGGTTGATTATAATATCACCAAACATGAAATCA
TCCAAGGATGACCCATAACTATCACTACTATAGTACTGCATCTGGTAAAAGAAATTG
TATAGACTCTATTTCGAGCACTACCACATAACGCCTGCAATGTGACACCCTACCTAT
TCACTAATGTGCCTCTTCCCACACGCTTTCCACCCGTACTGCTCACAGCTTTAAGAAC
CAGAACAAATGAGTAATATTAGTGTCGGTTCATGGCTAAAACCAGCACTGATGTAC
ATGACCACATATGTCAAATGCTGCTTCTAGGCATGACCCGCTCTTACTAATACCTAC
```

TABLE OF SEQUENCES:

```
TCATCGCTAGAAGAATTTTCGGCTGATAAATTTTCAATTTAAGCAAGAGTTATCTGC
GTTGGTTCATAACTCAAACTGATGGCCCCAACCATATTAGTGCAAATTTCACATATG
ATCATAACCTTTTCATATGAAATCGGATCGAGATGAACTTTATATAAACATTGTAGC
TGTCGATGATACCTACAATTTTATAGTTCACAACCTTTTTATTTCAAGTCATTTAAAT
GCCCAAATAGGTGTTTCAAATCTCAGATAGAAATGTTCAAAAGTAAAAAAGGTCCC
TATCATAACATAATTGATATGTAAGTGAGTTGGAAAAAGATAAGTACGTGTGAGAG
AGATCGGGGATCAAATTCTGGTGTAATAATGTATGTATTTCAGTCATAAAAATTGGT
AGCAGTAGTTGGGGCTCTGTATATATACCGGTAAGGATGGGATGGTAGTAGAATAA
TTCTTTTTTTGTTTTAGTTTTTTCTGGTCCAAAATTTCAAATTTGGATCCCTTACTTG
TACCAACTAATATTAATGAGTGTTGAGGGTAGTAGAGGTGCAACTTTACCATAATCC
CTCTGTTTCAGGTTATAAGACGTTTTGACTTTAAATTTGACCAAGTTTATGCGCAAAT
ATAGTAATATTTATAATACTATATTAGTTTCATTAAATAAATAATTGAATATATTTTC
ATAATAAATTTGTGTTGAGTTCAAAATATTATTAATTTTTTCTACAAACTTGGTCAAA
CTTGAAGCAGTTTGACTTTGACCAAAGTCAAAACGTCTTATAACTTGAAACGGATGG
ATTACTTTTTTTGTGGGGACAAGTTTACAATGTTTAATAAAGCACAATCCATCTTAAT
GTTTTCAAGCTGAATATTGTAAAATTCATGGATAAACCAGCTTCTAAATGTTTAACC
GGGAAAATGTCGAACGACAAATTAATATTTTAAGTGATGGGGAGTATTAATTAAG
GAGTGACAACTCAACTTTCAATATCGTACTAAACTGTGGGATTTATTTTCTAAAATTT
TATACCCTGCCAATTCACGTGTTGTAGATCTTTTTTTTTCACTAACCGACACCAGGTA
TATCAATTTTATTGAATATAGCAGCAAAAAGAATGTGTTGTACTTGTAAACAAAAG
CAAACTGTACATAAAAAAAAATGCACTCCTATATAATTAAGCTCATAAAGATGCTTT
GCTTCGTGAGGGCCCAAGTTTTGATGACCTTTTGCTTGATCTCGAAATTAAAATTTAA
GTACTGTTAAGGGAGTTCACACCACCATCAATTTTCAGCCTGAAGAAACAGTTAAAC
AACGACCCCGATGACCAGTCTACTGCTCTCCACATACTAGCTGCATTATTGATCACA
AAACAAAACAAAACGAAATAAAAATCAGCAGCGAGAGTGTGCAGAGAGAGACAAA
GGTGATCTGGCGTGGATATCTCCCCATCCATCCTCACCCGCGCTGCCCATCACTCGC
CGCCGCATACTCCATCATGTGGAGAGAGGAAGACGAGGACCACAGCCAGAGCCCGG
GTCGAGATGCCACCACGGCCACAACCCACGAGCCCGGCGCGACACCACCGCGCGCG
CGTGAGCCAGCCACAAACGCCCGCGGATAGGCGCGCGCACGCCGGCCAATCCTACC
ACATCCCCGGCCTCCGCGGCTCGCGAGCGCCGCTGCCATCCGATCCGCTGAGTTTTG
GCTATTTATACGTACCGCGGGAGCCTGTGTGCAGAGCAGTGCATCTCAAGAAGTACT
CGAGCAAAGAAGGAGAGCTTGGTGAGCTGCAGCCATGGTAGATCTGAGGGTAAA
TTTCTAGTTTTTCTCCTTCATTTTCTTGGTTAGGACCCTTTTCTCTTTTTATTTTT
TTGAGCTTTGATCTTTCTTTAAACTGATCTATTTTTTAATTGATTGGTTATGGTG
TAAATATTACATAGCTTTAACTGATAATCTGATTACTTTATTTCGTGTGTCTATG
ATGATGATGATAGTTACAGAACCGACGAACTAGTGCGCAGGCGGTTGTGCAGGCG
ATGCAGTGCCAGGTGGGGGTGAGGGGCAGGACGGCCGTCCCGGCGAGGCAGCCG
CGGGCAGGGTGTGGGCGTCAGGAGGGCCGCCCGCGCCACCTCCGGGTTCAAGGTG
CTGGCGCTCGGCCCGGAGACCACCGGGGTCATCCAGAGGATGCAGCAGCTGCTCGA
CATGGACACCACGCCCTTCACCGACAAGATCATCGCCGAGTACATCTGGGTTGGAG
GATCTGGAATTGACCTCAGAAGCAAATCAAGGACGATTTCGAAGCCAGTGGAGGAC
CCGTCAGAGCTGCCGAAATGGAACTACGACGGATCGAGCACGGGGCAGGCTCCTGG
GGAAGACAGTGAAGTCATCCTATACCCACAGGCCATATTCAAGGACCCATTCCGAG
GAGGCAACAACATACTGGTTATCTGTGACACCTACACACCACAGGGGGAACCCATC
CCTACTAACAAACGCCACATGGCTGCACAAATCTTCAGTGACCCCAAGGTCACTTCA
CAAGTGCCATGGTTCGGAATCGAACAGGAGTACACTCTGATGCAGAGGGATGTGAA
CTGGCCTCTTGGCTGGCCTGTTGGAGGGTACCCTGGCCCCCAGGGTCCATACTACTG
CGCCGTAGGATCAGACAAGTCATTTGGCCGTGACATATCAGATGCTCACTACAAGGC
GTGCCTTTACGCTGGAATTGAAATCAGTGGAACAAACGGGGAGGTCATGCCTGGTC
AGTGGGAGTACCAGGTTGGACCCAGCGTTGGTATTGATGCAGGAGACCACATATGG
GCTTCCAGATACATTCTCGAGAGAATCACGGAGCAAGCTGGTGTGGTGCTCACCCTT
GACCCAAAACCAATCCAGGGTGACTGGAACGGAGCTGGCTGCCACACAAACTACAG
CACATTGAGCATGCGCGAGGATGGAGGTTTCGACGTGATCAAGAAGGCAATCCTGA
ACCTTTCACTTCGCCATGACTTGCACATAGCCGCATATGGTGAAGGAAACGAGCGGA
GGTTGACAGGGCTACACGAGACAGCTAGCATATCAGACTTCTCATGGGGTGTGGCG
AACCGTGGCTGCTCTATTCGTGTGGGCGAGACACCGAGGCGAAGGGCAAAGGATA
CCTGGAGGACCGTCGCCCGGCCTCCAACATGGACCCGTACACCGTGACGGCGCTGC
TGGCCGAGACCACGATCCTGTGGGAGCCGACCCTCGAGGCGGAGGCCCTCGCTGCC
AAGAAGCTGGCGCTGAAGGTATGA
```

SEQ ID NO: 41 Amino acid sequence of translation product of SEQ ID NO: 40. Amino-terminal bold residues from Gusplus and SpeI cloning site (intron removed)

MVDLRNRRTSAQAVVQAMQCQVGVRGRTAVPARQPAGRVWGVRRAARATSGFKVL
ALGPETTGVIQRMQQLLDMDTTPFTDKIIAEYIWVGGSGIDLRSKSRTISKPVEDPSELPK
WNYDGSSTGQAPGEDSEVILYPQAIFKDPFRGGNNILVICDTYTPQGEPIPTNKRHMAAQ
IFSDPKVTSQVPWFGIEQEYTLMQRDVNWPLGWPVGGYPGPQGPYYCAVGSDKSFGRD
ISDAHYKACLYAGIEISGTNGEVMPGQWEYQVGPSVGIDAGDHIWASRYILERITEQAG
VVLTLDPKPIQGDWNGAGCHTNYSTLSMREDGGFDVIKKAILNLSLRHDLHIAAYGEGN
ERRLTGLHETASISDFSWGVANRGCSIRVGRDTEAKGKGYLEDRRPASNMDPYTVTALL
AETTILWEPTLEAEALAAKKLALKV

SEQ ID NO: 42 Maize ubi1 promoter: 5' UTR intron shown in italics, TATA box at -30 is
underlined, 5' and 3' PstI cloning sites in bold
CTGCAGTGCAGCGTGACCCGGTCGTGCCCCTCTCTAGAGATAATGAGCATTGCATGT
CTAAGTTATAAAAAATTACCACATATTTTTTTTGTCACACTTGTTTGAAGTGCAGTTT

TABLE OF SEQUENCES:

ATCTATCTTTATACATATATTTAAACTTTACTCTACGAATAATATAATCTATAGTACT
ACAATAATATCAGTGTTTTAGAGAATCATATAAATGAACAGTTAGACATGGTCTAAA
GGACAATTGAGTATTTTGACAACAGGACTCTACAGTTTTATCTTTTTAGTGTGCATGT
GTTCTCCTTTTTTTTGCAAATAGCTTCACCTATATAATACTTCATCCATTTTATTAGT
ACATCCATTTAGGGTTTAGGGTTAATGGTTTTTATAGACTAATTTTTTTAGTACATCT
ATTTTATTCTATTTTAGCCTCTAAATTAAGAAAACTAAAACTCTATTTTAGTTTTTTTA
TTTAATAATTTAGATATAAAAATAGAATAAAATAAAGTGACTAAAAATTAAACAAAT
ACCCTTTAAGAAATTAAAAAAACTAAGGAAACATTTTTCTTGTTTCGAGTAGATAAT
GCCAGCCTGTTAAACGCCGTCGACGAGTCTAACGGACACCAACCAGCGAACCAGCA
GCGTCGCGTCGGGCCAAGCGAAGCAGACGGCACGGCATCTCTGTCGCTGCCTCTGG
ACCCCTCTCGAGAGTTCCGCTCCACCGTTGGACTTGCTCCGCTGTCGGCATCCAGAA
ATTGCGTGGCGGAGCGGCAGACGTGAGCCGGCACGGCAGGCGGCCTCCTCCTCCTC
TCACGGCACGGCAGCTACGGGGGATTCCTTTCCCACCGCTCCTTCGCTTTCCCTTCCT
CGCCCGCCG<u>TAATAAATAGA</u>CACCCCCTCCACACCCTCTTTCCCCAACCTCGTGTTG
TTCGGAGCGCACACACACAACCAGATCTCCCCCAAATCCACCCGTCGGCACCTCC
GCTTCAAGGTACGCCGCTCGTCCTCCCCCCCCCCCCTCTCTACCTTCTCTAGATCGG
CGTTCCGGTCCATGGTTAGGGCCCGGTAGTTCTACTTCTGTTCATGTTTGTGTTAGAT
CCGTGTTTGTGTTAGATCCGTGCTGCTAGCGTTCGTACACGGATGCGACCTGTACGT
CAGACACGTTCTGATTGCTAACTTGCCAGTGTTTCTCTTTGGGGAATCCTGGGATGG
CTCTAGCCGTTCCGCAGACGGGATCGATTTCATGATTTTTTTTGTTTCGTTGCATAGG
GTTTGGTTTGCCCTTTTCCTTTATTTCAATATATGCCGTGCACTTGTTTGTCGGGTCAT
CTTTTCATGCTTTTTTTTGTCTTGGTTGTGATGATGTGGTCTGGTTGGGCGGTCGTTCT
AGATCGGAGTAGAATTCTGTTTCAAACTACCTGGTGGATTTATTAATTTTGGATCTGT
ATGTGTGTGCCATACATATTCATAGTTACGAATTGAAGATGGATGGAAATATCG
ATCTAGGATAGGTATACATGTTGATGCGGGTTTTACTGATGCATATACAGAGATGCT
TTTTGTTCGCTTGGTTGTGATGATGTGGTGTGGTTGGGCGGTCGTTCATTCGTTCTAG
ATCGGAGTAGAATACTGTTTCAAACTACCTGGTGTATTTATTAATTTTGGAACTGTAT
GTGTGTGTCATACATCTTCATAGTTACGAGTTTAAGATGGATGGAAATATCGATCTA
GGATAGGTATACATGTTGATGTGGGTTTTACTGATGCATATACATGATGGCATATGC
AGCATCTATTCATATGCTCTAACCTTGAGTACCTATCTATTATAATAAACAAGTATGT
TTTATAATTATTTTGATCTTGATATACTTGGATGATGGCATATGCAGCAGCTATATGT
GGATTTTTTTAGCCCTGCCTTCATACGCTATTTATTTGCTTGGTACTGTTTCTTTTGTC
GATGCTCACCCTGTTGTTTGGTGTTACTTCTGCAG

SEQ ID NO: 43 Hordeum GPT DNA coding sequence, including
targeting sequence coding domain
ATGGCATCCGCCCCCGCCTCCGCCTCCGCGGCCCTCTCCACCGCCGCCCCCGCCGAC
AACGGGGCCGCCAAGCCCACGGAGCAGCGGCCGGTACAGGTGGCTAAGCGATTGG
AGAAGTTCAAAACAACAATTTTCACACAGATGAGCATGCTCGCAGTGAAGCATGGA
GCAATAAACCTTGGACAGGGGTTTCCCAATTTTGATGGCCCTGACTTTGTCAAAGAT
GCTGCTATTGAGGCTATCAAAGCTGGAAAGAATCAGTATGCAAGAGGATATGGTGT
GCCTGAATTGAACTCAGCTGTTGCTGAGAGATTTCTCAAGGACAGTGGATTGCACAT
CGATCCTGATAAGGAAGTTACTGTTACATCTGGGTGCACAGAAGCAATAGCTGCAA
CGATATTGGGTCTGATCAACCCTGGGGATGAAGTCATACTGTTTGCTCCATTCTATG
ATTCTTATGAGGCTACACTGTCCATGGCTGGTGCGAATGTCAAAGCCATTACACTCC
GCCCTCCGGACTTTGCAGTCCCTCTTGAAGAGCTAAAGGCTGCAGTCTGAAGAATA
CCAGAGCAATAATGATTAATACACCTCACAACCCTACCGGGAAATGTTCACAAGG
GAGGAACTTGAGTTCATTGCTGATCTCTGCAAGGAAAATGACGTGTTGCTCTTTGCC
GATGAGGTCTACGACAAGCTGGCGTTTGAGGCGGATCACATATCAATGGCTTCTATT
CCTGGCATGTATGAGAGGACCGTCACTATGAACTCCCTGGGGAAGACGTTCTCCTTG
ACCGGATGGAAGATCGGCTGGGCGATAGCACCACCGCACCTGACATGGGGCGTAAG
GCAGGCACACTCCTTCCTCACATTCGCCACCTCCACGCCGATGCAATCAGCAGCGGC
GGCGGCCCTGAGAGCACCGGACAGCTACTTTGAGGAGCTGAAGAGGGACTACGGCG
CAAAGAAAGCGCTGCTGGTGGACGGGCTCAAGGCGGCGGGCTTCATCGTCTACCCT
TCGAGCGGAACCTACTTCATCATGGTCGACCACACCCCGTTCGGGTTCGACAACGAC
GTCGAGTTCTGCGAGTACTTGATCCGCGAGGTCGGCGTCGTGGCCATCCCGCCAAGC
GTGTTCTACCTGAACCCGGAGGACGGGAAGAACCTGGTGAGGTTCACCTTCTGCAA
GGACGACGACACGCTAAGGGCGGCGGTGGACAGGATGAAGGCCAAGCTCAGGAAG
AAATGA SEQ ID NO: 44 Hordeum GPT amino acid sequence, including
putative targeting sequence (in italics).
*MASAPASASAALSTAAPADNGAAKPTEQRPVQ*VAKRLEKFKTTIFTQMSMLAVKHGAINLG
QGFPNFDGPDFVKDAAIEAIKAGKNQYARGYGVPELNSAVAERFLKDSGLHIDPDKEVT
VTSGCTEAIAATILGLINPGDEVILFAPFYDSYEATLSMAGANVKAITLRPPDFAVPLEEL
KAAVSKNTRAIMINTPHNPTGKMFTREELEFIADLCKENDVLLFADEVYDKLAFEADHIS
MASIPGMYERTVTMNSLGKTFSLTGWKIGWAIAPPHLTWGVRQAHSFLTFATSTPMQS
AAAAALRAPDSYFEELKRDYGAKKALLVDGLKAAGFIVYPSSGTYFIMVDHTPFGFDN
DVEFCEYLIREVGVVAIPPSVFYLNPEDGKNLVRFTFCKDDDTLRAAVDRMKAKLRKK SEQ ID NO: 45 Tomato rubisco small subunit (rbcS3C)
promoter + *Arabidopsis* GS1 DNA coding sequence;
Ncol/Affillsplice site shown in bold, ATG start of GS1
underlined.
GTTTGAATCCTCCTTAAAGTTTTTCTCTGGAGAAACTGTAGTAATTTTACTTTGTTGT
GTTCCCTTCATCTTTTGAATTAATGGCATTGTTTTAATACTAATCTGCTTCTGAAACT
TGTAATGTATGTATATCAGTTTCTTATAATTTATCCAAGTAATATCTTCCATTCTCTAT

TABLE OF SEQUENCES:

```
GCAATTGCCTGCATAAGCTCGACAAAAGAGTACATCAACCCCTCCTCCTCTGGACTA
CTCTAGCTAAACTTGAATTTCCCCTTAAGATTATGAAATTGATATATCCTTAACAAAC
GACTCCTTCTGTTGGAAAATGTAGTACTTGTCTTTCTTCTTTTGGGTATATATAGTTT
ATATACACCATACTATGTACAACATCCAAGTAGAGTGAAATGGATACATGTACAAG
ACTTATTTGATTGATTGATGACTTGAGTTGCCTTAGGAGTAACAAATTCTTAGGTCA
ATAAATCGTTGATTTGAAATTAATCTCTCTGTCTTAGACAGATAGGAATTATGACTTC
CAATGGTCCAGAAAGCAAAGTTCGCACTGAGGGTATACTTGGAATTGAGACTTGCA
CAGGTCCAGAAACCAAAGTTCCCATCGAGCTCTAAAATCACATCTTTGGAATGAAAT
TCAATTAGAGATAAGTTGCTTCATAGCATAGGTAAAATGGAAGATGTGAAGTAACC
TGCAATAATCAGTGAAATGACATTAATACACTAAATACTTCATATGTAATTATCCTT
TCCAGGTTAACAATACTCTATAAAGTAAGAATTATCAGAAATGGGCTCATCAAACTT
TTGTACTATGTATTTCATATAAGGAAGTATAACTATACATAAGTGTATACACAACTT
TATTCCTATTTTGTAAAGGTGGAGAGACTGTTTTCGATGGATCTAAAGCAATATGTC
TATAAAATGCATTGATATAATAATTATCTGAGAAAATCCAGAATTGGCGTTGGATTA
TTTCAGCCAAATAGAAGTTTGTACCATACTTGTTGATTCCTTCTAAGTTAAGGTGAA
GTATCATTCATAAACAGTTTTCCCCAAAGTACTACTCACCAAGTTTCCCTTTGTAGAA
TTAACAGTTCAAATATATGGCGCAGAAATTACTCTATGCCCAAAACCAAACGAGAA
AGAAACAAAATACAGGGGTTGCAGACTTTATTTTCGTGTTAGGGTGTGTTTTTTCAT
GTAATTAATCAAAAAATATTATGACAAAAACATTTATACATATTTTTACTCAACACT
CTGGGTATCAGGGTGGGTTGTGTTCGACAATCAATATGGAAAGGAAGTATTTTCCTT
ATTTTTTTAGTTAATATTTTCAGTTATACCAAACATACCTTGTGATATTATTTTTAAA
AATGAAAAACTCGTCAGAAAGAAAAAGCAAAGCAACAAAAAAATTGCAAGTATT
TTTTAAAAAAGAAAAAAAAAACATATCTTGTTTGTCAGTATGGGAAGTTTGAGATAA
GGACGAGTGAGGGGTTAAAATTCAGTGGCCATTGATTTTGTAATGCCAAGAACCAC
AAAATCCAATGGTTACCATTCCTGTAAGATGAGGTTTGCTAACTCTTTTTGTCCGTTA
GATAGGAAGCCTTATCACTATATATACAAGGCGTCCTAATAACCTCTTAGTAACCAA
TTATTTCAGCACCATGTCTCTGCTCTCAGATCTCGTTAACCTCAACCTCACCGATGC
CACCGGGAAAATCATCGCCGAATACATATGGATCGGTGGATCTGGAATGGATATCA
GAAGCAAAGCCAGGACACTACCAGGACCAGTGACTGATCCATCAAAGCTTCCCAAG
TGGAACTACGACGGATCCAGCACCGGTCAGGCTGCTGGAGAAGACAGTGAAGTCAT
TCTATACCCTCAGGCAATATTCAAGGATCCCTTCAGGAAAGGCAACAACATCCTGGT
GATGTGTGATGCTTACACACCAGCTGGTGATCCTATTCCAACCAACAAGAGGCACAA
CGCTGCTAAGATCTTCAGCCACCCCGACGTTGCCAAGGAGGAGCCTTGGTATGGGAT
TGAGCAAGAATACACTTTGATGCAAAAGGATGTGAACTGGCCAATTGGTTGGCCTGT
TGGTGGCTACCCTGGCCCTCAGGGACCTTACTACTGTGGTGTGGGAGCTGACAAAGC
CATTGGTCGTGACATTGTGGATGCTCACTACAAGGCCTGTCTTTACGCCGGTATTGG
TATTTCTGGTATCAATGGAGAAGTCATGCCAGGCCAGTGGGAGTTCCAAGTCGGCCC
TGTTGAGGGTATTAGTTCTGGTGATCAAGTCTGGGTTGCTCGATACCTTCTCGAGAG
GATCACTGAGATCTCTGGTGTAATTGTCAGCTTCGACCCGAAACCAGTCCCGGGTGA
CTGGAATGGAGCTGGAGCTCACTGCAACTACAGCACTAAGACAATGAGAAACGATG
GAGGATTAGAAGTGATCAAGAAAGCGATAGGGAAGCTTCAGCTGAAACACAAAGA
ACACATTGCTGCTTACGGTGAAGGAAACGAGCGTCGTCTCACTGGAAAGCACGAAA
CCGCAGACATCAACACATTCTCTTGGGGAGTCGCGAACCGTGGAGCGTCAGTGAGA
GTGGGACGTGACACAGAGAAGGAAGGTAAAGGGTACTTCGAAGACAGAAGGCCAG
CTTCTAACATGGATCCTTACGTTGTCACCTCCATGATCGCTGAGACGACCATACTCG
GTTGA
```

SEQ ID NO: 46 Tomato rubisco small subunit promoter
(rbcS3C) + *Zea Mays* AAT [GPT]
ccatgg is Nco1 cloning site 3' end of promoter into vector
actagt is Spe1 cloning site to insert gene to promoter + intron
ggtacc is Kpn1 cloning site 5' end of promoter to vector
Sequence in double underline is the cat1 intron from
the Cambia 1305.1 vector; first 10 amino
acids are from GUSplus enzyme and cloning sites in 1305.1 vector

```
GGTACCGTTTGAATCCTCCTTAAAGTTTTTCTCTGGAGAAACTGTAGTAATTTTACTT
TGTTGTGTTCCCTTCATCTTTTGAATTAATGGCATTTGTTTTAATACTAATCTGCTTCT
GAAACTTGTAATGTATGTATATCAGTTTCTTATAATTTATCCAAGTAATATCTTCCAT
TCTCTATGCAATTGCCTGCATAAGCTCGACAAAAGAGTACATCAACCCCTCCTCCTC
TGGACTACTCTAGCTAAACTTGAATTTCCCCTTAAGATTATGAAATTGATATATCCTT
AACAAACGACTCCTTCTGTTGGAAAATGTAGTACTTGTCTTTCTTCTTTTGGGTATAT
ATAGTTTATATACACCATACTATGTACAACATCCAAGTAGAGTGAAATGGATACATG
TACAAGACTTATTTGATTGATTGATGACTTGAGTTGCCTTAGGAGTAACAAATTCTT
AGGTCAATAAATCGTTGATTTGAAATTAATCTCTCTGTCTTAGACAGATAGGAATTA
TGACTTCCAATGGTCCAGAAAGCAAAGTTCGCACTGAGGGTATACTTGGAATTGAG
ACTTGCACAGGTCCAGAAACCAAAGTTCCCATCGAGCTCTAAAATCACATCTTTGGA
ATGAAATTCAATTAGAGATAAGTTGCTTCATAGCATAGGTAAAATGGAAGATGTGA
AGTAACCTGCAATAATCAGTGAAATGACATTAATACACTAAATACTTCATATGTAAT
TATCCTTTCCAGGTTAACAATACTCTATAAAGTAAGAATTATCAGAAATGGGCTCAT
CAAACTTTTGTACTATGTATTTCATATAAGGAAGTATAACTATACATAAGTGTATAC
ACAACTTTATTCCTATTTTGTAAAGGTGGAGAGACTGTTTTCGATGGATCTAAAGCA
ATATGTCTATAAAATGCATTGATATAATAATTATCTGAGAAAATCCAGAATTGGCGT
TGGATTATTTCAGCCAAATAGAAGTTTGTACCATACTTGTTGATTCCTTCTAAGTTAA
GGTGAAGTATCATTCATAAACAGTTTTCCCCAAAGTACTACTCACCAAGTTTCCCTTT
GTAGAATTAACAGTTCAAATATATGGCGCAGAAATTACTCTATGCCCAAAACCAAA
CGAGAAAGAAACAAAATACAGGGGTTGCAGACTTTATTTTCGTGTTAGGGTGTGTT
TTTCATGTAATTAATCAAAAAATATTATGACAAAAACATTTATACATATTTTTACTCA
```

TABLE OF SEQUENCES:

ACACTCTGGGTATCAGGGTGGGTTGTGTTCGACAATCAATATGGAAAGGAAGTATTT
TCCTTATTTTTTAGTTAATATTTTCAGTTATACCAAACATACCTTGTGATATTATTTT
TAAAAATGAAAAACTCGTCAGAAAGAAAAAGCAAAAGCAACAAAAAAATTGCAAG
TATTTTTTAAAAAAGAAAAAAAAAAACATATCTTGTTTGTCAGTATGGGAAGTTTGA
GATAAGGACGAGTGAGGGGTTAAAATTCAGTGGCCATTGATTTTGTAATGCCAAGA
ACCACAAAATCCAATGGTTACCATTCCTGTAAGATGAGGTTTGCTAACTCTTTTTGTC
CGTTAGATAGGAAGCCTTATCACTATATATACAAGGCGTCCTAATAACCTCTTAGTA
ACCAATTATTTCAGCA*CCATGG*TAGATCTGAGGGTAAATTTCTAGTTTTTCTCCTTCA
TTTTCTTGGTTAGGACCCTTTTCTCTTTTATTTTTTTGAGCTTTGATCTTTCTTTAAAC
TGATCTATTTTTAATTGATTGGTTATGGTGTAAATATTACATAGCTTTAACTGATAA
<u>TCTGATTACTTTATTTCGTGTGTCTATGATGATGATGATAGTTACAGAA</u>CCGACGA**A
CTAGT**ATGAATCTGGCCGCCTTTTCCTCCACCCTTGCCACGCTCCCCTGGTATGAGA
TGCCATCAATAAATTCCTCCGCAACTTTCTCGTCCTCACTGCTCCGCCGCTCGCTCTG
CGCGTCGCTCCGGACGATCTCCCACATGGCCTCCGCCGCCGCCCCCACCTCCGCGCC
CGTCGCCACCACCGAGAACGGCGCCGCGAAGGCGATAGAGCAGCAGCCCGTGCAG
GTCGCAGAGCGGCTGGAAAAGTTCAAGACAACAATTTTCACTCAGATGAGCATGCT
TGCCATCAAGCATGGAGCAATAAACCTTGGCCAGGGCTTTCCGAATTTTGATGGCCC
AGACTTTGTGAAAGAGGCCGCAATTCAAGCTATCAATGCTGGGAAGAATCAGTACG
CAAGAGGGTTTGGTGTGCCTGAACTGAACTCGGCTATCGCTGAAAGGTTCCTGAAGG
ACAGTGGATTGCAAGTTGACCCTGACAAGGAAGTCACTGTTACATCTGGATGCACTG
AGGCAATAGCTGCAACCATACTAGGTCTGATCAATCCTGGCGACGAGGTGATACTGT
TCGCCCCATTCTACGATTCATACGAGGCTACACTGTCGATGGCCGGTGCCAACGTGA
AGGCCATTACCCTCCGCGCTCCAGATTTCGCGGTCCCGCTTGAGGAGCTGGAGGCTG
CAGTCTCCAAGGACACGAAAGCGATAATGATAAACACGCCGCACAACCCAACCGGG
AAAATGTTCACCAGGGAGGAGCTCGAATCCATCGCCGCCCTCTGCAAGGAAAACGA
CGTTTTGCTGTTCTCAGATGAGGTCTATGACAAGCTGGTGTTTGAGGCTGACCACAT
ATCCATGGCTTCTATCCCGGGCATGTACGAGAGGACGGTGACCATGAACTCTCTGGG
GAAGACGTTCTCTCTTACAGGATGGAAGATCGGGTGGGCAATCGCGCCGCCGCACC
TGACATGGGGCCTCAGGCAGGCGCACTCGTTCCTGACGTTCGCCACCTGCACACCGA
TGCAGGCGGCGGCCGCGGCGGCTCTGAGGGCACCGGACAGCTACTACGACGAGCTG
AAGAGGGACTACAGCGCGAAGAAGGCTATCCTGCTGGAAGGACTCGAAGCCGCAG
GGTTCATCGTCTACCCATCGAGTGGGACATACTACATCATGGTCGACCACACCCCGT
TCGGTTTCGACAGCGACGTAGAGTTCTGCGAGTACTTGATCCGCGAAGTCGGCGTCT
GCGCTATACCGCCCAGCGTGTTCTACCTCGACCCCGAAGAGGGAAAGAAATTGGTG
AGGTTCACCTTCAGCAAGGACGAAGGCACGCTGCGGGCCGCGGTCGAGAGGTTGAA
GGCGAAGCTCAGGAGGAAATGA

SEQ ID NO: 47 Zea mays GPT translation product
(of SEQ ID NO: 46)
Italicized bold amino acids are from gus plus sequence
that remain after the intron is removed.
*MVDLRNRRTS*MNLAAFSSTLATLPWYEMPSINSSATFSSSLLRRSLCASLRTISHMASAA
APTSAPVATTENGAAKAIEQRPVQVAERLEKFKTTIFTQMSMLAIKHGAINLGQGFPNFD
GPDFVKEAAIQAINAGKNQYARGFGVPELNSAIAERFLKDSGLQVDPDKEVTVTSGCTE
AIAATILGLINPGDEVILFAPFYDSYEATLSMAGANVKAITLRAPDFAVPLEELEAAVSKD
TKAIMINTPHNPTGKMFTREELESIAALCKENDVLLFSDEVYDKLVFEADHISMASIPGM
YERTVTMNSLGKTFSLTGWKIGWAIAPPHLTWGLRQAHSFLTFATCTPMQAAAAAALR
APDSYYDELKRDYSAKKAILLEGLEAAGFIVYPSSGTYYIMVDHTPFGFDSDVEFCEYLI
REVGVCAIPPSVFYLDPEEGKKLVRFTFSKDEGTLRAAVERLKAKLRRK- SEQ ID NO: 48 Chlorella GPT amino acid sequence
MAAAAAGGDGPSAARRFNSTFSSLPTTIFEQMSLLAAKHQSTNLGQGFPDNELEGPESM
KKVMISLYEHSNQYPPLMGLPELRQAVAAHSARHAGIPVDWQAETLVTVGATEALAAA
FLGLLDAGDEVIFFEPLYDSYVPMARRAGAIPRIVQLYPPAWSIDAAELEAAFSPQTKLL
VLNTPHNPTGKVFGAEELQLIADLCQKHDCLCLLLDEVYEHLVFPGTRHTSLQSLPGMRE
RCLRVGWLSGPHDLLAAVTKAHQFLIFTVPSALQRAVAYGLEQEEAFCCGLGAALSKK
RQLLEGQLAEIGFAVLPAQGTYFLVADFAGLLPAGSSEDDVQFCHRLTVEAGVTLIPVSA
FYADRAATPRTLVRFVFCKTDEKLNTACGKLRTYFGRQ

What is claimed is:

1. A transgenic alga comprising a plant-derived or algal-derived glutamine phenylpyruvate transaminase (GPT) transgene and a glutamine synthetase (GS) transgene, wherein each of said GPT transgene and said GS transgene is operably linked to a promoter, wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 36, SEQ ID NO: 44, SEQ ID NO: 47, and 48.

2. The transgenic alga according to claim 1, wherein the alga is a green alga.

3. The transgenic alga according to claim 2, wherein the green alga is a *Chlorella* species.

4. The transgenic alga according to claim 1, wherein the GPT transgene is a plant-derived GPT.

5. The transgenic alga according to claim 1, wherein the GPT is an algal-derived GPT.

6. The transgenic alga according to claim 1, wherein the GS transgene encodes a polypeptide having an amino acid sequence selected from the group consisting of: SEQ ID NO: 4, SEQ ID NO: 7, and SEQ ID NO: 39.

7. The transgenic alga according to any of claims 6, wherein the GPT and GS transgenes are incorporated into the genome of the alga.

8. A progeny of any generation of the transgenic alga of claim 7, wherein said progeny comprises said GPT transgene and said GS transgene.

9. A method for increasing growth characteristics of an alga relative to an wild type or progenitor alga of the same species, comprising:
 (a) introducing a plant-derived or algal-derived GPT transgene into the alga wherein the GPT transgene encodes a polypeptide having an amino acid sequence selected from the group consisting of: SEQ ID NO: 2, SEQ ID NO: 9, SEQ ID NO: 15, SEQ ID NO: 19, SEQ ID NO: 21, SEQ ID NO 24, SEQ ID NO: 30, SEQ ID NO:31, SEQ ID NO: 32, SEQ ID NO: 33, SEQ ID NO: 34, SEQ ID NO: 36, SEQ ID NO: 44, SEQ ID NO: 47, and 48;
 (b) introducing a GS trans gene into the alga or a progeny of the alga;

(c) expressing the GPT transgene and the GS transgene in the alga or the progeny of the alga; and,
(d) selecting an alga having an increased growth characteristic relative to an alga of the same species that does not comprise the GPT transgene or the GS transgene.

10. The method according to claim 9, wherein the increased growth characteristic is selected from the group consisting of: faster growth rate, increased chlorophyll production, increased ribulose bisphosphate carboxylase (RUBISCO) level, increased nitrogen use efficiency, increased biomass yield, increased GPT activity, increased GS activity, increased 2-oxoglutaramate levels, and/or increased tolerance to salt or saline conditions.

* * * * *

SEQUENCE LISTING

<160> NUMBER OF SEQ ID NOS: 48

<210> SEQ ID NO 1
<211> LENGTH: 1323
<212> TYPE: DNA
<213> ORGANISM: Arabidopsis thaliana

<400> SEQUENCE: 1
atgtacctgg acataaatgg tgtgatgatc aaacagttta gcttcaaagc ctctcttctc        60
ccattctctt ctaatttccg acaaagctcc gccaaaatcc atcgtcctat cggagccacc       120

```
atgaccacag tttcgactca gaacgagtct actcaaaaac ccgtccaggt ggcgaagaga       180
ttagagaagt tcaagactac tattttcact caaatgagca tattggcagt taaacatgga       240
gcgatcaatt taggccaagg cttccccaat ttcgacggtc ctgattttgt taaagaagct       300
gcgatccaag ctattaaaga tggtaaaaac cagtatgctc gtggatacgg cattcctcag       360
ctcaactctg ctatagctgc gcggtttcgt gaagatacgg tcttgttgt tgatcctgag        420 aaagaagtta ctgttacatc tggttgcaca gaagccatag ctgcagctat gttgggttta       480
ataaaccctg gtgatgaagt cattctcttt gcaccgtttt atgattccta tgaagcaaca       540
ctctctatgg ctggtgctaa agtaaaagga atcactttac gtccaccgga cttctccatc       600
cctttggaag agcttaaagc tgcggtaact aacaagactc gagccatcct tatgaacact       660
ccgcacaacc cgaccgggaa gatgttcact agggaggagc ttgaaaccat gcatctctc        720 tgcattgaaa acgatgtgct tgtgttctcg gatgaagtat acgataagct tgcgtttgaa       780
atggatcaca tttctatagc ttctcttccc ggtatgtatg aaagaactgt gaccatgaat       840
tccctgggaa agactttctc tttaaccgga tggaagatcg gctgggcgat tgcgccgcct       900
catctgactt ggggagttcg acaagcacac tcttacctca cattcgccac atcaacacca       960
gcacaatggg cagccgttgc agctctcaag gcaccagagt cttacttcaa agagctgaaa      1020
agagattaca atgtgaaaaa ggagactctg gttaagggtt tgaaggaagt cggatttaca      1080
gtgttcccat cgagcgggac ttactttgtg ttgctgatc acactccatt tggaatggag       1140
aacgatgttg ctttctgtga gtatcttatt gaagaagttg gggtcgttgc gatcccaacg      1200
agcgtctttt atctgaatcc agaagaaggg aagaatttgg ttaggtttgc gttctgtaaa      1260
gacgaagaga cgttgcgtgg tgcaattgag aggatgaagc agaagcttaa gagaaaagtc      1320
tga                                                                    1323
```

<210> SEQ ID NO 2
<211> LENGTH: 440
<212> TYPE: PRT
<213> ORGANISM: Arabidopsis thaliana

<400> SEQUENCE: 2

```
Met Tyr Leu Asp Ile Asn Gly Val Met Ile Lys Gln Phe Ser Phe Lys
  1               5                  10                  15

Ala Ser Leu Leu Pro Phe Ser Ser Asn Phe Arg Gln Ser Ser Ala Lys
                 20                  25                  30

Ile His Arg Pro Ile Gly Ala Thr Met Thr Thr Val Ser Thr Gln Asn
             35                  40                  45

Glu Ser Thr Gln Lys Pro Val Gln Val Ala Lys Arg Leu Glu Lys Phe
         50                  55                  60

Lys Thr Thr Ile Phe Thr Gln Met Ser Ile Leu Ala Val Lys His Gly
 65                  70                  75                  80

Ala Ile Asn Leu Gly Gln Gly Phe Pro Asn Phe Asp Gly Pro Asp Phe
                 85                  90                  95

Val Lys Glu Ala Ala Ile Gln Ala Ile Lys Asp Gly Lys Asn Gln Tyr
                100                 105                 110

Ala Arg Gly Tyr Gly Ile Pro Gln Leu Asn Ser Ala Ile Ala Ala Arg
            115                 120                 125

Phe Arg Glu Asp Thr Gly Leu Val Val Asp Pro Glu Lys Glu Val Thr
        130                 135                 140

Val Thr Ser Gly Cys Thr Glu Ala Ile Ala Ala Ala Met Leu Gly Leu
```

```
            145                 150                 155                 160
    Ile Asn Pro Gly Asp Glu Val Ile Leu Phe Ala Pro Phe Tyr Asp Ser
                    165                 170                 175

Tyr Glu Ala Thr Leu Ser Met Ala Gly Ala Lys Val Lys Gly Ile Thr
                180                 185                 190

Leu Arg Pro Asp Phe Ser Ile Pro Leu Glu Glu Leu Lys Ala Ala
                195                 200                 205

Val Thr Asn Lys Thr Arg Ala Ile Leu Met Asn Thr Pro His Asn Pro
        210                 215                 220

Thr Gly Lys Met Phe Thr Arg Glu Glu Leu Glu Thr Ile Ala Ser Leu
    225                 230                 235                 240

Cys Ile Glu Asn Asp Val Leu Val Phe Ser Asp Glu Val Tyr Asp Lys
                    245                 250                 255

Leu Ala Phe Glu Met Asp His Ile Ser Ile Ala Ser Leu Pro Gly Met
                260                 265                 270

Tyr Glu Arg Thr Val Thr Met Asn Ser Leu Gly Lys Thr Phe Ser Leu
                275                 280                 285

Thr Gly Trp Lys Ile Gly Trp Ala Ile Ala Pro Pro His Leu Thr Trp
    290                 295                 300

Gly Val Arg Gln Ala His Ser Tyr Leu Thr Phe Ala Thr Ser Thr Pro
    305                 310                 315                 320

Ala Gln Trp Ala Ala Val Ala Ala Leu Lys Ala Pro Glu Ser Tyr Phe
                    325                 330                 335

Lys Glu Leu Lys Arg Asp Tyr Asn Val Lys Glu Thr Leu Val Lys
                340                 345                 350

Gly Leu Lys Glu Val Gly Phe Thr Val Phe Pro Ser Ser Gly Thr Tyr
                355                 360                 365

Phe Val Val Ala Asp His Thr Pro Phe Gly Met Glu Asn Asp Val Ala
                370                 375                 380

Phe Cys Glu Tyr Leu Ile Glu Glu Val Gly Val Val Ala Ile Pro Thr
    385                 390                 395                 400

Ser Val Phe Tyr Leu Asn Pro Glu Glu Gly Lys Asn Leu Val Arg Phe
                    405                 410                 415

Ala Phe Cys Lys Asp Glu Glu Thr Leu Arg Gly Ala Ile Glu Arg Met
                420                 425                 430

Lys Gln Lys Leu Lys Arg Lys Val
                435                 440

<210> SEQ ID NO 3
<211> LENGTH: 1374
<212> TYPE: DNA
<213> ORGANISM: Medicago sativa

<400> SEQUENCE: 3
atttccgttt tcgttttcat ttgattcatt gaatcaaatc gaatcgaatc tttaggattc      60
aatacagatt ccttagattt tactaagttt gaaaccaaaa ccaaaacatg tctctccttt     120
cagatcttat caaccttgac ctctccgaaa ccaccgagaa atcatcgcc gaatacatat      180 ggattggtgg atctggtttg gacttgagga gcaaagcaag gactctacca ggaccagtta     240 ctgaccctttc acagcttccc aagtggaact atgatggttc agcacaggt caagctcctg     300 gagaagatag tgaagttatt atctacccac aagccatttt caaggaccca tttagaaggg     360
gtaacaatat cttggttatg tgtgatgcat acactccagc tggagagccc attcccacca     420
acaagagaca tgcagctgcc aagattttca gccatcctga tgttgttgct gaagtaccat     480
```

-continued

```
ggtatggtat tgagcaagaa tacaccttgt tgcagaaaga catcaattgg cctcttggtt      540
ggccagttgg tggttttcct ggacctcagg gaccatacta ttgtggagct ggtgctgaca      600
aggcatttgg ccgtgacatt gttgactcac attacaaagc ctgtctttat gccggcatca      660
acatcagtgg aatcaatggt gaagtgatgc ctggtcaatg gaattccaa gttggtccct       720 cagttggtat ctctgctggt gatgagatat gggttgctcg ttacattttg gagaggatca      780
ctgaggttgc tggtgtggtg ctttccttt g acccaaaacc aattaagggt gattggaatg     840
gtgctggtgc tcacacaaat tacagcacca agtctatgag agaagatggt ggctatgaag      900
tcatcttgaa agcaattgag aagcttggga agaagcacaa ggagcacatt gctgcttatg      960
gagaaggcaa cgagcgtaga ttgacagggc gacatgagac agctgacatt aacaccttct     1020
tatggggtgt tgcaaaccgt ggtgcgtcga ttagagttgg aagggacaca gagaaagcag     1080
ggaaaggtta tttcgaggat aggaggccat catctaacat ggatccatat gttgttactt     1140
ccatgattgc agacaccacc attctctgga aaccataagc caccacacac acatgcattg     1200
aagtatttga aagtcattgt tgattccgca ttagaatttg gtcattgttt tttctaggat     1260
ttggatttgt gttattgtta tggttcacac tttgtttgtt tgaatttgag gccttgttat     1320
aggtttcata tttctttctc ttgttctaag taaatgtcag aataataatg taat            1374
```

<210> SEQ ID NO 4
<211> LENGTH: 356
<212> TYPE: PRT
<213> ORGANISM: Medicago sativa

<400> SEQUENCE: 4

Met Ser Leu Leu Ser Asp Leu Ile Asn Leu Asp Leu Ser Glu Thr Thr
1               5                   10                  15

Glu Lys Ile Ile Ala Glu Tyr Ile Trp Ile Gly Gly Ser Gly Leu Asp
            20                  25                  30

Leu Arg Ser Lys Ala Arg Thr Leu Pro Gly Pro Val Thr Asp Pro Ser
        35                  40                  45

Gln Leu Pro Lys Trp Asn Tyr Asp Gly Ser Ser Thr Gly Gln Ala Pro
    50                  55                  60

Gly Glu Asp Ser Glu Val Ile Ile Tyr Pro Gln Ala Ile Phe Lys Asp
65                  70                  75                  80

Pro Phe Arg Arg Gly Asn Asn Ile Leu Val Met Cys Asp Ala Tyr Thr
                85                  90                  95

Pro Ala Gly Glu Pro Ile Pro Thr Asn Lys Arg His Ala Ala Ala Lys
            100                 105                 110

Ile Phe Ser His Pro Asp Val Val Ala Glu Val Pro Trp Tyr Gly Ile
        115                 120                 125

Glu Gln Glu Tyr Thr Leu Leu Gln Lys Asp Ile Asn Trp Pro Leu Gly
    130                 135                 140

Trp Pro Val Gly Gly Phe Pro Gly Pro Gln Gly Pro Tyr Tyr Cys Gly
145                 150                 155                 160

Ala Gly Ala Asp Lys Ala Phe Gly Arg Asp Ile Val Asp Ser His Tyr
                165                 170                 175

Lys Ala Cys Leu Tyr Ala Gly Ile Asn Ile Ser Gly Ile Asn Gly Glu
            180                 185                 190

Val Met Pro Gly Gln Trp Glu Phe Gln Val Gly Pro Ser Val Gly Ile
        195                 200                 205

Ser Ala Gly Asp Glu Ile Trp Val Ala Arg Tyr Ile Leu Glu Arg Ile

```
                    210                 215                 220
Thr Glu Val Ala Gly Val Val Leu Ser Phe Asp Pro Lys Pro Ile Lys
225                 230                 235                 240

Gly Asp Trp Asn Gly Ala Gly Ala His Thr Asn Tyr Ser Thr Lys Ser
                245                 250                 255

Met Arg Glu Asp Gly Gly Tyr Glu Val Ile Leu Lys Ala Ile Glu Lys
            260                 265                 270

Leu Gly Lys Lys His Lys Glu His Ile Ala Ala Tyr Gly Glu Gly Asn
        275                 280                 285

Glu Arg Arg Leu Thr Gly Arg His Glu Thr Ala Asp Ile Asn Thr Phe
    290                 295                 300

Leu Trp Gly Val Ala Asn Arg Gly Ala Ser Ile Arg Val Gly Arg Asp
305                 310                 315                 320

Thr Glu Lys Ala Gly Lys Gly Tyr Phe Glu Asp Arg Arg Pro Ser Ser
                325                 330                 335

Asn Met Asp Pro Tyr Val Val Thr Ser Met Ile Ala Asp Thr Thr Ile
            340                 345                 350

Leu Trp Lys Pro
        355

<210> SEQ ID NO 5
<211> LENGTH: 1419
<212> TYPE: DNA
<213> ORGANISM: Medicago sativa

<400> SEQUENCE: 5
atcgatgaat tcgagctcgg tacccatttc cgttttcgtt ttcatttgat tcattgaatc      60
aaatcgaatc gaatctttag gattcaatac agattcctta gattttacta agtttgaaac    120
caaaaccaaa acatgtctct cctttcagat cttatcaacc ttgacctctc cgaaaccacc    180
gagaaaatca tcgccgaata catatggatt ggtggatctg gtttggactt gaggagcaaa    240
gcaaggactc taccaggacc agttactgac ccttcacagc ttcccaagtg aactatgat     300 ggttccagca caggtcaagc tcctggagaa gatagtgaag ttattatcta cccacaagcc    360 atttcaagg acccatttag aagggtaac aatatcttgg ttatgtgtga tgcatacact     420
ccagctggag agcccattcc caccaacaag agacatgcag ctgccaagat tttcagccat    480
cctgatgttg ttgctgaagt accatggtat ggtattgagc aagaatacac cttgttgcag    540
aaagacatca attggcctct tggttggcca gttggtggtt ttcctggacc tcagggacca    600
tactattgtg gagctggtgc tgacaaggca tttggccgtg acattgttga ctcacattac    660
aaagcctgtc tttatgccgg catcaacatc agtggaatca atggtgaagt gatgcctggt    720
caatgggaat tccaagttgg tccctcagtt ggtatctctg ctggtgatga gatatgggtt    780
gctcgttaca ttttggagag atcactgag gttgctggtg tggtgctttc ctttgaccca    840
aaaccaatta agggtgattg gaatggtgct ggtgctcaca caaattacag caccaagtct    900
atgagagaag atggtggcta tgaagtcatc ttgaaagcaa ttgagaagct tgggaagaag    960
cacaaggagc acattgctgc ttatggagaa ggcaacgagc gtagattgac agggcgacat   1020
gagacagctg acattaacac cttcttatgg ggtgttgcaa accgtggtgc gtcgattaga   1080
gttggaaggg acacagagaa agcagggaaa ggttatttcg aggataggag gccatcatct   1140
aacatggatc catatgttgt tacttccatg attgcagaca ccaccattct ctggaaacca   1200
taagccacca cacacacatg cattgaagta tttgaaagtc attgttgatt ccgcattaga   1260
```

```
atttggtcat tgttttttct aggatttgga tttgtgttat tgttatggtt cacactttgt    1320
ttgtttgaat ttgaggcctt gttataggtt tcatatttct ttctcttgtt ctaagtaaat    1380
gtcagaataa taatgtaatg gggatcctct agagtcgag                           1419

<210> SEQ ID NO 6
<211> LENGTH: 1302
<212> TYPE: DNA
<213> ORGANISM: Artificial Sequence
<220> FEATURE:
<223> OTHER INFORMATION: Synthetic plasmid vector sequence

<400> SEQUENCE: 6
aaaaaagaaa aaaaaaacat atcttgtttg tcagtatggg aagtttgaga taaggacgag      60
tgaggggtta aaattcagtg gccattgatt ttgtaatgcc aagaaccaca aaatccaatg     120
gttaccattc ctgtaagatg aggtttgcta actcttttg tccgttagat aggaagcctt     180
atcactatat atacaaggcg tcctaataac ctcttagtaa ccaattattt cagcaccatg     240
tctctgctct cagatctcgt taacctcaac ctcaccgatg ccaccgggaa aatcatcgcc     300
gaatacatat ggatcggtgg atctggaatg atatcagaa gcaaagccag gacactacca     360
ggaccagtga ctgatccatc aaagcttccc aagtggaact acgacggatc cagcaccggt     420
caggctgctg agaagacag tgaagtcatt ctatacctc aggcaatatt caaggatccc     480
ttcaggaaag gcaacaacat cctggtgatg tgtgatgctt acacaccagc tggtgatcct     540
attccaacca acaagaggca aacgctgct aagatcttca gccaccccga cgttgccaag     600
gaggagcctt ggtatgggat tgagcaagaa tacactttga tgcaaaagga tgtgaactgg     660
ccaattggtt ggcctgttgg tggctaccct ggccctcagg gaccttacta ctgtggtgtg     720
ggagctgaca aagccattgg tcgtgacatt gtggatgctc actacaaggc ctgtctttac     780
gccggtattg gtatttctgg tatcaatgga gaagtcatgc caggccagtg ggagttccaa     840
gtcggccctg ttgagggtat tagttctggt gatcaagtct gggttgctcg ataccttctc     900
gagaggatca ctgagatctc tggtgtaatt gtcagcttcg acccgaaacc agtcccgggt     960
gactggaatg gagctggagc tcactgcaac tacagcacta agacaatgag aaacgatgga    1020
ggattagaag tgatcaagaa agcgataggg aagcttcagc tgaaacacaa agaacacatt    1080
gctgcttacg gtgaaggaaa cgagcgtcgt ctcactggaa agcacgaaac cgcagacatc    1140
aacacattct cttggggagt cgcgaaccgt ggagcgtcag tgagagtggg acgtgacaca    1200
gagaaggaag gtaaagggta cttcgaagac agaaggccag cttctaacat ggatccttac    1260
gttgtcacct ccatgatcgc tgagacgacc atactcggtt ga                       1302

<210> SEQ ID NO 7
<211> LENGTH: 364
<212> TYPE: PRT
<213> ORGANISM: Arabidopsis thaliana
<220> FEATURE:
<221> NAME/KEY: SITE
<222> LOCATION: (1)..(9)
<223> OTHER INFORMATION: amino terminal 9 amino acids artificial vector
      encoded sequence

<400> SEQUENCE: 7

Met Val Asp Leu Arg Asn Arg Arg Thr Ser Met Ser Leu Leu Ser Asp
1               5                   10                  15

Leu Val Asn Leu Asn Leu Thr Asp Ala Thr Gly Lys Ile Ile Ala Glu
            20                  25                  30
```

```
Tyr Ile Trp Ile Gly Gly Ser Gly Met Asp Ile Arg Ser Lys Ala Arg
             35                  40                  45

Thr Leu Pro Gly Pro Val Thr Asp Pro Ser Lys Leu Pro Lys Trp Asn
 50                  55                  60

Tyr Asp Gly Ser Ser Thr Gly Gln Ala Ala Gly Glu Asp Ser Glu Val
 65                  70                  75                  80

Ile Leu Tyr Pro Gln Ala Ile Phe Lys Asp Pro Phe Arg Lys Gly Asn
                 85                  90                  95

Asn Ile Leu Val Met Cys Asp Ala Tyr Thr Pro Ala Gly Asp Pro Ile
            100                 105                 110

Pro Thr Asn Lys Arg His Asn Ala Ala Lys Ile Phe Ser His Pro Asp
            115                 120                 125

Val Ala Lys Glu Glu Pro Trp Tyr Gly Ile Glu Gln Glu Tyr Thr Leu
130                 135                 140

Met Gln Lys Asp Val Asn Trp Pro Ile Gly Trp Pro Val Gly Gly Tyr
145                 150                 155                 160

Pro Gly Pro Gln Gly Pro Tyr Tyr Cys Gly Val Gly Ala Asp Lys Ala
                165                 170                 175

Ile Gly Arg Asp Ile Val Asp Ala His Tyr Lys Ala Cys Leu Tyr Ala
            180                 185                 190

Gly Ile Gly Ile Ser Gly Ile Asn Gly Glu Val Met Pro Gly Gln Trp
            195                 200                 205

Glu Phe Gln Val Gly Pro Val Glu Gly Ile Ser Ser Gly Asp Gln Val
210                 215                 220

Trp Val Ala Arg Tyr Leu Leu Glu Arg Ile Thr Glu Ile Ser Gly Val
225                 230                 235                 240

Ile Val Ser Phe Asp Pro Lys Pro Val Pro Gly Asp Trp Asn Gly Ala
                245                 250                 255

Gly Ala His Cys Asn Tyr Ser Thr Lys Thr Met Arg Asn Asp Gly Gly
            260                 265                 270

Leu Glu Val Ile Lys Lys Ala Ile Gly Lys Leu Gln Leu Lys His Lys
            275                 280                 285

Glu His Ile Ala Ala Tyr Gly Glu Gly Asn Glu Arg Arg Leu Thr Gly
290                 295                 300

Lys His Glu Thr Ala Asp Ile Asn Thr Phe Ser Trp Gly Val Ala Asn
305                 310                 315                 320

Arg Gly Ala Ser Val Arg Val Gly Arg Asp Thr Glu Lys Glu Gly Lys
                325                 330                 335

Gly Tyr Phe Glu Asp Arg Arg Pro Ala Ser Asn Met Asp Pro Tyr Val
            340                 345                 350

Val Thr Ser Met Ile Ala Glu Thr Thr Ile Leu Gly
            355                 360

<210> SEQ ID NO 8
<211> LENGTH: 1817
<212> TYPE: DNA
<213> ORGANISM: Artificial Sequence
<220> FEATURE:
<223> OTHER INFORMATION: Synthetic plasmid vector sequence including
      Vitis vinifera GPT coding sequence

<400> SEQUENCE: 8
aaaaaagaaa aaaaaaacat atcttgtttg tcagtatggg aagtttgaga taaggacgag      60 tgagggggtta aaattcagtg gccattgatt ttgtaatgcc aagaaccaca aaatccaatg    120
gttaccattc ctgtaagatg aggtttgcta actctttttg tccgttagat aggaagccctt   180
```

```
atcactatat atacaaggcg tcctaataac ctcttagtaa ccaattattt cagcaccatg    240
gtagatctga gggtaaattt ctagtttttc tccttcattt tcttggttag gaccctttc    300 tcttttatt tttttgagct tgatctttc tttaaactga tctatttttt aattgattgg     360
ttatggtgta aatattacat agctttaact gataatctga ttactttatt tcgtgtgtct   420
atgatgatga tgatagttac agaaccgacg aactagtatg cagctctctc aatgtacctg   480
gacattccca gagttgctta aaagaccagc cttttaagg aggagtattg atagtatttc    540
gagtagaagt aggtccagct ccaagtatcc atctttcatg gcgtccgcat caacggtctc   600
cgctccaaat acgaggctg agcagaccca taacccccct caacctctac aggttgcaaa    660
gcgcttggag aaattcaaaa caacaatctt tactcaaatg agcatgcttg ccatcaaaca   720
tggagcaata aaccttggcc aagggtttcc caactttgat ggtcctgagt ttgtcaaaga   780
agcagcaatt caagccatta aggatgggaa aaaccaatat gctcgtggat atggagttcc   840
tgatctcaac tctgctgttg ctgatagatt caagaaggat acaggactcg tggtggaccc   900
cgagaaggaa gttactgtta cttctggatg tacagaagca attgctgcta ctatgctagg   960
cttgataaat cctggtgatg aggtgatcct ctttgctcca ttttatgatt cctatgaagc  1020
cactctatcc atggctggtg cccaaataaa atccatcact ttacgtcctc cggatttgc   1080 tgtgcccatg gatgagctca gtctgcaat ctcaaagaat acccgtgcaa tcctataaa    1140 cactccccat aaccccacag gaaagatgtt cacaagggag gaactgaatg tgattgcatc  1200
cctctgcatt gagaatgatg tgttggtgtt tactgatgaa gtttacgaca agttggcttt  1260
cgaaatggat cacatttcca tggcttctct tcctgggatg tacgagagga ccgtgactat  1320
gaattcctta gggaaaactt tctccctgac tggatggaag attggttgga cagtagctcc  1380
cccacacctg acatggggag tgaggcaagc ccactcattc ctcacgtttg ctacctgcac  1440
cccaatgcaa tgggcagctg caacagccct ccgggcccca gactcttact atgaagagct  1500
aaagagagat tacagtgcaa agaaggcaat cctggtggag ggattgaagg ctgtcggttt  1560
cagggtatac ccatcaagtg ggacctattt tgtggtggtg gatcacaccc catttgggtt  1620
gaaagacgat attgcgtttt gtgagtatct gatcaaggaa gttggggtgg tagcaattcc  1680
gacaagcgtt ttctacttac acccagaaga tggaaagaac cttgtgaggt ttaccttctg  1740
taaagacgag ggaactctga gagctgcagt tgaaaggatg aaggagaaac tgaagcctaa  1800
acaatagggg cacgtga                                                 1817
```

<210> SEQ ID NO 9
<211> LENGTH: 459
<212> TYPE: PRT
<213> ORGANISM: Vitis vinifera

<400> SEQUENCE: 9

```
Met Val Asp Leu Arg Asn Arg Arg Thr Ser Met Gln Leu Ser Gln Cys
  1               5                  10                  15

Thr Trp Thr Phe Pro Glu Leu Leu Lys Arg Pro Ala Phe Leu Arg Arg
                 20                  25                  30

Ser Ile Asp Ser Ile Ser Ser Arg Ser Arg Ser Ser Lys Tyr Pro
             35                  40                  45

Ser Phe Met Ala Ser Ala Ser Thr Val Ser Ala Pro Asn Thr Glu Ala
         50                  55                  60

Glu Gln Thr His Asn Pro Pro Gln Pro Leu Gln Val Ala Lys Arg Leu
 65                  70                  75                  80
```

```
Glu Lys Phe Lys Thr Thr Ile Phe Thr Gln Met Ser Met Leu Ala Ile
                85                  90                  95

Lys His Gly Ala Ile Asn Leu Gly Gln Gly Phe Pro Asn Phe Asp Gly
            100                 105                 110

Pro Glu Phe Val Lys Glu Ala Ala Ile Gln Ala Ile Lys Asp Gly Lys
        115                 120                 125

Asn Gln Tyr Ala Arg Gly Tyr Gly Val Pro Asp Leu Asn Ser Ala Val
130                 135                 140

Ala Asp Arg Phe Lys Lys Asp Thr Gly Leu Val Val Asp Pro Glu Lys
145                 150                 155                 160

Glu Val Thr Val Thr Ser Gly Cys Thr Glu Ala Ile Ala Ala Thr Met
                165                 170                 175

Leu Gly Leu Ile Asn Pro Gly Asp Glu Val Ile Leu Phe Ala Pro Phe
            180                 185                 190

Tyr Asp Ser Tyr Glu Ala Thr Leu Ser Met Ala Gly Ala Gln Ile Lys
        195                 200                 205

Ser Ile Thr Leu Arg Pro Pro Asp Phe Ala Val Pro Met Asp Glu Leu
210                 215                 220

Lys Ser Ala Ile Ser Lys Asn Thr Arg Ala Ile Leu Ile Asn Thr Pro
225                 230                 235                 240

His Asn Pro Thr Gly Lys Met Phe Thr Arg Glu Glu Leu Asn Val Ile
                245                 250                 255

Ala Ser Leu Cys Ile Glu Asn Asp Val Leu Val Phe Thr Asp Glu Val
            260                 265                 270

Tyr Asp Lys Leu Ala Phe Glu Met Asp His Ile Ser Met Ala Ser Leu
        275                 280                 285

Pro Gly Met Tyr Glu Arg Thr Val Thr Met Asn Ser Leu Gly Lys Thr
290                 295                 300

Phe Ser Leu Thr Gly Trp Lys Ile Gly Trp Thr Val Ala Pro Pro His
305                 310                 315                 320

Leu Thr Trp Gly Val Arg Gln Ala His Ser Phe Leu Thr Phe Ala Thr
                325                 330                 335

Cys Thr Pro Met Gln Trp Ala Ala Thr Ala Leu Arg Ala Pro Asp
            340                 345                 350

Ser Tyr Tyr Glu Glu Leu Lys Arg Asp Tyr Ser Ala Lys Lys Ala Ile
        355                 360                 365

Leu Val Glu Gly Leu Lys Ala Val Gly Phe Arg Val Tyr Pro Ser Ser
370                 375                 380

Gly Thr Tyr Phe Val Val Asp His Thr Pro Phe Gly Leu Lys Asp
385                 390                 395                 400

Asp Ile Ala Phe Cys Glu Tyr Leu Ile Lys Glu Val Gly Val Val Ala
                405                 410                 415

Ile Pro Thr Ser Val Phe Tyr Leu His Pro Glu Asp Gly Lys Asn Leu
            420                 425                 430

Val Arg Phe Thr Phe Cys Lys Asp Glu Gly Thr Leu Arg Ala Ala Val
        435                 440                 445

Glu Arg Met Lys Glu Lys Leu Lys Pro Lys Gln
450                 455

<210> SEQ ID NO 10
<211> LENGTH: 1446
<212> TYPE: DNA
<213> ORGANISM: Artificial Sequence
<220> FEATURE:
```

<223> OTHER INFORMATION: Synthetic DNA encoding Oryza sativa GPT
      protein, codons optimized for expression in E. coli

<400> SEQUENCE: 10

```
atgtggatga acctggcagg ctttctggca accccggcaa ccgcaaccgc aacccgtcat    60
gaaatgccgc tgaacccgag cagcagcgcg agctttctgc tgagcagcct gcgtcgtagc   120
ctggtggcga gcctgcgtaa agcgagcccg gcagcagcag cagcactgag cccgatggca   180
agcgcaagca ccgtggcagc agaaaacggt gcagcaaaag cagcagcaga aaaacagcag   240
cagcagccgg tgcaggtggc gaaacgtctg gaaaaattta aaccaccat ttttacccag    300
atgagcatgc tggcgattaa acatggcgcg attaacctgg ccagggctt ccgaacttt    360
gatggcccgg attttgtgaa agaagcggcg attcaggcga ttaacgcggg caaaaaccag   420
tatgcgcgtg ctatggcgt gccggaactg aacagcgcga ttgcggaacg ttttctgaaa   480
gatagcggcc tgcaggtgga tccggaaaaa gaagtgaccg tgaccagcgg ctgcaccgaa   540
gcgattgcgg cgaccattct gggcctgatt aacccgggcg atgaagtgat tctgtttgcg   600
ccgttttatg atagctatga agcgaccctg agcatggcgg cgcgaacgt gaaagcgatt   660
accctgcgtc cgccggattt tagcgtgccg ctggaagaac tgaaagcggc cgtgagcaaa   720
acacccgtg cgattatgat taacaccccg cataacccga ccggcaaaat gtttacccgt   780
gaagaactgg aatttattgc gaccctgtgc aaagaaaacg atgtgctgct gtttgcggat   840
gaagtgtatg ataaactggc gtttgaagcg atcatatta gcatggcgag cattccgggc   900
atgtatgaac gtaccgtgac catgaacagc ctgggcaaaa cctttagcct gaccggctgg   960
aaaattggct gggcgattgc gccgccgcat ctgacctggg gcgtgcgtca ggcacatagc  1020
tttctgacct ttgcaacctg cacccccgatg caggcagccg ccgcagcagc actgcgtgca  1080
ccggatagct attatgaaga actgcgtcgt gattatggcg cgaaaaaagc gctgctggtg  1140
aacggcctga agatgcgggg ctttattgtg tatccgagca gcggcaccta ttttgtgatg  1200
gtggatcata ccccgtttgg ctttgataac gatattgaat tttgcgaata tctgattcgt  1260
gaagtgggcg tggtggcgat ccgccgagc gtgtttttatc tgaacccgga agatggcaaa  1320
aacctggtgc gttttacctt ttgcaaagat gatgaaaccc tgcgtgcggc ggtggaacgt  1380
atgaaaacca aactgcgtaa aaaaaagctt gcggccgcac tcgagcacca ccaccaccac  1440
cactga                                                             1446
```

<210> SEQ ID NO 11
<211> LENGTH: 481
<212> TYPE: PRT
<213> ORGANISM: Artificial Sequence
<220> FEATURE:
<223> OTHER INFORMATION: Oryza sativa GPT protein sequence with amino-
      and carboxyl-terminal vector sequences

<400> SEQUENCE: 11

```
Met Trp Met Asn Leu Ala Gly Phe Leu Ala Thr Pro Ala Thr Ala Thr
  1               5                  10                  15

Ala Thr Arg His Glu Met Pro Leu Asn Pro Ser Ser Ser Ala Ser Phe
             20                  25                  30

Leu Leu Ser Ser Leu Arg Arg Ser Leu Val Ala Ser Leu Arg Lys Ala
         35                  40                  45

Ser Pro Ala Ala Ala Ala Leu Ser Pro Met Ala Ser Ala Ser Thr
     50                  55                  60

Val Ala Ala Glu Asn Gly Ala Ala Lys Ala Ala Ala Glu Lys Gln Gln
```

-continued

```
            65                  70                  75                  80
        Gln Gln Pro Val Gln Val Ala Lys Arg Leu Glu Lys Phe Lys Thr Thr
                            85                  90                  95

Ile Phe Thr Gln Met Ser Met Leu Ala Ile Lys His Gly Ala Ile Asn
                    100                 105                 110

Leu Gly Gln Gly Phe Pro Asn Phe Asp Gly Pro Asp Phe Val Lys Glu
                    115                 120                 125

Ala Ala Ile Gln Ala Ile Asn Ala Gly Lys Asn Gln Tyr Ala Arg Gly
                    130                 135                 140

Tyr Gly Val Pro Glu Leu Asn Ser Ala Ile Ala Glu Arg Phe Leu Lys
        145                 150                 155                 160

Asp Ser Gly Leu Gln Val Asp Pro Glu Lys Glu Val Thr Val Thr Ser
                            165                 170                 175

Gly Cys Thr Glu Ala Ile Ala Ala Thr Ile Leu Gly Leu Ile Asn Pro
                    180                 185                 190

Gly Asp Glu Val Ile Leu Phe Ala Pro Phe Tyr Asp Ser Tyr Glu Ala
                    195                 200                 205

Thr Leu Ser Met Ala Gly Ala Asn Val Lys Ala Ile Thr Leu Arg Pro
        210                 215                 220

Pro Asp Phe Ser Val Pro Leu Glu Glu Leu Lys Ala Ala Val Ser Lys
        225                 230                 235                 240

Asn Thr Arg Ala Ile Met Ile Asn Thr Pro His Asn Pro Thr Gly Lys
                            245                 250                 255

Met Phe Thr Arg Glu Glu Leu Glu Phe Ile Ala Thr Leu Cys Lys Glu
                    260                 265                 270

Asn Asp Val Leu Leu Phe Ala Asp Glu Val Tyr Asp Lys Leu Ala Phe
                    275                 280                 285

Glu Ala Asp His Ile Ser Met Ala Ser Ile Pro Gly Met Tyr Glu Arg
                    290                 295                 300

Thr Val Thr Met Asn Ser Leu Gly Lys Thr Phe Ser Leu Thr Gly Trp
        305                 310                 315                 320

Lys Ile Gly Trp Ala Ile Ala Pro Pro His Leu Thr Trp Gly Val Arg
                            325                 330                 335

Gln Ala His Ser Phe Leu Thr Phe Ala Thr Cys Thr Pro Met Gln Ala
                    340                 345                 350

Ala Ala Ala Ala Ala Leu Arg Ala Pro Asp Ser Tyr Tyr Glu Glu Leu
                    355                 360                 365

Arg Arg Asp Tyr Gly Ala Lys Lys Ala Leu Leu Val Asn Gly Leu Lys
        370                 375                 380

Asp Ala Gly Phe Ile Val Tyr Pro Ser Ser Gly Thr Tyr Phe Val Met
        385                 390                 395                 400

Val Asp His Thr Pro Phe Gly Phe Asp Asn Asp Ile Glu Phe Cys Glu
                            405                 410                 415

Tyr Leu Ile Arg Glu Val Gly Val Val Ala Ile Pro Pro Ser Val Phe
                    420                 425                 430

Tyr Leu Asn Pro Glu Asp Gly Lys Asn Leu Val Arg Phe Thr Phe Cys
                    435                 440                 445

Lys Asp Asp Glu Thr Leu Arg Ala Ala Val Glu Arg Met Lys Thr Lys
        450                 455                 460

Leu Arg Lys Lys Lys Leu Ala Ala Ala Leu Glu His His His His
        465                 470                 475                 480

His
```

<210> SEQ ID NO 12
<211> LENGTH: 1251
<212> TYPE: DNA
<213> ORGANISM: Artificial Sequence
<220> FEATURE:
<223> OTHER INFORMATION: Synthetic DNA encoding Glycine max GPT protein, codons optimized for expression in E. coli

<400> SEQUENCE: 12

```
atgcatcatc accatcacca tggtaagcct atccctaacc ctctcctcgg tctcgattct     60
acggaaaacc tgtattttca gggaattgat cccttcaccg cgaaacgtct ggaaaaattt    120
cagaccacca ttttacccca gatgagcctg ctggcgatta acatggcgc gattaacctg    180
ggccagggct ttccgaactt tgatggcccg gaatttgtga agaagcggc gattcaggcg    240
attcgtgatg caaaaacca gtatgcgcgt ggctatggcg tgccggatct gaacattgcg    300
attgcggaac gttttaaaaa agataccggc ctggtggtgg atccggaaaa agaaattacc    360
gtgaccagcg ctgcaccga agcgattgcg gcgaccatga ttggcctgat taacccgggc    420
gatgaagtga ttatgtttgc gccgttttat gatagctatg aagcgaccct gagcatggcg    480
ggcgcgaaag tgaaaggcat taccctgcgt ccgccggatt ttgcggtgcc gctggaagaa    540
ctgaaaagca ccattagcaa aaacacccgt gcgattctga ttaacacccc gcataaccg     600
accggcaaaa tgtttacccg tgaagaactg aactgcattg cgagcctgtg cattgaaaac    660
gatgtgctgg tgtttaccga tgaagtgtat gataaactgg cgtttgatat ggaacatatt    720
agcatggcga gcctgccggg catgtttgaa cgtaccgtga ccctgaacag cctgggcaaa    780
acctttagcc tgaccggctg gaaaattggc tgggcgattg cgccgccgca tctgagctgg    840
ggcgtgcgtc aggcgcatgc gtttctgacc tttgcaaccg cacatccgtt tcagtgcgca    900
gcagcagcag cactgcgtgc accggatagc tattatgtgg aactgaaacg tgattatatg    960
gcgaaacgtg cgattctgat tgaaggcctg aaagcggtgg ctttaaagt gtttccgagc   1020
agcggcacct attttgtggt ggtggatcat accccgtttg gcctggaaaa cgatgtggcg   1080
ttttgcgaat atctggtgaa agaagtgggc gtggtggcga ttccgaccag cgtgttttat   1140
ctgaacccgg aagaaggcaa aaacctggtg cgttttacct tttgcaaaga tgaagaaacc   1200
attcgtagcg cggtggaacg tatgaaagcg aaactgcgta aagtcgacta a            1251
```

<210> SEQ ID NO 13
<211> LENGTH: 416
<212> TYPE: PRT
<213> ORGANISM: Artificial Sequence
<220> FEATURE:
<223> OTHER INFORMATION: Glycine max GPT amino acid sequence and amino-terminal vector sequence

<400> SEQUENCE: 13

```
Met His His His His His His Gly Lys Pro Ile Pro Asn Pro Leu Leu
  1               5                  10                  15

Gly Leu Asp Ser Thr Glu Asn Leu Tyr Phe Gln Gly Ile Asp Pro Phe
             20                  25                  30

Thr Ala Lys Arg Leu Glu Lys Phe Gln Thr Thr Ile Phe Thr Gln Met
         35                  40                  45

Ser Leu Leu Ala Ile Lys His Gly Ala Ile Asn Leu Gly Gln Gly Phe
     50                  55                  60

Pro Asn Phe Asp Gly Pro Glu Phe Val Lys Glu Ala Ala Ile Gln Ala
 65                  70                  75                  80
```

Ile Arg Asp Gly Lys Asn Gln Tyr Ala Arg Gly Tyr Gly Val Pro Asp
                85                  90                  95

Leu Asn Ile Ala Ile Ala Glu Arg Phe Lys Lys Asp Thr Gly Leu Val
            100                 105                 110

Val Asp Pro Glu Lys Glu Ile Thr Val Thr Ser Gly Cys Thr Glu Ala
        115                 120                 125

Ile Ala Ala Thr Met Ile Gly Leu Ile Asn Pro Gly Asp Glu Val Ile
    130                 135                 140

Met Phe Ala Pro Phe Tyr Asp Ser Tyr Glu Ala Thr Leu Ser Met Ala
145                 150                 155                 160

Gly Ala Lys Val Lys Gly Ile Thr Leu Arg Pro Pro Asp Phe Ala Val
                165                 170                 175

Pro Leu Glu Glu Leu Lys Ser Thr Ile Ser Lys Asn Thr Arg Ala Ile
            180                 185                 190

Leu Ile Asn Thr Pro His Asn Pro Thr Gly Lys Met Phe Thr Arg Glu
        195                 200                 205

Glu Leu Asn Cys Ile Ala Ser Leu Cys Ile Glu Asn Asp Val Leu Val
    210                 215                 220

Phe Thr Asp Glu Val Tyr Asp Lys Leu Ala Phe Asp Met Glu His Ile
225                 230                 235                 240

Ser Met Ala Ser Leu Pro Gly Met Phe Glu Arg Thr Val Thr Leu Asn
                245                 250                 255

Ser Leu Gly Lys Thr Phe Ser Leu Thr Gly Trp Lys Ile Gly Trp Ala
            260                 265                 270

Ile Ala Pro Pro His Leu Ser Trp Gly Val Arg Gln Ala His Ala Phe
        275                 280                 285

Leu Thr Phe Ala Thr Ala His Pro Phe Gln Cys Ala Ala Ala Ala Ala
    290                 295                 300

Leu Arg Ala Pro Asp Ser Tyr Tyr Val Glu Leu Lys Arg Asp Tyr Met
305                 310                 315                 320

Ala Lys Arg Ala Ile Leu Ile Glu Gly Leu Lys Ala Val Gly Phe Lys
                325                 330                 335

Val Phe Pro Ser Ser Gly Thr Tyr Phe Val Val Val Asp His Thr Pro
            340                 345                 350

Phe Gly Leu Glu Asn Asp Val Ala Phe Cys Glu Tyr Leu Val Lys Glu
        355                 360                 365

Val Gly Val Val Ala Ile Pro Thr Ser Val Phe Tyr Leu Asn Pro Glu
    370                 375                 380

Glu Gly Lys Asn Leu Val Arg Phe Thr Phe Cys Lys Asp Glu Glu Thr
385                 390                 395                 400

Ile Arg Ser Ala Val Glu Arg Met Lys Ala Lys Leu Arg Lys Val Asp
                405                 410                 415

<210> SEQ ID NO 14
<211> LENGTH: 1278
<212> TYPE: DNA
<213> ORGANISM: Hordeum vulgare

<400> SEQUENCE: 14
atggtagatc tgaggaaccg acgaactagt atgcatccg ccccgcctc cgcctccgcg      60 gccctctcca ccgccgcccc cgccgacaac ggggccgcca agcccacgga gcagcggccg    120
gtacaggtgg ctaagcgatt ggagaagttc aaaacaacaa ttttcacaca gatgagcatg    180
ctcgcagtga agcatggagc aataaacctt ggacaggggt tcccaatttt tgatggccct    240

-continued

```
gactttgtca aagatgctgc tattgaggct atcaaagctg gaaagaatca gtatgcaaga       300
ggatatggtg tgcctgaatt gaactcagct gttgctgaga gatttctcaa ggacagtgga       360
ttgcacatcg atcctgataa ggaagttact gttacatctg ggtgcacaga agcaatagct       420
gcaacgatat tgggtctgat caaccctggg gatgaagtca tactgtttgc tccattctat       480
gattcttatg aggctacact gtccatggct ggtgcgaatg tcaaagccat acactccgc       540 cctccggact tgcagtccc tcttgaagag ctaaaggctg cagtctcgaa gaataccaga       600
gcaataatga ttaatacacc tcacaaccct accgggaaaa tgttcacaag ggaggaactt       660
gagttcattg ctgatctctg caaggaaaat gacgtgttgc tctttgccga tgaggtctac       720
gacaagctgg cgtttgaggc ggatcacata tcaatggctt ctattcctgg catgtatgag       780
aggaccgtca ctatgaactc cctggggaag acgttctcct tgaccggatg aagatcggc       840 tgggcgatag caccaccgca cctgacatgg ggcgtaaggc aggcacactc cttcctcaca       900
ttcgccacct ccacgccgat gcaatcagca gcggcggcgg ccctgagagc accggacagc       960
tactttgagg agctgaagag ggactacggc gcaaagaaag cgctgctggt ggacgggctc      1020
aaggcggcgg gcttcatcgt ctacccttcg agcggaacct acttcatcat ggtcgaccac      1080
accccgttcg ggttcgacaa cgacgtcgag ttctgcgagt acttgatccg cgaggtcggc      1140
gtcgtggcca tcccgccaag cgtgttctac ctgaacccgg aggacgggaa gaacctggtg      1200
aggttcacct tctgcaagga cgacgacacg ctaagggcgg cggtggacag gatgaaggcc      1260
aagctcagga agaaatga                                                    1278
```

<210> SEQ ID NO 15
<211> LENGTH: 425
<212> TYPE: PRT
<213> ORGANISM: Hordeum vulgare

<400> SEQUENCE: 15

```
Met Val Asp Leu Arg Asn Arg Arg Thr Ser Met Ala Ser Ala Pro Ala
 1               5                  10                  15

Ser Ala Ser Ala Ala Leu Ser Thr Ala Ala Pro Ala Asp Asn Gly Ala
            20                  25                  30

Ala Lys Pro Thr Glu Gln Arg Pro Val Gln Val Ala Lys Arg Leu Glu
        35                  40                  45

Lys Phe Lys Thr Thr Ile Phe Thr Gln Met Ser Met Leu Ala Val Lys
    50                  55                  60

His Gly Ala Ile Asn Leu Gly Gln Gly Phe Pro Asn Phe Asp Gly Pro
65                  70                  75                  80

Asp Phe Val Lys Asp Ala Ala Ile Glu Ala Ile Lys Ala Gly Lys Asn
                85                  90                  95

Gln Tyr Ala Arg Gly Tyr Gly Val Pro Glu Leu Asn Ser Ala Val Ala
            100                 105                 110

Glu Arg Phe Leu Lys Asp Ser Gly Leu His Ile Asp Pro Asp Lys Glu
        115                 120                 125

Val Thr Val Thr Ser Gly Cys Thr Glu Ala Ile Ala Ala Thr Ile Leu
    130                 135                 140

Gly Leu Ile Asn Pro Gly Asp Glu Val Ile Leu Phe Ala Pro Phe Tyr
145                 150                 155                 160

Asp Ser Tyr Glu Ala Thr Leu Ser Met Ala Gly Ala Asn Val Lys Ala
                165                 170                 175

Ile Thr Leu Arg Pro Pro Asp Phe Ala Val Pro Leu Glu Glu Leu Lys
            180                 185                 190
```

Ala Ala Val Ser Lys Asn Thr Arg Ala Ile Met Ile Asn Thr Pro His
            195                 200                 205

Asn Pro Thr Gly Lys Met Phe Thr Arg Glu Glu Leu Glu Phe Ile Ala
        210                 215                 220

Asp Leu Cys Lys Glu Asn Asp Val Leu Leu Phe Ala Asp Glu Val Tyr
225                 230                 235                 240

Asp Lys Leu Ala Phe Glu Ala Asp His Ile Ser Met Ala Ser Ile Pro
                245                 250                 255

Gly Met Tyr Glu Arg Thr Val Thr Met Asn Ser Leu Gly Lys Thr Phe
                260                 265                 270

Ser Leu Thr Gly Trp Lys Ile Gly Trp Ala Ile Ala Pro Pro His Leu
            275                 280                 285

Thr Trp Gly Val Arg Gln Ala His Ser Phe Leu Thr Phe Ala Thr Ser
        290                 295                 300

Thr Pro Met Gln Ser Ala Ala Ala Ala Leu Arg Ala Pro Asp Ser
305                 310                 315                 320

Tyr Phe Glu Glu Leu Lys Arg Asp Tyr Gly Ala Lys Lys Ala Leu Leu
                325                 330                 335

Val Asp Gly Leu Lys Ala Ala Gly Phe Ile Val Tyr Pro Ser Ser Gly
            340                 345                 350

Thr Tyr Phe Ile Met Val Asp His Thr Pro Phe Gly Phe Asp Asn Asp
        355                 360                 365

Val Glu Phe Cys Glu Tyr Leu Ile Arg Glu Val Gly Val Val Ala Ile
    370                 375                 380

Pro Pro Ser Val Phe Tyr Leu Asn Pro Glu Asp Gly Lys Asn Leu Val
385                 390                 395                 400

Arg Phe Thr Phe Cys Lys Asp Asp Thr Leu Arg Ala Ala Val Asp
                405                 410                 415

Arg Met Lys Ala Lys Leu Arg Lys Lys
            420                 425

<210> SEQ ID NO 16
<211> LENGTH: 1200
<212> TYPE: DNA
<213> ORGANISM: Artificial Sequence
<220> FEATURE:
<223> OTHER INFORMATION: Synthetic DNA encoding Danio rerio GPT protein,
      codons optimized for expression in E. coli, including 5' and 3'
      vector sequences

<400> SEQUENCE: 16
atgtccgtgg cgaaacgtct ggaaaaattt aaaaccacca tttttaccca gatgagcatg      60
ctggcgatta acatggcgc gattaacctg ggccagggct ttccgaactt tgatggcccg     120
gattttgtga agaagcggc gattcaggcg attcgtgatg caacaacca gtatgcgcgt     180 ggctatggcg tgccggatct gaacattgcg attagcgaac gttataaaaa agataccggc     240
ctggcggtgg atccggaaaa agaaattacc gtgaccagcg ctgcaccga agcgattgcg     300 gcgaccgtgc tgggcctgat taacccgggc gatgaagtga ttgtgtttgc gccgttttat     360
gatagctatg aagcgacccct gagcatggcg ggcgcgaaag tgaaaggcat taccctgcgt     420
ccgccggatt ttgcgctgcc gattgaagaa ctgaaaagca ccattagcaa aacacccgt     480 gcgattctgc tgaacacccc gcataaccccg accggcaaaa tgtttacccc ggaagaactg     540
aacaccattg cgagcctgtg cattgaaaac gatgtgctgg tgtttagcga tgaagtgtat     600
gataaactgg cgtttgatat ggaacatatt agcattgcga gcctgccggg catgtttgaa     660

-continued

```
cgtaccgtga ccatgaacag cctgggcaaa acctttagcc tgaccggctg gaaaattggc   720
tgggcgattg cgccgccgca tctgacctgg ggcgtgcgtc aggcgcatgc gtttctgacc   780
tttgcaacca gcaacccgat gcagtgggca gcagcagtgg cactgcgtgc accggatagc   840
tattataccg aactgaaacg tgattatatg gcgaaacgta gcattctggt ggaaggcctg   900
aaagcggtgg gctttaaagt gtttccgagc agcggcacct attttgtggt ggtggatcat   960
accccgtttg ccatgaaaaa cgatattgcg ttttgcgaat atctggtgaa agaagtgggc  1020
gtggtggcga ttccgaccag cgtgttttat ctgaacccgg aagaaggcaa aaacctggtg  1080
cgttttacct tttgcaaaga tgaaggcacc ctgcgtgcgg cggtggatcg tatgaaagaa  1140
aaactgcgta aagtcgacaa gcttgcggcc gcactcgagc accaccacca ccaccactga  1200
```

<210> SEQ ID NO 17
<211> LENGTH: 399
<212> TYPE: PRT
<213> ORGANISM: Danio rerio
<220> FEATURE:
<221> NAME/KEY: MISC_FEATURE
<222> LOCATION: (1)..(399)
<223> OTHER INFORMATION: Amino- and carboxy-terminal amino acids shown

<400> SEQUENCE: 17

```
Met Ser Val Ala Lys Arg Leu Glu Lys Phe Lys Thr Thr Ile Phe Thr
  1               5                  10                  15

Gln Met Ser Met Leu Ala Ile Lys His Gly Ala Ile Asn Leu Gly Gln
             20                  25                  30

Gly Phe Pro Asn Phe Asp Gly Pro Asp Phe Val Lys Glu Ala Ala Ile
         35                  40                  45

Gln Ala Ile Arg Asp Gly Asn Asn Gln Tyr Ala Arg Gly Tyr Gly Val
     50                  55                  60

Pro Asp Leu Asn Ile Ala Ile Ser Glu Arg Tyr Lys Lys Asp Thr Gly
 65                  70                  75                  80

Leu Ala Val Asp Pro Glu Lys Glu Ile Thr Val Thr Ser Gly Cys Thr
                 85                  90                  95

Glu Ala Ile Ala Ala Thr Val Leu Gly Leu Ile Asn Pro Gly Asp Glu
            100                 105                 110

Val Ile Val Phe Ala Pro Phe Tyr Asp Ser Tyr Glu Ala Thr Leu Ser
        115                 120                 125

Met Ala Gly Ala Lys Val Lys Gly Ile Thr Leu Arg Pro Pro Asp Phe
    130                 135                 140

Ala Leu Pro Ile Glu Glu Leu Lys Ser Thr Ile Ser Lys Asn Thr Arg
145                 150                 155                 160

Ala Ile Leu Leu Asn Thr Pro His Asn Pro Thr Gly Lys Met Phe Thr
                165                 170                 175

Pro Glu Glu Leu Asn Thr Ile Ala Ser Leu Cys Ile Glu Asn Asp Val
            180                 185                 190

Leu Val Phe Ser Asp Glu Val Tyr Asp Lys Leu Ala Phe Asp Met Glu
        195                 200                 205

His Ile Ser Ile Ala Ser Leu Pro Gly Met Phe Glu Arg Thr Val Thr
    210                 215                 220

Met Asn Ser Leu Gly Lys Thr Phe Ser Leu Thr Gly Trp Lys Ile Gly
225                 230                 235                 240

Trp Ala Ile Ala Pro Pro His Leu Thr Trp Gly Val Arg Gln Ala His
                245                 250                 255
```

```
Ala Phe Leu Thr Phe Ala Thr Ser Asn Pro Met Gln Trp Ala Ala
            260                 265                 270

Val Ala Leu Arg Ala Pro Asp Ser Tyr Tyr Thr Glu Leu Lys Arg Asp
        275                 280                 285

Tyr Met Ala Lys Arg Ser Ile Leu Val Glu Gly Leu Lys Ala Val Gly
    290                 295                 300

Phe Lys Val Phe Pro Ser Ser Gly Thr Tyr Phe Val Val Asp His
305                 310                 315                 320

Thr Pro Phe Gly His Glu Asn Asp Ile Ala Phe Cys Glu Tyr Leu Val
                325                 330                 335

Lys Glu Val Gly Val Val Ala Ile Pro Thr Ser Val Phe Tyr Leu Asn
            340                 345                 350

Pro Glu Glu Gly Lys Asn Leu Val Arg Phe Thr Phe Cys Lys Asp Glu
        355                 360                 365

Gly Thr Leu Arg Ala Ala Val Asp Arg Met Lys Glu Lys Leu Arg Lys
    370                 375                 380

Val Asp Lys Leu Ala Ala Ala Leu Glu His His His His His His
385                 390                 395
```

<210> SEQ ID NO 18
<211> LENGTH: 1236
<212> TYPE: DNA
<213> ORGANISM: Arabidopsis thaliana

<400> SEQUENCE: 18

```
atggccaaaa tccatcgtcc tatcggagcc accatgacca cagtttcgac tcagaacgag      60
tctactcaaa aacccgtcca ggtggcgaag agattagaga agttcaagac tactattttc     120
actcaaatga gcatattggc agttaaacat ggagcgatca atttaggcca aggcttcccc     180
aatttcgacg gtcctgattt tgttaaagaa gctgcgatcc aagctattaa agatggtaaa     240
aaccagtatg ctcgtggata cggcattcct cagctcaact ctgctatagc tgcgcggttt     300
cgtgaagata cgggtcttgt tgttgatcct gagaagaag ttactgttac atctggttgc     360
acagaagcca tagctgcagc tatgttgggt ttaataaacc ctggtgatga agtcattctc     420
tttgcaccgt tttatgattc ctatgaagca acactctcta tggctggtgc taaagtaaaa     480
ggaatcactt tacgtccacc ggacttctcc atcccctttgg aagagcttaa agctgcggta     540
actaacaaga ctcgagccat ccttatgaac actccgcaca cccgaccgg agagatgttc     600
actagggagg agcttgaaac cattgcatct ctctgcattg aaaacgatgt gcttgtgttc     660
tcggatgaag tatacgataa gcttgcgttt gaaatggatc acatttctat agcttctctt     720
cccggtatgt atgaaagaac tgtgaccatg aattccctgg aaagactttt ctctttaacc     780
ggatggaaga tcggctgggc gattgcgccg cctcatctga cttggggagt tcgacaagca     840
cactcttacc tcacattcgc cacatcaaca ccagcacaat gggcagccgt tgcagctctc     900
aaggcaccag agtcttactt caaagagctg aaaagagatt acaatgtgaa aaaggagact     960
ctggttaagg gtttgaagga agtcggattt acagtgttcc catcgagcgg gacttacttt    1020
gtggttgctg atcacactcc atttggaatg gagaacgatg ttgctttctg tgagtatctt    1080
attgaagaag ttggggtcgt tgcgatccca acgagcgtct tttatctgaa tccagaagaa    1140
gggaagaatt tggttaggtt tgcgttctgt aaagacgaag agacgttgcg tggtgcaatt    1200
gagaggatga agcagaagct taagagaaaa gtctga                               1236
```

<210> SEQ ID NO 19

<211> LENGTH: 411
<212> TYPE: PRT
<213> ORGANISM: Arabidopsis thaliana

<400> SEQUENCE: 19

```
Met Ala Lys Ile His Arg Pro Ile Gly Ala Thr Met Thr Thr Val Ser
 1               5                  10                  15

Thr Gln Asn Glu Ser Thr Gln Lys Pro Val Gln Val Ala Lys Arg Leu
             20                  25                  30

Glu Lys Phe Lys Thr Thr Ile Phe Thr Gln Met Ser Ile Leu Ala Val
         35                  40                  45

Lys His Gly Ala Ile Asn Leu Gly Gln Gly Phe Pro Asn Phe Asp Gly
     50                  55                  60

Pro Asp Phe Val Lys Glu Ala Ala Ile Gln Ala Ile Lys Asp Gly Lys
 65                  70                  75                  80

Asn Gln Tyr Ala Arg Gly Tyr Gly Ile Pro Gln Leu Asn Ser Ala Ile
                 85                  90                  95

Ala Ala Arg Phe Arg Glu Asp Thr Gly Leu Val Val Asp Pro Glu Lys
            100                 105                 110

Glu Val Thr Val Thr Ser Gly Cys Thr Glu Ala Ile Ala Ala Ala Met
        115                 120                 125

Leu Gly Leu Ile Asn Pro Gly Asp Glu Val Ile Leu Phe Ala Pro Phe
    130                 135                 140

Tyr Asp Ser Tyr Glu Ala Thr Leu Ser Met Ala Gly Ala Lys Val Lys
145                 150                 155                 160

Gly Ile Thr Leu Arg Pro Pro Asp Phe Ser Ile Pro Leu Glu Glu Leu
                165                 170                 175

Lys Ala Ala Val Thr Asn Lys Thr Arg Ala Ile Leu Met Asn Thr Pro
            180                 185                 190

His Asn Pro Thr Gly Lys Met Phe Thr Arg Glu Glu Leu Glu Thr Ile
        195                 200                 205

Ala Ser Leu Cys Ile Glu Asn Asp Val Leu Val Phe Ser Asp Glu Val
    210                 215                 220

Tyr Asp Lys Leu Ala Phe Glu Met Asp His Ile Ser Ile Ala Ser Leu
225                 230                 235                 240

Pro Gly Met Tyr Glu Arg Thr Val Thr Met Asn Ser Leu Gly Lys Thr
                245                 250                 255

Phe Ser Leu Thr Gly Trp Lys Ile Gly Trp Ala Ile Ala Pro Pro His
            260                 265                 270

Leu Thr Trp Gly Val Arg Gln Ala His Ser Tyr Leu Thr Phe Ala Thr
        275                 280                 285

Ser Thr Pro Ala Gln Trp Ala Ala Val Ala Ala Leu Lys Ala Pro Glu
    290                 295                 300

Ser Tyr Phe Lys Glu Leu Lys Arg Asp Tyr Asn Val Lys Lys Glu Thr
305                 310                 315                 320

Leu Val Lys Gly Leu Lys Glu Val Gly Phe Thr Val Phe Pro Ser Ser
                325                 330                 335

Gly Thr Tyr Phe Val Val Ala Asp His Thr Pro Phe Gly Met Glu Asn
            340                 345                 350

Asp Val Ala Phe Cys Glu Tyr Leu Ile Glu Val Gly Val Val Ala
        355                 360                 365

Ile Pro Thr Ser Val Phe Tyr Leu Asn Pro Glu Glu Gly Lys Asn Leu
    370                 375                 380

Val Arg Phe Ala Phe Cys Lys Asp Glu Glu Thr Leu Arg Gly Ala Ile
```

385 390 395 400

Glu Arg Met Lys Gln Lys Leu Lys Arg Lys Val
405 410

<210> SEQ ID NO 20
<211> LENGTH: 1194
<212> TYPE: DNA
<213> ORGANISM: Arabidopsis thaliana

<400> SEQUENCE: 20
atggcgactc agaacgagtc tactcaaaaa cccgtccagg tggcgaagag attagagaag 60
ttcaagacta ctattttcac tcaaatgagc atattggcag ttaaacatgg agcgatcaat 120
ttaggccaag gctttcccaa tttcgacggt cctgattttg ttaaagaagc tgcgatccaa 180
gctattaaag atggtaaaaa ccagtatgct cgtggatacg gcattcctca gctcaactct 240
gctatagctg cgcggtttcg tgaagatacg ggtcttgttg ttgatcctga gaaagaagtt 300
actgttacat ctggttgcac agaagccata gctgcagcta tgttgggttt aataaaccct 360
ggtgatgaag tcattctctt tgcaccgttt tatgattcct atgaagcaac actctctatg 420
gctggtgcta aagtaaaagg aatcacttta cgtccaccgg acttctccat ccctttggaa 480
gagcttaaag ctgcggtaac taacaagact cgagccatcc ttatgaacac tccgcacaac 540
ccgaccggga agatgttcac tagggaggag cttgaaacca ttgcatctct ctgcattgaa 600
aacgatgtgc ttgtgttctc ggatgaagta tacgataagc ttgcgtttga aatggatcac 660
atttctatag cttctcttcc cggtatgtat gaaagaactg tgaccatgaa ttccctggga 720
aagactttct ctttaaccgg atggaagatc ggctgggcga ttgcgccgcc tcatctgact 780
tggggagttc gacaagcaca ctcttacctc acattcgcca catcaacacc agcacaatgg 840
gcagccgttg cagctctcaa ggcaccagag tcttacttca aagagctgaa aagagattac 900
aatgtgaaaa aggagactct ggttaagggt ttgaaggaag tcggatttac agtgttccca 960
tcgagcggga cttactttgt ggttgctgat cacactccat ttggaatgga gaacgatgtt 1020
gctttctgtg agtatcttat tgaagaagtt ggggtcgttg cgatcccaac gagcgtcttt 1080
tatctgaatc cagaagaagg gaagaatttg gttaggtttg cgttctgtaa agacgaagag 1140
acgttgcgtg gtgcaattga gaggatgaag cagaagctta agagaaaagt ctga 1194

<210> SEQ ID NO 21
<211> LENGTH: 397
<212> TYPE: PRT
<213> ORGANISM: Arabidopsis thaliana

<400> SEQUENCE: 21

Met Ala Thr Gln Asn Glu Ser Thr Gln Lys Pro Val Gln Val Ala Lys
1 5 10 15

Arg Leu Glu Lys Phe Lys Thr Thr Ile Phe Thr Gln Met Ser Ile Leu
20 25 30

Ala Val Lys His Gly Ala Ile Asn Leu Gly Gln Gly Phe Pro Asn Phe
35 40 45

Asp Gly Pro Asp Phe Val Lys Glu Ala Ala Ile Gln Ala Ile Lys Asp
50 55 60

Gly Lys Asn Gln Tyr Ala Arg Gly Tyr Gly Ile Pro Gln Leu Asn Ser
65 70 75 80

Ala Ile Ala Ala Arg Phe Arg Glu Asp Thr Gly Leu Val Val Asp Pro
85 90 95

Glu Lys Glu Val Thr Val Thr Ser Gly Cys Thr Glu Ala Ile Ala Ala
            100                 105                 110

Ala Met Leu Gly Leu Ile Asn Pro Gly Asp Glu Val Ile Leu Phe Ala
            115                 120                 125

Pro Phe Tyr Asp Ser Tyr Glu Ala Thr Leu Ser Met Ala Gly Ala Lys
        130                 135                 140

Val Lys Gly Ile Thr Leu Arg Pro Pro Asp Phe Ser Ile Pro Leu Glu
145                 150                 155                 160

Glu Leu Lys Ala Ala Val Thr Asn Lys Thr Arg Ala Ile Leu Met Asn
                165                 170                 175

Thr Pro His Asn Pro Thr Gly Lys Met Phe Thr Arg Glu Glu Leu Glu
            180                 185                 190

Thr Ile Ala Ser Leu Cys Ile Glu Asn Asp Val Leu Val Phe Ser Asp
        195                 200                 205

Glu Val Tyr Asp Lys Leu Ala Phe Glu Met Asp His Ile Ser Ile Ala
    210                 215                 220

Ser Leu Pro Gly Met Tyr Glu Arg Thr Val Thr Met Asn Ser Leu Gly
225                 230                 235                 240

Lys Thr Phe Ser Leu Thr Gly Trp Lys Ile Gly Trp Ala Ile Ala Pro
                245                 250                 255

Pro His Leu Thr Trp Gly Val Arg Gln Ala His Ser Tyr Leu Thr Phe
            260                 265                 270

Ala Thr Ser Thr Pro Ala Gln Trp Ala Ala Val Ala Ala Leu Lys Ala
        275                 280                 285

Pro Glu Ser Tyr Phe Lys Glu Leu Lys Arg Asp Tyr Asn Val Lys Lys
    290                 295                 300

Glu Thr Leu Val Lys Gly Leu Lys Glu Val Gly Phe Thr Val Phe Pro
305                 310                 315                 320

Ser Ser Gly Thr Tyr Phe Val Val Ala Asp His Thr Pro Phe Gly Met
                325                 330                 335

Glu Asn Asp Val Ala Phe Cys Glu Tyr Leu Ile Glu Glu Val Gly Val
            340                 345                 350

Val Ala Ile Pro Thr Ser Val Phe Tyr Leu Asn Pro Glu Glu Gly Lys
        355                 360                 365

Asn Leu Val Arg Phe Ala Phe Cys Lys Asp Glu Glu Thr Leu Arg Gly
    370                 375                 380

Ala Ile Glu Arg Met Lys Gln Lys Leu Lys Arg Lys Val
385                 390                 395

<210> SEQ ID NO 22
<211> LENGTH: 1680
<212> TYPE: DNA
<213> ORGANISM: Lycopersicon esculentum

<400> SEQUENCE: 22
ggtaccgttt gaatcctcct taaagttttt ctctggagaa actgtagtaa ttttactttg      60
ttgtgttccc ttcatctttt gaattaatgg catttgtttt aatactaatc tgcttctgaa     120
acttgtaatg tatgtatatc agtttcttat aatttatcca agtaatatct tccattctct     180
atgcaattgc ctgcataagc tcgacaaaag agtacatcaa cccctcctcc tctggactac     240
tctagctaaa cttgaatttc cccttaagat tatgaaattg atatatcctt aacaaacgac     300
tccttctgtt ggaaaatgta gtacttgtct ttcttctttt gggtatatat agtttatata     360
caccatacta tgtacaacat ccaagtagag tgaaatggat acatgtacaa gacttatttg     420

```
attgattgat gacttgagtt gccttaggag taacaaattc ttaggtcaat aaatcgttga    480
tttgaaatta atctctctgt cttagacaga taggaattat gacttccaat ggtccagaaa    540
gcaaagttcg cactgagggt atacttggaa ttgagacttg cacaggtcca gaaaccaaag    600
ttcccatcga gctctaaaat cacatctttg gaatgaaatt caattagaga taagttgctt    660
catagcatag gtaaaatgga agatgtgaag taacctgcaa taatcagtga aatgacatta    720
atacactaaa tacttcatat gtaattatcc tttccaggtt aacaatactc tataaagtaa    780
gaattatcag aaatgggctc atcaaacttt tgtactatgt atttcatata aggaagtata    840
actatacata agtgtataca caactttatt cctattttgt aaaggtggag agactgtttt    900
cgatggatct aaagcaatat gtctataaaa tgcattgata taataattat ctgagaaaat    960
ccagaattgg cgttggatta tttcagccaa atagaagttt gtaccatact tgttgattcc   1020
ttctaagtta aggtgaagta tcattcataa acagttttcc ccaaagtact actcaccaag   1080
tttccctttg tagaattaac agttcaaata tatggcgcag aaattactct atgcccaaaa   1140
ccaaacgaga aagaaacaaa atacaggggt tgcagacttt attttcgtgt tagggtgtgt   1200
tttttcatgt aattaatcaa aaatatattat gacaaaaaca tttatacata tttttactca   1260
acactctggg tatcagggtg ggttgtgttc gacaatcaat atggaaagga agtattttcc   1320 ttatttttt agttaatatt ttcagttata ccaaacatac cttgtgatat tattttaaa    1380 aatgaaaaac tcgtcagaaa gaaaagcaa aagcaacaaa aaaattgcaa gtattttta     1440 aaaaagaaaa aaaaaacata tcttgtttgt cagtatggga agtttgagat aaggacgagt   1500
gaggggttaa aattcagtgg ccattgattt tgtaatgcca agaaccacaa aatccaatgg   1560
ttaccattcc tgtaagatga ggtttgctaa ctctttttgt ccgttagata ggaagcctta   1620
tcactatata tacaaggcgt cctaataacc tcttagtaac caattattc agcaccatgg    1680
```

<210> SEQ ID NO 23
<211> LENGTH: 1230
<212> TYPE: DNA
<213> ORGANISM: Phyllostachys bambusoides

<400> SEQUENCE: 23

```
atggcctccg cggccgtctc caccgtcgcc accgccgccg acggcgtcgc gaagccgacg     60
gagaagcagc cggtacaggt cgcaaagcgt ttggaaaagt ttaagacaac aattttcaca    120
cagatgagca tgcttgccat caagcatgga gcaataaacc tcggccaggg ctttccgaat    180
tttgatggcc ctgactttgt gaagaagct gctattcaag ctatcaatgc tgggaagaat    240
cagtatgcaa gaggatatgg tgtgcctgaa ctgaactcgg ctgttgctga aaggttcctg    300
aaggacagtg gcttgcaagt cgatcccgag aaggaagtta ctgtcacatc tgggtgcacg    360
gaagcgatag ctgcaacgat attgggtctt atcaaccctg gcgatgaagt gatcttgttt    420
gctccattct atgattcata cgaggctacg ctgtcgatgg ctggtgccaa tgtaaaagcc    480
attactctcc gtcctccaga ttttgcagtc cctcttgagg agctaaaggc cacagtctct    540
aagaacacca gagcgataat gataaacaca ccacacaatc ctactgggaa atgttttct    600 agggaagaac ttgaattcat tgctactctc tgcaagaaaa atgatgtgtt gcttttttgct    660 gatgaggtct atgacaagtt ggcatttgag gcagatcata tatcaatggc ttctattcct    720
ggcatgtatg agaggactgt gactatgaac tctctgggga agacattctc tctaacagga    780
tggaagatcg gttgggcaat agcaccacca cacctgacat ggggtgtaag gcaggcacac    840
tcattcctca catttgccac ctgcacacca atgcaatcgg cggcggcggc ggctcttaga    900
```

```
gcaccagata gctactatgg ggagctgaag agggattacg gtgcaaagaa agcgatacta    960
gtcgacggac tcaaggctgc aggttttatt gtttacccct caagtggaac atactttgtc   1020
atggtcgatc acaccccgtt tggtttcgac aatgatattg agttctgcga gtatttgatc   1080
cgcgaagtcg gtgttgtcgc cataccacca agcgtatttt atctcaaccc tgaggatggg   1140
aagaacttgg tgaggttcac cttctgcaag gatgatgata cgctgagagc cgcagttgag   1200
aggatgaaga caaagctcag gaaaaaatga                                     1230
```

<210> SEQ ID NO 24
<211> LENGTH: 409
<212> TYPE: PRT
<213> ORGANISM: Phyllostachys bambusoides

<400> SEQUENCE: 24

```
Met Ala Ser Ala Ala Val Ser Thr Val Ala Thr Ala Ala Asp Gly Val
1               5                   10                  15

Ala Lys Pro Thr Glu Lys Gln Pro Val Gln Val Ala Lys Arg Leu Glu
            20                  25                  30

Lys Phe Lys Thr Thr Ile Phe Thr Gln Met Ser Met Leu Ala Ile Lys
        35                  40                  45

His Gly Ala Ile Asn Leu Gly Gln Gly Phe Pro Asn Phe Asp Gly Pro
    50                  55                  60

Asp Phe Val Lys Glu Ala Ala Ile Gln Ala Ile Asn Ala Gly Lys Asn
65                  70                  75                  80

Gln Tyr Ala Arg Gly Tyr Gly Val Pro Glu Leu Asn Ser Ala Val Ala
                85                  90                  95

Glu Arg Phe Leu Lys Asp Ser Gly Leu Gln Val Asp Pro Glu Lys Glu
            100                 105                 110

Val Thr Val Thr Ser Gly Cys Thr Glu Ala Ile Ala Ala Thr Ile Leu
        115                 120                 125

Gly Leu Ile Asn Pro Gly Asp Glu Val Ile Leu Phe Ala Pro Phe Tyr
    130                 135                 140

Asp Ser Tyr Glu Ala Thr Leu Ser Met Ala Gly Ala Asn Val Lys Ala
145                 150                 155                 160

Ile Thr Leu Arg Pro Pro Asp Phe Ala Val Pro Leu Glu Glu Leu Lys
                165                 170                 175

Ala Thr Val Ser Lys Asn Thr Arg Ala Ile Met Ile Asn Thr Pro His
            180                 185                 190

Asn Pro Thr Gly Lys Met Phe Ser Arg Glu Glu Leu Glu Phe Ile Ala
        195                 200                 205

Thr Leu Cys Lys Lys Asn Asp Val Leu Leu Phe Ala Asp Glu Val Tyr
    210                 215                 220

Asp Lys Leu Ala Phe Glu Ala Asp His Ile Ser Met Ala Ser Ile Pro
225                 230                 235                 240

Gly Met Tyr Glu Arg Thr Val Thr Met Asn Ser Leu Gly Lys Thr Phe
                245                 250                 255

Ser Leu Thr Gly Trp Lys Ile Gly Trp Ala Ile Ala Pro Pro His Leu
            260                 265                 270

Thr Trp Gly Val Arg Gln Ala His Ser Phe Leu Thr Phe Ala Thr Cys
        275                 280                 285

Thr Pro Met Gln Ser Ala Ala Ala Ala Leu Arg Ala Pro Asp Ser
    290                 295                 300

Tyr Tyr Gly Glu Leu Lys Arg Asp Tyr Gly Ala Lys Lys Ala Ile Leu
```

```
                    305                 310                 315                 320
Val Asp Gly Leu Lys Ala Ala Gly Phe Ile Val Tyr Pro Ser Ser Gly
                325                 330                 335

Thr Tyr Phe Val Met Val Asp His Thr Pro Phe Gly Phe Asp Asn Asp
            340                 345                 350

Ile Glu Phe Cys Glu Tyr Leu Ile Arg Glu Val Gly Val Val Ala Ile
        355                 360                 365

Pro Pro Ser Val Phe Tyr Leu Asn Pro Glu Asp Gly Lys Asn Leu Val
    370                 375                 380

Arg Phe Thr Phe Cys Lys Asp Asp Asp Thr Leu Arg Ala Ala Val Glu
385                 390                 395                 400

Arg Met Lys Thr Lys Leu Arg Lys Lys
                405

<210> SEQ ID NO 25
<211> LENGTH: 1858
<212> TYPE: DNA
<213> ORGANISM: Oryza sativa

<400> SEQUENCE: 25
aaaaaagaaa aaaaaaacat atcttgtttg tcagtatggg aagtttgaga taaggacgag      60 tgagggggtta aaattcagtg gccattgatt ttgtaatgcc aagaaccaca aaatccaatg    120
gttaccattc ctgtaagatg aggtttgcta actcttttg tccgttagat aggaagcctt     180
atcactatat atacaaggcg tcctaataac ctcttagtaa ccaattattt cagcaccatg    240
gtagatctga gggtaaattt ctagtttttc tccttcattt tcttggttag dacccttttc    300 tcttttatt tttttgagct ttgatctttc tttaaactga tctattttt aattgattgg     360 ttatggtgta aatattacat agctttaact gataatctga ttactttatt tcgtgtgtct   420
atgatgatga tgatagttac agaaccgacg aactagtatg aatctggccg gctttctcgc   480
cacgcccgcg accgcgaccg cgacgcggca tgagatgccg ttaaatccct cctcctccgc   540
ctccttcctc ctctcctcgc tccgccgctc gctcgtcgcg tcgctccgga aggcctcgcc   600
ggcggcggcc gcggcgctct cccccatggc tccgcgtcc accgtcgccg ccgagaacgg   660
cgccgccaag gcggcggcgg agaagcagca gcagcagcct gtgcaggttg caaagcggtt   720
ggaaaagttt aagacgacca ttttcacaca tgagtatatg cttgccatca agcatggagc   780 aataaaccctt ggccagggtt ttccgaattt cgatggccct gactttgtaa agaggctgc   840 tattcaagct atcaatgctg ggaagaatca gtacgcaaga ggatatggtg tgcctgaact   900
gaactcagct attgctgaaa gattcctgaa ggacagcgga ctgcaagtcg atccggagaa   960
ggaagttact gtcacatctg gatgcacaga agctatagct gcaacaattt taggtctaat  1020
taatccaggc gatgaagtga tattgtttgc tccattctat gattcatatg aggctaccct  1080
gtcaatggct ggtgccaacg taaaagccat tactctccgt cctccagatt tttcagtccc  1140
tcttgaagag ctaaaggctg cagtctcgaa gaacaccaga gctattatga taaacacccc  1200
gcacaatcct actgggaaaa tgtttacaag ggaagaactt gagtttattg ccactctctg  1260
caaggaaaat gatgtgctgc tttttgctga tgaggtctac gacaagttag cttttgaggc  1320
agatcatata tcaatggctt ctattcctgg catgtatgag aggaccgtga ccatgaactc  1380
tcttgggaag acattctctc ttacaggatg gaagatcggt tgggcaatcg caccgccaca  1440
cctgacatgg ggtgtaaggc aggcacactc attcctcacg tttgcgacct gcaccaat    1500 gcaagcagct gcagctgcag ctctgagagc accagatagc tactatgagg aactgaggag  1560
```

```
ggattatgga gctaagaagg cattgctagt caacggactc aaggatgcag gtttcattgt    1620
ctatccttca agtggaacat acttcgtcat ggtcgaccac accccatttg gtttcgacaa    1680
tgatattgag ttctgcgagt atttgattcg cgaagtcggt gttgtcgcca taccacctag    1740
tgtattttat ctcaaccctg aggatgggaa gaacttggtg aggttcacct tttgcaagga    1800
tgatgagacg ctgagagccg cggttgagag gatgaagaca aagctcagga aaaaatga      1858

<210> SEQ ID NO 26
<211> LENGTH: 1724
<212> TYPE: DNA
<213> ORGANISM: Artificial Sequence
<220> FEATURE:
<223> OTHER INFORMATION: Synthetic DNA encoding Hordeum vulgare GPT
      protein

<400> SEQUENCE: 26
aaaaaagaaa aaaaaaacat atcttgtttg tcagtatggg aagtttgaga taaggacgag      60
tgaggggtta aaattcagtg gccattgatt ttgtaatgcc aagaaccaca aaatccaatg     120
gttaccattc ctgtaagatg aggtttgcta actcttttg tccgttagat aggaagcctt     180
atcactatat atacaaggcg tcctaataac ctcttagtaa ccaattattt cagcaccatg     240
gtagatctga gggtaaattt ctagttttc tccttcattt tcttggttag gacccttttc     300 tcttttatt ttttgagct tgatctttc tttaaactga tctattttt aattgattgg        360 ttatggtgta aatattacat agctttaact gataatctga ttactttatt tcgtgtgtct     420
atgatgatga tgatagttac agaaccgacg aactagtatg gcatccgccc ccgcctccgc     480
ctccgcggcc ctctccaccg ccgcccccgc cgacaacggg gccgccaagc ccacggagca     540
gcggccggta caggtggcta agcgattgga gaagttcaaa acaacaattt tcacacagat     600
gagcatgctc gcagtgaagc atggagcaat aaaccttgga caggggtttc ccaattttga     660
tggccctgac tttgtcaaag atgctgctat tgaggctatc aaagctggaa gaatcagta      720 tgcaagagga tatggtgtgc ctgaattgaa ctcagctgtt gctgagagat tctctaagga     780
cagtggattg cacatcgatc ctgataagga agttactgtt acatctgggt gcacagaagc     840
aatagctgca acgatattgg gtctgatcaa ccctggggat gaagtcatac tgtttgctcc     900
attctatgat tcttatgagg ctacactgtc catggctggt gcgaatgtca aagccattac     960
actccgccct ccggactttg cagtccctct tgaagagcta aaggctgcag tctcgaagaa    1020
taccagagca ataatgatta atacacctca caacccctacc gggaaaatgt tcacaaggga   1080
ggaacttgag ttcattgctg atctctgcaa ggaaaatgac gtgttgctct tgccgatga    1140 ggtctacgac aagctggcgt ttgaggcgga tcacatatca atggcttcta ttcctggcat   1200
gtatgagagg accgtcacta tgaactccct ggggaagacg ttctccttga ccggatggaa   1260
gatcggctgg gcgatagcac caccgcacct gacatgggc gtaaggcagg cacactcctt    1320
cctcacattc gccacctcca cgccgatgca atcagcagcg gcggcggccc tgagagcacc   1380
ggacagctac tttgaggagc tgaagaggga ctacggcgca agaaagcgc tgctggtgga    1440 cgggctcaag gcggcgggct tcatcgtcta cccttcgagc ggaacctact tcatcatggt   1500
cgaccacacc ccgttcgggt tcgacaacga cgtcgagttc tgcgagtact tgatccgcga   1560
ggtcggcgtc gtggccatcc cgccaagcgt gttctacctg aacccggagg acgggaagaa   1620
cctggtgagg ttcaccttct gcaaggacga cgacacgcta agggcggcgg tggacaggat   1680
gaaggccaag ctcaggaaga aatgattgag gggcgcacgt gtga                     1724
```

<210> SEQ ID NO 27
<211> LENGTH: 1868
<212> TYPE: DNA
<213> ORGANISM: Artificial Sequence
<220> FEATURE:
<223> OTHER INFORMATION: Synthetic DNA encoding Arabidopsis thaliana GPT
      protein

<400> SEQUENCE: 27

```
catggagtca aagattcaaa tagaggacct aacagaactc gccgtaaaga ctggcgaaca        60
gttcatacag agtctcttac gactcaatga caagaagaaa atcttcgtca acatggtgga       120
gcacgacaca cttgtctact ccaaaaatat caaagataca gtctcagaag accaaagggc       180
aattgagact tttcaacaaa gggtaatatc cggaaacctc ctcggattcc attgcccagc       240
tatctgtcac tttattgtga agatagtgga aaggaaggt ggctcctaca aatgccatca       300
ttgcgataaa ggaaaggcca tcgttgaaga tgcctctgcc gacagtggtc ccaaagatgg       360
accccccaccc acgaggagca tcgtggaaaa agaagacgtt ccaaccacgt cttcaaagca       420
agtggattga tgtgatatct ccactgacgt aagggatgac gcacaatccc actatccttc       480
gcaagaccct tcctctatat aaggaagttc atttcatttg agagaacac ggggactct       540
tgaccatgta cctggacata aatggtgtga tgatcaaaca gtttagcttc aaagcctctc       600
ttctcccatt ctcttctaat ttccgacaaa gctccgccaa aatccatcgt cctatcggag       660
ccaccatgac cacagtttcg actcagaacg agtctactca aaaacccgtc caggtggcga       720
agagattaga gaagttcaag actactattt tcactcaaat gagcatattg gcagttaaac       780
atggagcgat caatttaggc caaggctttc ccaatttcga cggtcctgat tttgttaaag       840
aagctgcgat ccaagctatt aaagatggta aaaaccagta tgctcgtgga tacggcattc       900
ctcagctcaa ctctgctata gctgcgcggt tcgtgaaga tacgggtctt gttgttgatc       960
ctgagaaaga agttactgtt acatctggtt gcacagaagc catagctgca gctatgttgg     1020
gttttaataa ccctggtgat gaagtcattc tctttgcacc gttttatgat tcctatgaag     1080
caacactctc tatggctggt gctaaagtaa aaggaatcac tttacgtcca ccggacttct     1140
ccatcccttt ggaagagctt aaagctgcgg taactaacaa gactcgagcc atccttatga     1200
acactccgca caacccgacc ggaagatgt tcactaggga ggagcttgaa accattgcat     1260
ctctctgcat tgaaaacgat gtgcttgtgt tctcggatga agtatacgat aagcttgcgt     1320
ttgaaatgga tcacatttct atagcttctc ttcccggtat gtatgaaaga actgtgacca     1380
tgaattccct gggaaagact ttctctttaa ccggatggaa gatcggctgg gcgattgcgc     1440
cgcctcatct gacttgggga gttcgacaag cacactctta cctcacattc gcacatcaa     1500
caccagcaca atgggcagcc gttgcagctc tcaaggcacc agagtcttac ttcaaagagc     1560
tgaaaagaga ttacaatgtg aaaaaggaga ctctggttaa gggtttgaag gaagtcggat     1620
ttacagtgtt cccatcgagc gggacttact tgtggttgc tgatcacact ccatttggaa     1680
tggagaacga tgttgctttc tgtgagtatc ttattgaaga gttggggtc gttgcgatcc     1740
caacgagcgt ctttatctg aatccagaag aaggagaa tttggttagg tttgcgttct     1800
gtaaagacga agagacgttg cgtggtgcaa ttgagaggat gaagcagaag cttaagagaa     1860
aagtctga                                                            1868
```

<210> SEQ ID NO 28
<211> LENGTH: 1780

<212> TYPE: DNA
<213> ORGANISM: Artificial Sequence
<220> FEATURE:
<223> OTHER INFORMATION: Synthetic DNA encoding Arabidopsis thaliana GPT
    protein

<400> SEQUENCE: 28

```
aaaaaagaaa aaaaaaacat atcttgtttg tcagtatggg aagtttgaga taaggacgag    60
tgaggggtta aaattcagtg gccattgatt ttgtaatgcc aagaaccaca aaatccaatg   120
gttaccattc ctgtaagatg aggtttgcta actcttttg tccgttagat aggaagcctt   180
atcactatat atacaaggcg tcctaataac ctcttagtaa ccaattattt cagcaccatg   240
gtagatctga gggtaaattt ctagttttc tccttcattt tcttggttag dacccttttc   300
tctttttatt tttttgagct ttgatctttc tttaaactga tctatttttt aattgattgg   360
ttatggtgta aatattacat agctttaact gataatctga ttactttatt tcgtgtgtct   420
atgatgatga tgatagttac agaaccgacg aactagtatg tacctggaca taatggtgt    480
gatgatcaaa cagtttagct tcaaagcctc tcttctccca ttctcttcta atttccgaca   540
aagctccgcc aaaatccatc gtcctatcgg agccaccatg accacagttt cgactcagaa   600
cgagtctact caaaaacccg tccaggtggc gaagagatta gagaagttca agactactat   660
tttcactcaa atgagcatat ggcagttaa acatggagcg atcaatttag ccaaggctt    720
tcccaatttc gacggtcctg attttgttaa agaagctgcg atccaagcta ttaagatgg    780
taaaaaccag tatgctcgtg gatacggcat tcctcagctc aactctgcta gctgcgcg     840
gtttcgtgaa gatacgggtc ttgttgttga tcctgagaaa gaagttactg ttacatctgg   900
ttgcacagaa gccatagctg cagctatgtt gggtttaata accctggtg atgaagtcat    960
tctctttgca ccgttttatg attcctatga agcaacactc tctatggctg gtgctaaagt  1020
aaaaggaatc actttacgtc caccggactt ctccatccct ttggaagagc ttaaagctgc  1080
ggtaactaac aagactcgag ccatccttat gaacactccg cacaacccga ccggaagat   1140
gttcactagg gaggagcttg aaaccattgc atctctctgc attgaaaacg atgtgcttgt  1200
gttctcggat gaagtatacg ataagcttgc gtttgaaatg gatcacattt ctatagcttc  1260
tcttgccggt atgtatgaaa gaactgtgac catgaattcc ctgggaaaga ctttctcttt  1320
aaccggatgg aagatcggct gggcgattgc gccgcctcat ctgacttggg gagttcgaca  1380
agcacactct tacctcacat cgccacatc aacaccagca caatgggcag ccgttgcagc   1440
tctcaaggca ccagagtctt acttcaaaga gctgaaaaga gattacaatg tgaaaaagga  1500
gactctggtt aagggtttga aggaagtcgg atttacagtg ttcccatcga gcgggactta  1560
ctttgtggtt gctgatcaca ctccatttgg aatggagaac gatgttgctt tctgtgagta  1620
tcttattgaa gaagttgggg tcgttgcgat cccaacgagc gtcttttatc tgaatccaga  1680
agaagggaag aatttggtta ggtttgcgtt ctgtaaagac gaagagacgt tgcgtggtgc  1740
aattgagagg atgaagcaga agcttaagag aaaagtctga                         1780
```

<210> SEQ ID NO 29
<211> LENGTH: 1155
<212> TYPE: DNA
<213> ORGANISM: Arabidopsis thaliana

<400> SEQUENCE: 29

```
gtggcgaaga gattagagaa gttcaagact actattttca ctcaaatgag catattggca    60
gttaaacatg gagcgatcaa tttaggccaa ggctttccca atttcgacgg tcctgatttt   120
```

```
gttaaagaag ctgcgatcca agctattaaa gatggtaaaa accagtatgc tcgtggatac      180
ggcattcctc agctcaactc tgctatagct gcgcggtttc gtgaagatac gggtcttgtt      240
gttgatcctg agaaagaagt tactgttaca tctggttgca cagaagccat agctgcagct      300
atgttgggtt taataaaccc tggtgatgaa gtcattctct ttgcaccgtt ttatgattcc      360
tatgaagcaa cactctctat ggctggtgct aaagtaaaag gaatcacttt acgtccaccg      420
gacttctcca tcccttttgga agagcttaaa gctgcggtaa ctaacaagac tcgagccatc      480
cttatgaaca ctccgcacaa cccgaccggg aagatgttca ctaggggagga gcttgaaacc      540 attgcatctc tctgcattga aaacgatgtg cttgtgttct cggatgaagt atacgataag      600
cttgcgtttg aaatggatca catttctata gcttctcttc ccggtatgta tgaaagaact      660
gtgaccatga attccctggg aaagactttc tctttaaccg gatggaagat cggctgggcg      720
attgcgccgc tcatctgact tggggagtt cgacaagcac actcttacct cacattcgcc      780
acatcaacac cagcacaatg ggcagccgtt gcagctctca aggcaccaga gtcttacttc      840
aaagagctga aaagagatta caatgtgaaa aaggagactc tggttaaggg tttgaaggaa      900
gtcggattta cagtgttccc atcgagcggg acttactttg tggttgctga tcacactcca      960
tttggaatgg agaacgatgt tgctttctgt gagtatctta ttgaagaagt tggggtcgtt    1020
gcgatcccaa cgagcgtctt ttatctgaat ccagaagaag ggaagaattt ggttaggttt    1080
gcgttctgta aagacgaaga gacgttgcgt ggtgcaattg agaggatgaa gcagaagctt    1140
aagagaaaag tctga                                                     1155

<210> SEQ ID NO 30
<211> LENGTH: 384
<212> TYPE: PRT
<213> ORGANISM: Arabidopsis thaliana

<400> SEQUENCE: 30

Val Ala Lys Arg Leu Glu Lys Phe Lys Thr Thr Ile Phe Thr Gln Met
  1               5                  10                  15

Ser Ile Leu Ala Val Lys His Gly Ala Ile Asn Leu Gly Gln Gly Phe
                 20                  25                  30

Pro Asn Phe Asp Gly Pro Asp Phe Val Lys Glu Ala Ile Gln Ala
             35                  40                  45

Ile Lys Asp Gly Lys Asn Gln Tyr Ala Arg Gly Tyr Gly Ile Pro Gln
         50                  55                  60

Leu Asn Ser Ala Ile Ala Ala Arg Phe Arg Glu Asp Thr Gly Leu Val
 65                  70                  75                  80

Val Asp Pro Glu Lys Glu Val Thr Val Thr Ser Gly Cys Thr Glu Ala
                 85                  90                  95

Ile Ala Ala Ala Met Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Lys Val Lys Gly Ile Thr Leu Arg Pro Pro Asp Phe Ser Ile
    130                 135                 140

Pro Leu Glu Glu Leu Lys Ala Ala Val Thr Asn Lys Thr Arg Ala Ile
145                 150                 155                 160

Leu Met Asn Thr Pro His Asn Pro Thr Gly Lys Met Phe Thr Arg Glu
                165                 170                 175

Glu Leu Glu Thr Ile Ala Ser Leu Cys Ile Glu Asn Asp Val Leu Val
```

```
                    180                 185                 190
Phe Ser Asp Glu Val Tyr Asp Lys Leu Ala Phe Glu Met Asp His Ile
            195                 200                 205

Ser Ile Ala Ser Leu Pro Gly Met Tyr Glu Arg Thr Val Thr Met Asn
        210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ser Tyr
                245                 250                 255

Leu Thr Phe Ala Thr Ser Thr Pro Ala Gln Trp Ala Ala Val Ala Ala
            260                 265                 270

Leu Lys Ala Pro Glu Ser Tyr Phe Lys Glu Leu Lys Arg Asp Tyr Asn
        275                 280                 285

Val Lys Lys Glu Thr Leu Val Lys Gly Leu Lys Glu Val Gly Phe Thr
    290                 295                 300

Val Phe Pro Ser Ser Gly Thr Tyr Phe Val Val Ala Asp His Thr Pro
305                 310                 315                 320

Phe Gly Met Glu Asn Asp Val Ala Phe Cys Glu Tyr Leu Ile Glu Glu
                325                 330                 335

Val Gly Val Val Ala Ile Pro Thr Ser Val Phe Tyr Leu Asn Pro Glu
            340                 345                 350

Glu Gly Lys Asn Leu Val Arg Phe Ala Phe Cys Lys Asp Glu Glu Thr
        355                 360                 365

Leu Arg Gly Ala Ile Glu Arg Met Lys Gln Lys Leu Lys Arg Lys Val
    370                 375                 380

<210> SEQ ID NO 31
<211> LENGTH: 384
<212> TYPE: PRT
<213> ORGANISM: Vitis vinifera

<400> SEQUENCE: 31

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Glu Phe Val Lys Glu Ala Ala Ile Gln Ala
        35                  40                  45

Ile Lys Asp Gly Lys Asn Gln Tyr Ala Arg Gly Tyr Gly Val Pro Asp
    50                  55                  60

Leu Asn Ser Ala Val Ala Asp Arg Phe Lys Lys Asp Thr Gly Leu Val
65                  70                  75                  80

Val Asp Pro Glu Lys Glu Val Thr Val Thr Ser Gly Cys Thr Glu Ala
            85                  90                  95

Ile Ala Ala Thr Met Leu Gly Leu Ile Asn Pro Gly Asp Glu Val Ile
        100                 105                 110

Leu Phe Ala Pro Phe Tyr Asp Ser Tyr Glu Ala Thr Leu Ser Met Ala
    115                 120                 125

Gly Ala Gln Ile Lys Ser Ile Thr Leu Arg Pro Asp Phe Ala Val
    130                 135                 140

Pro Met Asp Glu Leu Lys Ser Ala Ile Ser Lys Asn Thr Arg Ala Ile
145                 150                 155                 160

Leu Ile Asn Thr Pro His Asn Pro Thr Gly Lys Met Phe Thr Arg Glu
                165                 170                 175
```

```
Glu Leu Asn Val Ile Ala Ser Leu Cys Ile Glu Asn Asp Val Leu Val
            180                 185                 190

Phe Thr Asp Glu Val Tyr Asp Lys Leu Ala Phe Glu Met Asp His Ile
        195                 200                 205

Ser Met Ala Ser Leu Pro Gly Met Tyr Glu Arg Thr Val Thr Met Asn
    210                 215                 220

Ser Leu Gly Lys Thr Phe Ser Leu Thr Gly Trp Lys Ile Gly Trp Thr
225                 230                 235                 240

Val Ala Pro Pro His Leu Thr Trp Gly Val Arg Gln Ala His Ser Phe
                245                 250                 255

Leu Thr Phe Ala Thr Cys Thr Pro Met Gln Trp Ala Ala Thr Ala
            260                 265                 270

Leu Arg Ala Pro Asp Ser Tyr Tyr Glu Glu Leu Lys Arg Asp Tyr Ser
            275                 280                 285

Ala Lys Lys Ala Ile Leu Val Glu Gly Leu Lys Ala Val Gly Phe Arg
        290                 295                 300

Val Tyr Pro Ser Ser Gly Thr Tyr Phe Val Val Asp His Thr Pro
305                 310                 315                 320

Phe Gly Leu Lys Asp Asp Ile Ala Phe Cys Glu Tyr Leu Ile Lys Glu
                325                 330                 335

Val Gly Val Val Ala Ile Pro Thr Ser Val Phe Tyr Leu His Pro Glu
            340                 345                 350

Asp Gly Lys Asn Leu Val Arg Phe Thr Phe Cys Lys Asp Glu Gly Thr
            355                 360                 365

Leu Arg Ala Ala Val Glu Arg Met Lys Glu Lys Leu Lys Pro Lys Gln
370                 375                 380

<210> SEQ ID NO 32
<211> LENGTH: 383
<212> TYPE: PRT
<213> ORGANISM: Oryza sativa

<400> SEQUENCE: 32

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Asn Ala Gly Lys Asn Gln Tyr Ala Arg Gly Tyr Gly Val Pro Glu
    50                  55                  60

Leu Asn Ser Ala Ile Ala Glu Arg Phe Leu Lys Asp Ser Gly Leu Gln
65                  70                  75                  80

Val Asp Pro Glu Lys Glu Val Thr Val Thr Ser Gly Cys Thr Glu Ala
                85                  90                  95

Ile Ala Thr Ile Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Asn Val Lys Ala Ile Thr Leu Arg Pro Asp Phe Ser Val
    130                 135                 140

Pro Leu Glu Glu Leu Lys Ala Ala Val Ser Lys Asn Thr Arg Ala Ile
145                 150                 155                 160

Met Ile Asn Thr Pro His Asn Pro Thr Gly Lys Met Phe Thr Arg Glu
                165                 170                 175
```

```
Glu Leu Glu Phe Ile Ala Thr Leu Cys Lys Glu Asn Asp Val Leu Leu
            180                 185                 190

Phe Ala Asp Glu Val Tyr Asp Lys Leu Ala Phe Glu Ala Asp His Ile
        195                 200                 205

Ser Met Ala Ser Ile Pro Gly Met Tyr Glu Arg Thr Val Thr Met Asn
    210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ser Phe
                245                 250                 255

Leu Thr Phe Ala Thr Cys Thr Pro Met Gln Ala Ala Ala Ala Ala Ala
            260                 265                 270

Leu Arg Ala Pro Asp Ser Tyr Tyr Glu Glu Leu Arg Arg Asp Tyr Gly
        275                 280                 285

Ala Lys Lys Ala Leu Leu Val Asn Gly Leu Lys Asp Ala Gly Phe Ile
    290                 295                 300

Val Tyr Pro Ser Ser Gly Thr Tyr Phe Val Met Val Asp His Thr Pro
305                 310                 315                 320

Phe Gly Phe Asp Asn Asp Ile Glu Phe Cys Glu Tyr Leu Ile Arg Glu
                325                 330                 335

Val Gly Val Val Ala Ile Pro Pro Ser Val Phe Tyr Leu Asn Pro Glu
            340                 345                 350

Asp Gly Lys Asn Leu Val Arg Phe Thr Phe Cys Lys Asp Asp Glu Thr
        355                 360                 365

Leu Arg Ala Ala Val Glu Arg Met Lys Thr Lys Leu Arg Lys Lys
    370                 375                 380

<210> SEQ ID NO 33
<211> LENGTH: 383
<212> TYPE: PRT
<213> ORGANISM: Glycine max

<400> SEQUENCE: 33

Ala Lys Arg Leu Glu Lys Phe Gln Thr Thr Ile Phe Thr Gln Met Ser
1               5                   10                  15

Leu Leu Ala Ile Lys His Gly Ala Ile Asn Leu Gly Gln Gly Phe Pro
            20                  25                  30

Asn Phe Asp Gly Pro Glu Phe Val Lys Glu Ala Ala Ile Gln Ala Ile
        35                  40                  45

Arg Asp Gly Lys Asn Gln Tyr Ala Arg Gly Tyr Gly Val Pro Asp Leu
    50                  55                  60

Asn Ile Ala Ile Ala Glu Arg Phe Lys Lys Asp Thr Gly Leu Val Val
65                  70                  75                  80

Asp Pro Glu Lys Glu Ile Thr Val Thr Ser Gly Cys Thr Glu Ala Ile
                85                  90                  95

Ala Ala Thr Met Ile Gly Leu Ile Asn Pro Gly Asp Glu Val Ile Met
            100                 105                 110

Phe Ala Pro Phe Tyr Asp Ser Tyr Glu Ala Thr Leu Ser Met Ala Gly
        115                 120                 125

Ala Lys Val Lys Gly Ile Thr Leu Arg Pro Pro Asp Phe Ala Val Pro
    130                 135                 140

Leu Glu Glu Leu Lys Ser Thr Ile Ser Lys Asn Thr Arg Ala Ile Leu
145                 150                 155                 160

Ile Asn Thr Pro His Asn Pro Thr Gly Lys Met Phe Thr Arg Glu Glu
```

```
                     165                 170                 175
Leu Asn Cys Ile Ala Ser Leu Cys Ile Glu Asn Asp Val Leu Val Phe
                180                 185                 190

Thr Asp Glu Val Tyr Asp Lys Leu Ala Phe Asp Met Glu His Ile Ser
            195                 200                 205

Met Ala Ser Leu Pro Gly Met Phe Glu Arg Thr Val Thr Leu Asn Ser
        210                 215                 220

Leu Gly Lys Thr Phe Ser Leu Thr Gly Trp Lys Ile Gly Trp Ala Ile
225                 230                 235                 240

Ala Pro Pro His Leu Ser Trp Gly Val Arg Gln Ala His Ala Phe Leu
                245                 250                 255

Thr Phe Ala Thr Ala His Pro Phe Gln Cys Ala Ala Ala Ala Ala Leu
            260                 265                 270

Arg Ala Pro Asp Ser Tyr Tyr Val Glu Leu Lys Arg Asp Tyr Met Ala
        275                 280                 285

Lys Arg Ala Ile Leu Ile Glu Gly Leu Lys Ala Val Gly Phe Lys Val
    290                 295                 300

Phe Pro Ser Ser Gly Thr Tyr Phe Val Val Asp His Thr Pro Phe
305                 310                 315                 320

Gly Leu Glu Asn Asp Val Ala Phe Cys Glu Tyr Leu Val Lys Glu Val
                325                 330                 335

Gly Val Val Ala Ile Pro Thr Ser Val Phe Tyr Leu Asn Pro Glu Glu
            340                 345                 350

Gly Lys Asn Leu Val Arg Phe Thr Phe Cys Lys Asp Glu Glu Thr Ile
        355                 360                 365

Arg Ser Ala Val Glu Arg Met Lys Ala Lys Leu Arg Lys Val Asp
    370                 375                 380

<210> SEQ ID NO 34
<211> LENGTH: 383
<212> TYPE: PRT
<213> ORGANISM: Hordeum vulgare

<400> SEQUENCE: 34

Val Ala Lys Arg Leu Glu Lys Phe Lys Thr Thr Ile Phe Thr Gln Met
1               5                   10                  15

Ser Met Leu Ala Val Lys His Gly Ala Ile Asn Leu Gly Gln Gly Phe
            20                  25                  30

Pro Asn Phe Asp Gly Pro Asp Phe Val Lys Asp Ala Ala Ile Glu Ala
        35                  40                  45

Ile Lys Ala Gly Lys Asn Gln Tyr Ala Arg Gly Tyr Gly Val Pro Glu
    50                  55                  60

Leu Asn Ser Ala Val Ala Glu Arg Phe Leu Lys Asp Ser Gly Leu His
65                  70                  75                  80

Ile Asp Pro Asp Lys Glu Val Thr Val Thr Ser Gly Cys Thr Glu Ala
                85                  90                  95

Ile Ala Ala Thr Ile Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Asn Val Lys Ala Ile Thr Leu Arg Pro Pro Asp Phe Ala Val
    130                 135                 140

Pro Leu Glu Glu Leu Lys Ala Ala Val Ser Lys Asn Thr Arg Ala Ile
145                 150                 155                 160
```

```
Met Ile Asn Thr Pro His Asn Pro Thr Gly Lys Met Phe Thr Arg Glu
            165                 170                 175

Glu Leu Glu Phe Ile Ala Asp Leu Cys Lys Glu Asn Asp Val Leu Leu
        180                 185                 190

Phe Ala Asp Glu Val Tyr Asp Lys Leu Ala Phe Glu Ala Asp His Ile
    195                 200                 205

Ser Met Ala Ser Ile Pro Gly Met Tyr Glu Arg Thr Val Thr Met Asn
210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ser Phe
                245                 250                 255

Leu Thr Phe Ala Thr Ser Thr Pro Met Gln Ser Ala Ala Ala Ala
            260                 265                 270

Leu Arg Ala Pro Asp Ser Tyr Phe Glu Glu Leu Lys Arg Asp Tyr Gly
        275                 280                 285

Ala Lys Lys Ala Leu Leu Val Asp Gly Leu Lys Ala Ala Gly Phe Ile
    290                 295                 300

Val Tyr Pro Ser Ser Gly Thr Tyr Phe Ile Met Val Asp His Thr Pro
305                 310                 315                 320

Phe Gly Phe Asp Asn Asp Val Glu Phe Cys Glu Tyr Leu Ile Arg Glu
                325                 330                 335

Val Gly Val Val Ala Ile Pro Pro Ser Val Phe Tyr Leu Asn Pro Glu
            340                 345                 350

Asp Gly Lys Asn Leu Val Arg Phe Thr Phe Cys Lys Asp Asp Asp Thr
        355                 360                 365

Leu Arg Ala Ala Val Asp Arg Met Lys Ala Lys Leu Arg Lys Lys
    370                 375                 380

<210> SEQ ID NO 35
<211> LENGTH: 382
<212> TYPE: PRT
<213> ORGANISM: Danio rerio

<400> SEQUENCE: 35

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Arg Asp Gly Asn Asn Gln Tyr Ala Arg Gly Tyr Gly Val Pro Asp
    50                  55                  60

Leu Asn Ile Ala Ile Ser Glu Arg Tyr Lys Lys Asp Thr Gly Leu Ala
65                  70                  75                  80

Val Asp Pro Glu Lys Glu Ile Thr Val Thr Ser Gly Cys Thr Glu Ala
                85                  90                  95

Ile Ala Ala Thr Val Leu Gly Leu Ile Asn Pro Gly Asp Glu Val Ile
            100                 105                 110

Val Phe Ala Pro Phe Tyr Asp Ser Tyr Glu Ala Thr Leu Ser Met Ala
        115                 120                 125

Gly Ala Lys Val Lys Gly Ile Thr Leu Arg Pro Pro Asp Phe Ala Leu
    130                 135                 140

Pro Ile Glu Glu Leu Lys Ser Thr Ile Ser Lys Asn Thr Arg Ala Ile
145                 150                 155                 160
```

```
Leu Leu Asn Thr Pro His Asn Pro Thr Gly Lys Met Phe Thr Pro Glu
            165                 170                 175

Glu Leu Asn Thr Ile Ala Ser Leu Cys Ile Glu Asn Asp Val Leu Val
        180                 185                 190

Phe Ser Asp Glu Val Tyr Asp Lys Leu Ala Phe Asp Met Glu His Ile
    195                 200                 205

Ser Ile Ala Ser Leu Pro Gly Met Phe Glu Arg Thr Val Thr Met Asn
210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ala Phe
                245                 250                 255

Leu Thr Phe Ala Thr Ser Asn Pro Met Gln Trp Ala Ala Ala Val Ala
            260                 265                 270

Leu Arg Ala Pro Asp Ser Tyr Tyr Thr Glu Leu Lys Arg Asp Tyr Met
        275                 280                 285

Ala Lys Arg Ser Ile Leu Val Glu Gly Leu Lys Ala Val Gly Phe Lys
    290                 295                 300

Val Phe Pro Ser Ser Gly Thr Tyr Phe Val Val Asp His Thr Pro
305                 310                 315                 320

Phe Gly His Glu Asn Asp Ile Ala Phe Cys Glu Tyr Leu Val Lys Glu
                325                 330                 335

Val Gly Val Val Ala Ile Pro Thr Ser Val Phe Tyr Leu Asn Pro Glu
            340                 345                 350

Glu Gly Lys Asn Leu Val Arg Phe Thr Phe Cys Lys Asp Glu Gly Thr
        355                 360                 365

Leu Arg Ala Ala Val Asp Arg Met Lys Glu Lys Leu Arg Lys
    370                 375                 380

<210> SEQ ID NO 36
<211> LENGTH: 383
<212> TYPE: PRT
<213> ORGANISM: Phyllostachys bambusoides

<400> SEQUENCE: 36

Val Ala Lys Arg Leu Glu Lys Phe Lys Thr Thr Ile Phe Thr Gln Met
1               5                   10                  15

Ser Met Leu Ala Ile Lys His Gly Ala Ile Asn Leu Gly Gln Gly Phe
            20                  25                  30

Pro Asn Phe Asp Gly Pro Asp Phe Val Lys Glu Ala Ala Ile Gln Ala
        35                  40                  45

Ile Asn Ala Gly Lys Asn Gln Tyr Ala Arg Gly Tyr Gly Val Pro Glu
    50                  55                  60

Leu Asn Ser Ala Val Ala Glu Arg Phe Leu Lys Asp Ser Gly Leu Gln
65                  70                  75                  80

Val Asp Pro Glu Lys Glu Val Thr Val Thr Ser Gly Cys Thr Glu Ala
            85                  90                  95

Ile Ala Ala Thr Ile Leu Gly Leu Ile Asn Pro Gly Asp Glu Val Ile
            100                 105                 110

Leu Phe Ala Pro Phe Tyr Asp Ser Tyr Glu Ala Thr Leu Ser Met Ala
        115                 120                 125

Gly Ala Asn Val Lys Ala Ile Thr Leu Arg Pro Asp Phe Ala Val
    130                 135                 140

Pro Leu Glu Glu Leu Lys Ala Thr Val Ser Lys Asn Thr Arg Ala Ile
```

```
                145                 150                 155                 160
Met Ile Asn Thr Pro His Asn Pro Thr Gly Lys Met Phe Ser Arg Glu
                    165                 170                 175

Glu Leu Glu Phe Ile Ala Thr Leu Cys Lys Lys Asn Asp Val Leu Leu
                    180                 185                 190

Phe Ala Asp Glu Val Tyr Asp Lys Leu Ala Phe Glu Ala Asp His Ile
                    195                 200                 205

Ser Met Ala Ser Ile Pro Gly Met Tyr Glu Arg Thr Val Thr Met Asn
        210                 215                 220

Ser Leu Gly Lys Thr Phe Ser Leu Thr Gly Trp Lys Ile Gly Trp Ala
225                 230                 235                 240

Ile Ala Pro Pro His Leu Thr Trp Gly Val Arg Gln Ala His Ser Phe
                    245                 250                 255

Leu Thr Phe Ala Thr Cys Thr Pro Met Gln Ser Ala Ala Ala Ala Ala
                    260                 265                 270

Leu Arg Ala Pro Asp Ser Tyr Tyr Gly Glu Leu Lys Arg Asp Tyr Gly
        275                 280                 285

Ala Lys Lys Ala Ile Leu Val Asp Gly Leu Lys Ala Ala Gly Phe Ile
        290                 295                 300

Val Tyr Pro Ser Ser Gly Thr Tyr Phe Val Met Val Asp His Thr Pro
305                 310                 315                 320

Phe Gly Phe Asp Asn Asp Ile Glu Phe Cys Glu Tyr Leu Ile Arg Glu
                    325                 330                 335

Val Gly Val Val Ala Ile Pro Pro Ser Val Phe Tyr Leu Asn Pro Glu
                    340                 345                 350

Asp Gly Lys Asn Leu Val Arg Phe Thr Phe Cys Lys Asp Asp Asp Thr
        355                 360                 365

Leu Arg Ala Ala Val Glu Arg Met Lys Thr Lys Leu Arg Lys Lys
        370                 375                 380

<210> SEQ ID NO 37
<211> LENGTH: 2992
<212> TYPE: DNA
<213> ORGANISM: Artificial Sequence
<220> FEATURE:
<223> OTHER INFORMATION: Synthetic expression cassette

<400> SEQUENCE: 37
ctgcagcaaa gaaacgttat tagttggtgc ttttggtggt aggaatgtag ttttctgaca      60
aagtcaatta ctgaatataa aaaaaatctg cacagctctg cgtcaacagt tgtccaaggg     120
atgcctcaaa atctgtgca gattatcagt cgtcacgcag aagcagaaca tcatggtgtg     180
ctaggtcagc ttcttgcatt gggccatgaa tccggttggt tgttaatctc tcctctctta    240
ttctcttata ttaagatgca taactctttt atgtagtcta aaaaaaaatc cagtggatcg    300
gatagtagta cgtcatggtg ccattaggta ccgttgaacc taacagatat ttatgcatgt    360
gtatatatat agctatatag acaaaattga tgccgattat agacccaaaa gcaataggta    420
tatataatat aatacagacc acaccaccaa actaagaatc gatcaaatag acaaggcatg    480
tctccaaatt gtcttaaact atttccgtag gttcagccgt tcaggagtcg aatcagcctc    540
tgccggcgtt ttcttgcac gtacgacgga cacacatggg cataccatat agctggtcca    600
tgacattagg agagagaacg tacgtgttga cctgtagctg agatataaca aggttgatta    660
taatatcacc aaacatgaaa tcatccaagg atgacccata actatcacta ctatagtact    720
gcatctggta aaagaaattg tatagactct atttcgagca ctaccacata acgcctgcaa    780
```

```
tgtgacaccc tacctattca ctaatgtgcc tcttcccaca cgctttccac ccgtactgct    840
cacagcttta agaaccagaa caaatgagta atattagtgt cggttcatgg ctaaaaccag    900
cactgatgta catgaccaca tatgtcaaat gctgcttcta ggcatgaccc gctcttacta    960
atacctactc atcgctagaa gaattttcgg ctgataaatt ttcaatttaa gcaagagtta   1020
tctgcgttgg ttcataactc aaactgatgg ccccaaccat attagtgcaa atttcacata   1080
tgatcataac cttttcatat gaaatcggat cgagatgaac tttatataaa cattgtagct   1140
gtcgatgata cctacaattt tatagttcac aacctttta tttcaagtca tttaaatgcc    1200
caaataggtg tttcaaatct cagatagaaa tgttcaaaag taaaaaaggt ccctatcata   1260
acataattga tatgtaagtg agttggaaaa agataagtac gtgtgagaga gatcggggat   1320
caaattctgg tgtaataatg tatgtatttc agtcataaaa attggtagca gtagttgggg   1380
ctctgtatat ataccggtaa ggatgggatg gtagtagaat aattcttttt ttgttttag    1440 tttttctgg tccaaaattt caaatttgga tcccttactt gtaccaacta atattaatga    1500
gtgttgaggg tagtagaggt gcaactttac cataatccct ctgtttcagg ttataagacg   1560
ttttgacttt aaatttgacc aagtttatgc gcaaatatag taatatttat aatactatat   1620
tagtttcatt aaataaataa ttgaatatat tttcataata aatttgtgtt gagttcaaaa   1680
tattattaat tttttctaca aacttggtca aacttgaagc agtttgactt tgaccaaagt   1740
caaaacgtct tataacttga aacggatgga ttactttttt tgtggggaca agtttacaat   1800
gtttaataaa gcacaatcca tcttaatgtt ttcaagctga atattgtaaa attcatggat   1860
aaaccagctt ctaaatgttt aaccgggaaa atgtcgaacg acaaattaat attttaagt   1920 gatggggagt attaattaag gagtgacaac tcaactttca atatcgtact aaactgtggg   1980
attatttttc taaaatttta taccctgcca attcacgtgt tgtagatctt ttttttcac   2040 taaccgacac caggtatatc aattttattg aatatagcag caaaaagaat gtgttgtact   2100
tgtaaacaaa aagcaaactg tacataaaaa aaaatgcact cctatataat taagctcata   2160
aagatgcttt gcttcgtgag ggcccaagtt ttgatgacct tttgcttgat ctcgaaatta   2220
aaatttaagt actgttaagg gagttcacac caccatcaat tttcagcctg aagaaacagt   2280
taaacaacga ccccgatgac cagtctactg ctctccacat actagctgca ttattgatca   2340
caaaacaaaa caaaacgaaa taaaaatcag cagcgagagt gtgcagagag agacaaaggt   2400
gatctggcgt ggatatctcc ccatccatcc tcacccgcgc tgcccatcac tcgccgccgc   2460
atactccatc atgtggagag aggaagacga ggaccacagc cagagcccgg gtcgagatgc   2520
caccacggcc acaacccacg agcccggcgc gacaccaccg cgcgcgcgtg agccagccac   2580
aaacgcccgc ggataggcgc gcgcacgccg gccaatccta ccacatcccc ggcctccgcg   2640
gctcgcgagc gccgctgcca tccgatccgc tgagttttgg ctatttatac gtaccgcggg   2700
agcctgtgtg cagagcagtg catctcaaga agtactcgag caaagaagga gagagcttgg   2760
tgagctgcag ccatggtaga tctgagggta aatttctagt ttttctcctt cattttcttg   2820
gttaggaccc ttttctcttt ttatttttt gagctttgat cttctcttaa actgatctat   2880 ttttaattg attggttatg gtgtaaatat tacatagctt taactgataa tctgattact   2940
ttatttcgtg tgtctatgat gatgatgata gttacagaac cgacgaacta gt           2992

<210> SEQ ID NO 38
<211> LENGTH: 1281
<212> TYPE: DNA
```

<213> ORGANISM: Hordeum vulgare

<400> SEQUENCE: 38

```
gcgcaggcgg ttgtgcaggc gatgcagtgc caggtggggg tgaggggcag gacggccgtc      60
ccggcgaggc agcccgcggg cagggtgtgg ggcgtcagga gggccgcccg cgccacctcc     120
gggttcaagg tgctggcgct cggcccggag accaccgggg tcatccagag gatgcagcag     180
ctgctcgaca tggacaccac gcccttcacc gacaagatca tcgccgagta catctgggtt     240
ggaggatctg gaattgacct cagaagcaaa tcaaggacga tttcgaagcc agtggaggac     300
ccgtcagagc tgccgaaatg gaactacgac ggatcgagca cggggcaggc tcctggggaa     360
gacagtgaag tcatcctata cccacaggcc atattcaagg acccattccg aggaggcaac     420
aacatactgg ttatctgtga cacctacaca ccacagggg aacccatccc tactaacaaa     480
cgccacatgg ctgcacaaat cttcagtgac cccaaggtca cttcacaagt gccatggttc     540
ggaatcgaac aggagtacac tctgatgcag agggatgtga actggcctct tggctggcct     600
gttggagggt accctggccc ccaggtccaa tactactgcg ccgtaggatc agacaagtca     660
tttggccgtg acatatcaga tgctcactac aaggcgtgcc tttacgctgg aattgaaatc     720
agtggaacaa cggggaggt catgcctggt cagtgggagt accaggttgg acccagcgtt     780
ggtattgatg caggagacca catatgggct tccagataca ttctcgagag aatcacggag     840
caagctggtg tggtgctcac ccttgaccca aaaccaatcc agggtgactg aacggagct     900
ggctgccaca caaactacag cacattgagc atgcgcgagg atggaggttt cgacgtgatc     960
aagaaggcaa tcctgaacct ttcacttcgc catgacttgc acatagccgc atatggtgaa    1020
ggaaacgagc ggaggttgac agggctacac gagacagcta gcatatcaga cttctcatgg    1080
ggtgtgcga accgtggctg ctctattcgt gtggggcgag acaccgaggc gaagggcaaa    1140
ggatacctgg aggaccgtcg cccggcctcc aacatggacc cgtacaccgt gacggcgctg    1200
ctggccgaga ccacgatcct gtgggagccg accctcgagg cggaggccct cgctgccaag    1260
aagctggcgc tgaaggtatg a                                              1281
```

<210> SEQ ID NO 39
<211> LENGTH: 426
<212> TYPE: PRT
<213> ORGANISM: Hordeum vulgare

<400> SEQUENCE: 39

```
Ala Gln Ala Val Val Gln Ala Met Gln Cys Gln Val Gly Val Arg Gly
 1               5                  10                  15

Arg Thr Ala Val Pro Ala Arg Gln Pro Ala Gly Arg Val Trp Gly Val
            20                  25                  30

Arg Arg Ala Ala Arg Ala Thr Ser Gly Phe Lys Val Leu Ala Leu Gly
        35                  40                  45

Pro Glu Thr Thr Gly Val Ile Gln Arg Met Gln Gln Leu Leu Asp Met
    50                  55                  60

Asp Thr Thr Pro Phe Thr Asp Lys Ile Ile Ala Glu Tyr Ile Trp Val
65                  70                  75                  80

Gly Gly Ser Gly Ile Asp Leu Arg Ser Lys Ser Arg Thr Ile Ser Lys
                85                  90                  95

Pro Val Glu Asp Pro Ser Glu Leu Pro Lys Trp Asn Tyr Asp Gly Ser
            100                 105                 110

Ser Thr Gly Gln Ala Pro Gly Glu Asp Ser Glu Val Ile Leu Tyr Pro
        115                 120                 125
```

```
Gln Ala Ile Phe Lys Asp Pro Phe Arg Gly Gly Asn Asn Ile Leu Val
        130                 135                 140

Ile Cys Asp Thr Tyr Thr Pro Gln Gly Glu Pro Ile Pro Thr Asn Lys
145                 150                 155                 160

Arg His Met Ala Ala Gln Ile Phe Ser Asp Pro Lys Val Thr Ser Gln
                165                 170                 175

Val Pro Trp Phe Gly Ile Glu Gln Glu Tyr Thr Leu Met Gln Arg Asp
                180                 185                 190

Val Asn Trp Pro Leu Gly Trp Pro Val Gly Gly Tyr Pro Gly Pro Gln
        195                 200                 205

Gly Pro Tyr Tyr Cys Ala Val Gly Ser Asp Lys Ser Phe Gly Arg Asp
        210                 215                 220

Ile Ser Asp Ala His Tyr Lys Ala Cys Leu Tyr Ala Gly Ile Glu Ile
225                 230                 235                 240

Ser Gly Thr Asn Gly Glu Val Met Pro Gly Gln Trp Glu Tyr Gln Val
                245                 250                 255

Gly Pro Ser Val Gly Ile Asp Ala Gly Asp His Ile Trp Ala Ser Arg
                260                 265                 270

Tyr Ile Leu Glu Arg Ile Thr Glu Gln Ala Gly Val Val Leu Thr Leu
        275                 280                 285

Asp Pro Lys Pro Ile Gln Gly Asp Trp Asn Gly Ala Gly Cys His Thr
290                 295                 300

Asn Tyr Ser Thr Leu Ser Met Arg Glu Asp Gly Gly Phe Asp Val Ile
305                 310                 315                 320

Lys Lys Ala Ile Leu Asn Leu Ser Leu Arg His Asp Leu His Ile Ala
                325                 330                 335

Ala Tyr Gly Glu Gly Asn Glu Arg Arg Leu Thr Gly Leu His Glu Thr
                340                 345                 350

Ala Ser Ile Ser Asp Phe Ser Trp Gly Val Ala Asn Arg Gly Cys Ser
        355                 360                 365

Ile Arg Val Gly Arg Asp Thr Glu Ala Lys Gly Lys Gly Tyr Leu Glu
370                 375                 380

Asp Arg Arg Pro Ala Ser Asn Met Asp Pro Tyr Thr Val Thr Ala Leu
385                 390                 395                 400

Leu Ala Glu Thr Thr Ile Leu Trp Glu Pro Thr Leu Glu Ala Glu Ala
                405                 410                 415

Leu Ala Ala Lys Lys Leu Ala Leu Lys Val
                420                 425

<210> SEQ ID NO 40
<211> LENGTH: 4273
<212> TYPE: DNA
<213> ORGANISM: Artificial Sequence
<220> FEATURE:
<223> OTHER INFORMATION: Synthetic expression cassette

<400> SEQUENCE: 40
ctgcagcaaa gaaacgttat tagttggtgc ttttggtggt aggaatgtag ttttctgaca      60
aagtcaatta ctgaatataa aaaaaatctg cacagctctg cgtcaacagt tgtccaaggg     120
atgcctcaaa atctgtgcag attatcagtc gtcacgcagc aagcagaaca tcatggtgtg     180
ctaggtcagc ttcttgcatt gggccatgaa tccggttggt tgttaatctc tcctctctta     240
ttctcttata ttaagatgca taactctttt atgtagtcta aaaaaaaatc cagtggatcg     300
gatagtagta cgtcatggtg ccattaggta ccgttgaacc taacagatat ttatgcatgt     360
```

```
gtatatatat agctatatag acaaaattga tgccgattat agacccaaaa gcaataggta    420
tatataatat aatacagacc acaccaccaa actaagaatc gatcaaatag acaaggcatg    480
tctccaaatt gtcttaaact atttccgtag gttcagccgt tcaggagtcg aatcagcctc    540
tgccggcgtt ttctttgcac gtacgacgga cacacatggg cataccatat agctggtcca    600
tgacattagg agagagaacg tacgtgttga cctgtagctg agatataaca aggttgatta    660
taatatcacc aaacatgaaa tcatccaagg atgacccata actatcacta ctatagtact    720
gcatctggta aagaaattg tatagactct atttcgagca ctaccacata acgcctgcaa    780
tgtgacaccc tacctattca ctaatgtgcc tcttcccaca cgctttccac ccgtactgct    840
cacagcttta agaaccagaa caaatgagta atattagtgt cggttcatgg ctaaaaccag    900
cactgatgta catgaccaca tatgtcaaat gctgcttcta ggcatgaccc gctcttacta    960
atacctactc atcgctagaa gaattttcgg ctgataaatt ttcaatttaa gcaagagtta   1020
tctgcgttgg ttcataactc aaactgatgg ccccaaccat attagtgcaa atttcacata   1080
tgatcataac cttttcatat gaaatcggat cgagatgaac tttatataaa cattgtagct   1140
gtcgatgata cctacaattt tatagttcac aacctttta tttcaagtca tttaaatgcc   1200
caaataggtg tttcaaatct cagatagaaa tgttcaaaag taaaaaaggt ccctatcata   1260
acataattga tatgtaagtg agttggaaaa agataagtac gtgtgagaga gatcggggat   1320
caaattctgg tgtaataatg tatgtatttc agtcataaaa attggtagca gtagttgggg   1380
ctctgtatat ataccggtaa ggatgggatg gtagtagaat aattctttt ttgtttttag   1440 tttttctgg tccaaaattt caaatttgga tcccttactt gtaccaacta atattaatga   1500
gtgttgaggg tagtagaggt gcaactttac cataatccct ctgtttcagg ttataagacg   1560
ttttgacttt aaatttgacc aagtttatgc gcaaatatag taatatttat aatactatat   1620
tagtttcatt aaataaataa ttgaatatat tttcataata aatttgtgtt gagttcaaaa   1680
tattattaat tttttctaca aacttggtca aacttgaagc agtttgactt tgaccaaagt   1740
caaaacgtct tataacttga aacggatgga ttactttttt tgtggggaca agtttacaat   1800
gtttaataaa gcacaatcca tcttaatgtt ttcaagctga atattgtaaa attcatggat   1860
aaaccagctt ctaaatgttt aaccgggaaa atgtcgaacg acaaattaat attttaagt   1920 gatgggagt attaattaag gagtgacaac tcaactttca atatcgtact aaactgtggg   1980 atttatttc taaaatttta taccctgcca attcacgtgt tgtagatctt ttttttcac   2040 taaccgacac caggtatatc aattttattg aatatagcag caaaagaat gtgttgtact   2100 tgtaaacaaa aagcaaactg tacataaaaa aaaatgcact cctatataat taagctcata   2160
aagatgcttt gcttcgtgag ggcccaagtt ttgatgacct tttgcttgat ctcgaaatta   2220
aaatttaagt actgttaagg gagttcacac caccatcaat tttcagcctg aagaaacagt   2280
taaacaacga ccccgatgac cagtctactg ctctccacat actagctgca ttattgatca   2340
caaaacaaaa caaaacgaaa taaaaatcag cagcgagagt gtgcagagag agacaaaggt   2400
gatctggcgt ggatatctcc ccatccatcc tcacccgcgc tgcccatcac tcgccgccgc   2460
atactccatc atgtggagag aggaagacga ggaccacagc cagagcccgg gtcgagatgc   2520
caccacggcc acaacccacg agcccggcgc gacaccaccg cgcgcgcgtg agccagccac   2580
aaacgcccgc ggataggcgc gcgcacgccg gccaatccta ccacatcccc ggcctccgcg   2640
gctcgcgagc gccgctgcca tccgatccgc tgagttttgg ctatttatac gtaccgcggg   2700
```

| | |
|---|---|
| agcctgtgtg cagagcagtg catctcaaga agtactcgag caaagaagga gagagcttgg | 2760 |
| tgagctgcag ccatggtaga tctgagggta aatttctagt tttttctcctt cattttcttg | 2820 |
| gttaggaccc ttttctcttt ttatttttt gagctttgat ctttctttaa actgatctat | 2880 |
| tttttaattg attggttatg gtgtaaatat tacatagctt taactgataa tctgattact | 2940 |
| ttatttcgtg tgtctatgat gatgatgata gttacagaac cgacgaacta gtgcgcaggc | 3000 |
| ggttgtgcag gcgatgcagt gccaggtggg ggtgaggggc aggacggccg tcccggcgag | 3060 |
| gcagcccgcg ggcagggtgt ggggcgtcag gagggccgcc cgcgccacct ccgggttcaa | 3120 |
| ggtgctggcg ctcggcccgg agaccaccgg ggtcatccag aggatgcagc agctgctcga | 3180 |
| catggacacc acgcccttca ccgacaagat catcgccgag tacatctggg ttggaggatc | 3240 |
| tggaattgac ctcagaagca aatcaaggac gatttcgaag ccagtggagg acccgtcaga | 3300 |
| gctgccgaaa tggaactacg acggatcgag cacggggcag gctcctgggg aagacagtga | 3360 |
| agtcatccta tacccacagg ccatattcaa ggacccattc cgaggaggca acaacatact | 3420 |
| ggttatctgt gacacctaca caccacaggg ggaacccatc cctactaaca aacgccacat | 3480 |
| ggctgcacaa atcttcagtg accccaaggt cacttcacaa gtgccatggt tcggaatcga | 3540 |
| acaggagtac actctgatgc agagggatgt gaactggcct cttggctggc ctgttggagg | 3600 |
| gtaccctggc ccccagggtc catactactg cgccgtagga tcagacaagt catttggccg | 3660 |
| tgacatatca gatgctcact acaaggcgtg cctttacgct ggaattgaaa tcagtggaac | 3720 |
| aaacggggag gtcatgcctg gtcagtggga gtaccaggtt ggacccagcg ttggtattga | 3780 |
| tgcaggagac cacatatggg cttccagata cattctcgag agaatcacgg agcaagctgg | 3840 |
| tgtggtgctc acccttgacc aaaaccaat ccagggtgac tggaacggag ctggctgcca | 3900 |
| cacaaactac agcacattga gcatgcgcga ggatggaggt ttcgacgtga tcaagaaggc | 3960 |
| aatcctgaac ctttcacttc gccatgactt gcacatagcc gcatatggtg aaggaaacga | 4020 |
| gcggaggttg acagggctac acgagacagc tagcatatca gacttctcat ggggtgtggc | 4080 |
| gaaccgtggc tgctctattc gtgtggggcg agacaccgag gcgaagggca aggatacct | 4140 |
| ggaggaccgt cgcccggcct ccaacatgga cccgtacacc gtgacggcgc tgctggccga | 4200 |
| gaccacgatc ctgtgggagc cgaccctcga ggcggaggcc ctcgctgcca agaagctggc | 4260 |
| gctgaaggta tga | 4273 |

<210> SEQ ID NO 41
<211> LENGTH: 436
<212> TYPE: PRT
<213> ORGANISM: Artificial Sequence
<220> FEATURE:
<223> OTHER INFORMATION: Translation product of SEQ ID NO: 40 DNA

<400> SEQUENCE: 41

Met Val Asp Leu Arg Asn Arg Arg Thr Ser Ala Gln Ala Val Val Gln
1               5                   10                  15

Ala Met Gln Cys Gln Val Gly Val Arg Gly Arg Thr Ala Val Pro Ala
            20                  25                  30

Arg Gln Pro Ala Gly Arg Val Trp Gly Val Arg Ala Ala Arg Ala
        35                  40                  45

Thr Ser Gly Phe Lys Val Leu Ala Leu Gly Pro Glu Thr Thr Gly Val
    50                  55                  60

Ile Gln Arg Met Gln Gln Leu Leu Asp Met Asp Thr Thr Pro Phe Thr
65                  70                  75                  80

```
Asp Lys Ile Ile Ala Glu Tyr Ile Trp Val Gly Gly Ser Gly Ile Asp
             85                  90                  95
Leu Arg Ser Lys Ser Arg Thr Ile Ser Lys Pro Val Glu Asp Pro Ser
         100                 105                 110
Glu Leu Pro Lys Trp Asn Tyr Asp Gly Ser Ser Thr Gly Gln Ala Pro
     115                 120                 125
Gly Glu Asp Ser Glu Val Ile Leu Tyr Pro Gln Ala Ile Phe Lys Asp
 130                 135                 140
Pro Phe Arg Gly Gly Asn Asn Ile Leu Val Ile Cys Asp Thr Tyr Thr
145                 150                 155                 160
Pro Gln Gly Glu Pro Ile Pro Thr Asn Lys Arg His Met Ala Ala Gln
                 165                 170                 175
Ile Phe Ser Asp Pro Lys Val Thr Ser Gln Val Pro Trp Phe Gly Ile
             180                 185                 190
Glu Gln Glu Tyr Thr Leu Met Gln Arg Asp Val Asn Trp Pro Leu Gly
         195                 200                 205
Trp Pro Val Gly Gly Tyr Pro Gly Pro Gln Gly Pro Tyr Tyr Cys Ala
     210                 215                 220
Val Gly Ser Asp Lys Ser Phe Gly Arg Asp Ile Ser Asp Ala His Tyr
225                 230                 235                 240
Lys Ala Cys Leu Tyr Ala Gly Ile Glu Ile Ser Gly Thr Asn Gly Glu
                 245                 250                 255
Val Met Pro Gly Gln Trp Glu Tyr Gln Val Gly Pro Ser Val Gly Ile
             260                 265                 270
Asp Ala Gly Asp His Ile Trp Ala Ser Arg Tyr Ile Leu Glu Arg Ile
         275                 280                 285
Thr Glu Gln Ala Gly Val Val Leu Thr Leu Asp Pro Lys Pro Ile Gln
     290                 295                 300
Gly Asp Trp Asn Gly Ala Gly Cys His Thr Asn Tyr Ser Thr Leu Ser
305                 310                 315                 320
Met Arg Glu Asp Gly Gly Phe Asp Val Ile Lys Lys Ala Ile Leu Asn
                 325                 330                 335
Leu Ser Leu Arg His Asp Leu His Ile Ala Ala Tyr Gly Glu Gly Asn
             340                 345                 350
Glu Arg Arg Leu Thr Gly Leu His Glu Thr Ala Ser Ile Ser Asp Phe
         355                 360                 365
Ser Trp Gly Val Ala Asn Arg Gly Cys Ser Ile Arg Val Gly Arg Asp
     370                 375                 380
Thr Glu Ala Lys Gly Lys Gly Tyr Leu Glu Asp Arg Arg Pro Ala Ser
385                 390                 395                 400
Asn Met Asp Pro Tyr Thr Val Thr Ala Leu Leu Ala Glu Thr Thr Ile
                 405                 410                 415
Leu Trp Glu Pro Thr Leu Glu Ala Glu Ala Leu Ala Ala Lys Lys Leu
             420                 425                 430
Ala Leu Lys Val
         435

<210> SEQ ID NO 42
<211> LENGTH: 1992
<212> TYPE: DNA
<213> ORGANISM: Zea mays

<400> SEQUENCE: 42
ctgcagtgca gcgtgacccg gtcgtgcccc tctctagaga taatgagcat tgcatgtcta    60
```

```
agttataaaa aattaccaca tattttttt gtcacacttg tttgaagtgc agtttatcta      120
tctttataca tatatttaaa ctttactcta cgaataatat aatctatagt actacaataa      180
tatcagtgtt ttagagaatc atataaatga acagttagac atggtctaaa ggacaattga      240
gtattttgac aacaggactc tacagtttta tcttttagt gtgcatgtgt tctccttttt       300
ttttgcaaat agcttcacct ataataact tcatccattt tattagtaca tccatttagg       360
gtttagggtt aatggttttt atagactaat ttttttagta catctatttt attctatttt      420
agcctctaaa ttaagaaaac taaaactcta ttttagtttt tttatttaat aatttagata      480
taaaatagaa taaaataaag tgactaaaaa ttaaacaaat acccctttaag aaattaaaaa     540
aactaaggaa acattttct tgtttcgagt agataatgcc agcctgttaa acgccgtcga       600
cgagtctaac ggacaccaac cagcgaacca gcagcgtcgc gtcgggccaa gcgaagcaga      660
cggcacggca tctctgtcgc tgcctctgga cccctctcga gagttccgct ccaccgttgg      720
acttgctccg ctgtcggcat ccagaaattg cgtggcggag cggcagacgt gagccggcac      780
ggcaggcggc ctcctcctcc tctcacggca cggcagctac gggggattcc tttcccaccg      840
ctccttcgct ttcccttcct cgcccgccgt aataaataga cacccctcc acaccctctt       900
tccccaacct cgtgttgttc ggagcgcaca cacacacaac cagatctccc ccaaatccac      960
ccgtcggcac ctccgcttca aggtacgccg ctcgtcctcc ccccccccc ctctctacct      1020
tctctagatc ggcgttccgg tccatggtta gggcccggta gttctacttc tgttcatgtt     1080
tgtgttagat ccgtgtttgt gttagatccg tgctgctagc gttcgtacac ggatgcgacc     1140
tgtacgtcag acacgttctg attgctaact tgccagtgtt tctctttggg aatcctggg      1200
atggctctag ccgttccgca gacgggatcg atttcatgat ttttttttgtt tcgttgcata    1260
gggtttggtt tgcccttttc ctttatttca atatatgccg tgcacttgtt tgtcgggtca    1320
tcttttcatg cttttttttg tcttggttgt gatgatgtgg tctggttggg cggtcgttct    1380
agatcggagt agaattctgt ttcaaactac ctggtggatt tattaatttt ggatctgtat    1440
gtgtgtgcca tacatattca tagttacgaa ttgaagatga tggatggaaa tatcgatcta    1500
ggataggtat acatgttgat gcgggtttta ctgatgcata tacagagatg cttttttgttc   1560
gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg tttactgat gcatatacat gatggcatat gcagcatcta ttcatatgct     1800
ctaaccttga gtacctatct attataataa acaagtatgt tttataatta ttttgatctt    1860
gatatacttg gatgatggca tatgcagcag ctatatgtgg attttttag ccctgccttc     1920
atacgctatt tatttgcttg gtactgtttc ttttgtcgat gctcaccctg ttgtttggtg    1980
ttacttctgc ag                                                         1992

<210> SEQ ID NO 43
<211> LENGTH: 1248
<212> TYPE: DNA
<213> ORGANISM: Hordeum vulgare

<400> SEQUENCE: 43
atggcatccg ccccgcctc cgcctccgcg gccctctcca ccgccgcccc cgccgacaac       60
ggggccgcca agcccacgga gcagcggccg gtacaggtgg ctaagcgatt ggagaagttc      120
aaaacaacaa ttttcacaca gatgagcatg ctcgcagtga agcatggagc aataaaacctt     180
```

```
ggacagggt ttcccaattt tgatggccct gactttgtca aagatgctgc tattgaggct      240
atcaaagctg aaagaatca gtatgcaaga ggatatggtg tgcctgaatt gaactcagct      300
gttgctgaga gatttctcaa ggacagtgga ttgcacatcg atcctgataa ggaagttact    360
gttacatctg ggtgcacaga agcaatagct gcaacgatat tgggtctgat caaccctggg    420
gatgaagtca tactgtttgc tccattctat gattcttatg aggctacact gtccatggct    480
ggtgcgaatg tcaaagccat tacactccgc cctccggact tgcagtccc tcttgaagag     540 ctaaaggctg cagtctcgaa gaataccaga gcaataatga ttaatacacc tcacaaccct    600
accgggaaaa tgttcacaag ggaggaactt gagttcattg ctgatctctg caaggaaaat    660
gacgtgttgc tctttgccga tgaggtctac gacaagctgg cgtttgaggc ggatcacata    720
tcaatggctt ctattcctgg catgtatgag aggaccgtca ctatgaactc ctgggggaag    780
acgttctcct tgaccggatg aagatcggc tgggcgatag caccaccgca cctgacatgg     840
ggcgtaaggc aggcacactc cttcctcaca ttcgccacct ccacgccgat gcaatcagca    900
gcggcggcgg ccctgagagc accggacagc tactttgagg agctgaagag ggactacggc    960
gcaaagaaag cgctgctggt ggacgggctc aaggcggcgg gcttcatcgt ctacccttcg   1020 agcggaaccct acttcatcat ggtcgaccac accccgttcg ggttcgacaa cgacgtcgag  1080
ttctgcgagt acttgatccg cgaggtcggc gtcgtggcca tcccgccaag cgtgttctac   1140
ctgaacccgg aggacgggaa gaacctggtg aggttcacct tctgcaagga cgacgacacg   1200
ctaagggcgg cggtggacag gatgaaggcc aagctcagga gaaaatga                1248
```

<210> SEQ ID NO 44
<211> LENGTH: 415
<212> TYPE: PRT
<213> ORGANISM: Hordeum vulgare

<400> SEQUENCE: 44

```
Met Ala Ser Ala Pro Ala Ser Ala Ala Leu Ser Thr Ala Ala
  1               5                  10                  15

Pro Ala Asp Asn Gly Ala Ala Lys Pro Thr Glu Gln Arg Pro Val Gln
             20                  25                  30

Val Ala Lys Arg Leu Glu Lys Phe Lys Thr Thr Ile Phe Thr Gln Met
         35                  40                  45

Ser Met Leu Ala Val Lys His Gly Ala Ile Asn Leu Gly Gln Gly Phe
     50                  55                  60

Pro Asn Phe Asp Gly Pro Asp Phe Val Lys Asp Ala Ala Ile Glu Ala
 65                  70                  75                  80

Ile Lys Ala Gly Lys Asn Gln Tyr Ala Arg Gly Tyr Gly Val Pro Glu
                 85                  90                  95

Leu Asn Ser Ala Val Ala Glu Arg Phe Leu Lys Asp Ser Gly Leu His
            100                 105                 110

Ile Asp Pro Asp Lys Glu Val Thr Val Thr Ser Gly Cys Thr Glu Ala
        115                 120                 125

Ile Ala Ala Thr Ile Leu Gly Leu Ile Asn Pro Gly Asp Glu Val Ile
    130                 135                 140

Leu Phe Ala Pro Phe Tyr Asp Ser Tyr Glu Ala Thr Leu Ser Met Ala
145                 150                 155                 160

Gly Ala Asn Val Lys Ala Ile Thr Leu Arg Pro Pro Asp Phe Ala Val
                165                 170                 175

Pro Leu Glu Glu Leu Lys Ala Ala Val Ser Lys Asn Thr Arg Ala Ile
```

```
                180                 185                 190
Met Ile Asn Thr Pro His Asn Pro Thr Gly Lys Met Phe Thr Arg Glu
                    195                 200                 205

Glu Leu Glu Phe Ile Ala Asp Leu Cys Lys Glu Asn Asp Val Leu Leu
            210                 215                 220

Phe Ala Asp Glu Val Tyr Asp Lys Leu Ala Phe Glu Ala Asp His Ile
225                 230                 235                 240

Ser Met Ala Ser Ile Pro Gly Met Tyr Glu Arg Thr Val Thr Met Asn
                245                 250                 255

Ser Leu Gly Lys Thr Phe Ser Leu Thr Gly Trp Lys Ile Gly Trp Ala
            260                 265                 270

Ile Ala Pro Pro His Leu Thr Trp Gly Val Arg Gln Ala His Ser Phe
            275                 280                 285

Leu Thr Phe Ala Thr Ser Thr Pro Met Gln Ser Ala Ala Ala Ala Ala
            290                 295                 300

Leu Arg Ala Pro Asp Ser Tyr Phe Glu Glu Leu Lys Arg Asp Tyr Gly
305                 310                 315                 320

Ala Lys Lys Ala Leu Leu Val Asp Gly Leu Lys Ala Ala Gly Phe Ile
                325                 330                 335

Val Tyr Pro Ser Ser Gly Thr Tyr Phe Ile Met Val Asp His Thr Pro
                340                 345                 350

Phe Gly Phe Asp Asn Asp Val Glu Phe Cys Glu Tyr Leu Ile Arg Glu
            355                 360                 365

Val Gly Val Val Ala Ile Pro Pro Ser Val Phe Tyr Leu Asn Pro Glu
        370                 375                 380

Asp Gly Lys Asn Leu Val Arg Phe Thr Phe Cys Lys Asp Asp Asp Thr
385                 390                 395                 400

Leu Arg Ala Ala Val Asp Arg Met Lys Ala Lys Leu Arg Lys Lys
                405                 410                 415

<210> SEQ ID NO 45
<211> LENGTH: 2735
<212> TYPE: DNA
<213> ORGANISM: Artificial Sequence
<220> FEATURE:
<223> OTHER INFORMATION: Synthetic expression cassette

<400> SEQUENCE: 45
gtttgaatcc tccttaaagt ttttctctgg agaaactgta gtaattttac tttgttgtgt      60
tcccttcatc ttttgaatta atggcatttg tttaatact aatctgcttc tgaaacttgt     120
aatgtatgta tatcagtttc ttataattta tccaagtaat atcttccatt ctctatgcaa    180
ttgcctgcat aagctcgaca aaagagtaca tcaaccccctc ctcctctgga ctactctagc   240
taaacttgaa tttccccctta agattatgaa attgatatat ccttaacaaa cgactccttc   300
tgttggaaaa tgtagtactt gtctttcttc ttttgggtat atagtttta tacaccat      360 actatgtaca acatccaagt agagtgaaat ggatacatgt acaagactta tttgattgat   420
tgatgacttg agttgcctta ggagtaacaa attcttaggt caataaatcg ttgatttgaa   480
attaatctct ctgtcttaga cagataggaa ttatgacttc caatggtcca gaaagcaaag   540
ttcgcactga gggtatactt ggaattgaga cttgcacagg tccagaaacc aaagttccca   600
tcgagctcta aaatcacatc tttggaatga aattcaatta gagataagtt gcttcatagc   660
ataggtaaaa tggaagatgt gaagtaacct gcaataatca gtgaaatgac attaatacac   720
taaatacttc atatgtaatt atcctttcca ggttaacaat actctataaa gtaagaatta   780
```

```
tcagaaatgg gctcatcaaa cttttgtact atgtatttca tataaggaag tataactata    840
cataagtgta tacacaactt tattcctatt ttgtaaaggt ggagagactg ttttcgatgg    900
atctaaagca atatgtctat aaaatgcatt gatataataa ttatctgaga aaatccagaa    960
ttggcgttgg attatttcag ccaaatagaa gtttgtacca tacttgttga ttccttctaa   1020
gttaaggtga agtatcattc ataaacagtt ttccccaaag tactactcac caagtttccc   1080
tttgtagaat taacagttca aatatatggc gcagaaatta ctctatgccc aaaaccaaac   1140
gagaaagaaa caaaatacag gggttgcaga ctttatttc gtgttagggt gtgtttttc    1200 atgtaattaa tcaaaaaata ttatgacaaa aacatttata catattttta ctcaacactc   1260
tgggtatcag ggtgggttgt gttcgacaat caatatggaa aggaagtatt ttccttattt   1320
ttttagttaa tattttcagt tataccaaac atacctttgtg atattattt taaaaatgaa    1380 aaactcgtca gaaagaaaaa gcaaaagcaa caaaaaaatt gcaagtattt tttaaaaaag    1440
aaaaaaaaaa catatcttgt ttgtcagtat gggaagtttg agataaggac gagtgagggg    1500
ttaaaattca gtggccattg atttgtaat gccaagaacc acaaaatcca atggttacca    1560
ttcctgtaag atgaggtttg ctaactcttt ttgtccgtta gataggaagc cttatcacta   1620
tatatacaag gcgtcctaat aacctcttag taaccaatta tttcagcacc atgtctctgc   1680
tctcagatct cgttaacctc aacctcaccg atgccaccgg gaaaatcatc gccgaataca   1740
tatggatcgg tggatctgga atggatatca gaagcaaagc caggacacta ccaggaccag   1800
tgactgatcc atcaaagctt cccaagtgga actacgacgg atccagcacc ggtcaggctg   1860
ctggagaaga cagtgaagtc attctatacc ctcaggcaat attcaaggat cccttcagga   1920
aaggcaacaa catcctggtg atgtgtgatg cttacacacc agctggtgat cctattccaa   1980
ccaacaagag gcacaacgct gctaagatct tcagccaccc cgacgttgcc aaggaggagc   2040
cttggtatgg gattgagcaa gaatacactt tgatgcaaaa ggatgtgaac tggccaattg   2100
gttggcctgt tggtggctac cctggccctc agggaccttac ctactgtggt gtgggagctg   2160
acaaagccat tggtcgtgac attgtggatg ctcactacaa ggcctgtctt tacgccggta   2220
ttggtatttc tggtatcaat ggagaagtca tgccaggcca gtgggagttc caagtcggcc   2280
ctgttgaggg tattagttct ggtgatcaag tctgggttgc tcgatacctt ctcgagagga   2340
tcactgagat ctctggtgta attgtcagct tcgacccgaa accagtcccg ggtgactgga   2400
atggagctgg agctcactgc aactacagca ctaagacaat gagaaacgat ggaggattag   2460
aagtgatcaa gaaagcgata gggaagcttc agctgaaaca caagaacac attgctgctt   2520 acggtgaagg aaacgagcgt cgtctcactg gaaagcacga accgcagac atcaacacat   2580 tctcttgggg agtcgcgaac cgtggagcgt cagtgagagt gggacgtgac acagagaagg   2640
aaggtaaagg gtacttcgaa gacagaaggc cagcttctaa catggatcct tacgttgtca   2700
cctccatgat cgctgagacg accatactcg gttga                             2735
```

<210> SEQ ID NO 46
<211> LENGTH: 3271
<212> TYPE: DNA
<213> ORGANISM: Artificial Sequence
<220> FEATURE:
<223> OTHER INFORMATION: Synthetic expression cassette

<400> SEQUENCE: 46

```
ggtaccgttt gaatcctcct taaagttttt ctctggagaa actgtagtaa ttttactttg     60
```

-continued

```
ttgtgttccc ttcatctttt gaattaatgg catttgtttt aatactaatc tgcttctgaa    120
acttgtaatg tatgtatatc agtttcttat aatttatcca agtaatatct tccattctct    180
atgcaattgc ctgcataagc tcgacaaaag agtacatcaa cccctcctcc tctggactac    240
tctagctaaa cttgaatttc cccttaagat tatgaaattg atatatcctt aacaaacgac    300
tccttctgtt ggaaaatgta gtacttgtct ttcttctttt gggtatatat agtttatata    360
caccatacta tgtacaacat ccaagtagag tgaaatggat acatgtacaa gacttatttg    420
attgattgat gacttgagtt gccttaggag taacaaattc ttaggtcaat aaatcgttga    480
tttgaaatta atctctctgt cttagacaga taggaattat gacttccaat ggtccagaaa    540
gcaaagttcg cactgagggt atacttggaa ttgagacttg cacaggtcca gaaccaaag    600 ttcccatcga gctctaaaat cacatctttg gaatgaaatt caattagaga taagttgctt    660
catagcatag gtaaaatgga agatgtgaag taacctgcaa taatcagtga aatgacatta    720
atacactaaa tacttcatat gtaattatcc tttccaggtt aacaatactc tataaagtaa    780
gaattatcag aaatgggctc atcaaacttt tgtactatgt atttcatata aggaagtata    840
actatacata agtgtataca caactttatt cctattttgt aaaggtggag agactgtttt    900
cgatggatct aaagcaatat gtctataaaa tgcattgata taataattat ctgagaaaat    960
ccagaattgg cgttggatta tttcagccaa atagaagttt gtaccatact tgttgattcc    1020
ttctaagtta aggtgaagta tcattcataa acagttttcc ccaaagtact actcaccaag    1080
tttccctttg tagaattaac agttcaaata tatggcgcag aaattactct atgcccaaaa    1140
ccaaacgaga aagaaacaaa atacaggggt tgcagacttt attttcgtgt tagggtgtgt    1200
tttttcatgt aattaatcaa aaaatattat gacaaaaaca tttatacata ttttttactca   1260 acactctggg tatcagggtg ggttgtgttc gacaatcaat atggaaagga agtattttcc    1320 ttatttttt agttaatatt ttcagttata ccaaacatac cttgtgatat tattttaaa     1380 aatgaaaaac tcgtcagaaa gaaaaagcaa agcaacaaa aaaattgcaa gtattttta     1440 aaaaagaaaa aaaaaaacat atcttgtttg tcagtatggg aagtttgaga taaggacgag    1500
tgaggggtta aaattcagtg gccattgatt ttgtaatgcc aagaaccaca aaatccaatg    1560
gttaccattc ctgtaagatg aggtttgcta actcttttg tccgttagat aggaagcctt     1620
atcactatat atacaaggcg tcctaataac ctcttagtaa ccaattattt cagcaccatg    1680
gtagatctga gggtaaattt ctagtttttc tccttcattt tcttggttag gacccttttc    1740 tcttttatt tttttgagct tgatctttc tttaaactga tctattttt aattgattgg       1800 ttatggtgta aatattacat agctttaact gataatctga ttactttatt tcgtgtgtct    1860
atgatgatga tgatagttac agaaccgacg aactagtatg aatctggccg ccttttcctc    1920 caccccttgcc acgctcccct ggtatgagat gccatcaata aattcctccg caactttctc    1980
gtcctcactg ctccgccgct cgctctgcgc gtcgctccgg acgatctccc acatggcctc    2040
cgccgccgcc cccacctccg cgcccgtcgc caccaccgag aacggcgccg cgaaggcgat    2100
agagcagcgg cccgtgcagg tcgcagagcg gctggaaaag ttcaagacaa caattttcac    2160
tcagatgagc atgcttgcca tcaagcatgg agcaataaac cttggccagg gctttccgaa    2220
ttttgatggc ccagactttg tgaaagaggc cgcaattcaa gctatcaatg ctgggaagaa    2280
tcagtacgca agagggtttg gtgtgcctga actgaactcg gctatcgctg aaaggttcct    2340
gaaggacagt ggattgcaag ttgacccctga caaggaagtc actgttacat ctggatgcac    2400
tgaggcaata gctgcaacca tactaggtct gatcaatcct ggcgacgagg tgatactgtt    2460
```

```
cgccccattc tacgattcat acgaggctac actgtcgatg gccggtgcca acgtgaaggc    2520
cattaccctc cgcgctccag atttcgcggt cccgcttgag gagctggagg ctgcagtctc    2580
caaggacacg aaagcgataa tgataaacac gccgcacaac ccaaccggga aaatgttcac    2640
cagggaggag ctcgaatcca tcgccgccct ctgcaaggaa aacgacgttt tgctgttctc    2700
agatgaggtc tatgacaagc tggtgtttga ggctgaccac atatccatgg cttctatccc    2760
gggcatgtac gagaggacgg tgaccatgaa ctctctgggg aagacgttct ctcttacagg    2820
atggaagatc gggtgggcaa tcgcgccgcc gcacctgaca tggggcctca ggcaggcgca    2880
ctcgttcctg acgttcgcca cctgcacacc gatgcaggcg gcggccgcgg cggctctgag    2940
ggcaccggac agctactacg acgagctgaa gagggactac agcgcgaaga aggctatcct    3000
gctggaagga ctcgaagccg cagggttcat cgtctaccca tcgagtggga catactacat    3060
catggtcgac cacaccccgt tcggtttcga cagcgacgta gagttctgcg agtacttgat    3120
ccgcgaagtc ggcgtctgcg ctataccgcc cagcgtgttc tacctcgacc ccgaagaggg    3180
aaagaaattg gtgaggttca ccttcagcaa ggacgaaggc acgctgcggg ccgcggtcga    3240
gaggttgaag gcgaagctca ggaggaaatg a                                   3271
```

<210> SEQ ID NO 47
<211> LENGTH: 467
<212> TYPE: PRT
<213> ORGANISM: Zea mays

<400> SEQUENCE: 47

```
Met Val Asp Leu Arg Asn Arg Arg Thr Ser Met Asn Leu Ala Ala Phe
 1               5                  10                  15

Ser Ser Thr Leu Ala Thr Leu Pro Trp Tyr Glu Met Pro Ser Ile Asn
             20                  25                  30

Ser Ser Ala Thr Phe Ser Ser Leu Leu Arg Arg Ser Leu Cys Ala
         35                  40                  45

Ser Leu Arg Thr Ile Ser His Met Ala Ser Ala Ala Pro Thr Ser
     50                  55                  60

Ala Pro Val Ala Thr Thr Glu Asn Gly Ala Ala Lys Ala Ile Glu Gln
65                  70                  75                  80

Arg Pro Val Gln Val Ala Glu Arg Leu Glu Lys Phe Lys Thr Thr Ile
                 85                  90                  95

Phe Thr Gln Met Ser Met Leu Ala Ile Lys His Gly Ala Ile Asn Leu
            100                 105                 110

Gly Gln Gly Phe Pro Asn Phe Asp Gly Pro Asp Phe Val Lys Glu Ala
        115                 120                 125

Ala Ile Gln Ala Ile Asn Ala Gly Lys Asn Gln Tyr Ala Arg Gly Phe
    130                 135                 140

Gly Val Pro Glu Leu Asn Ser Ala Ile Ala Glu Arg Phe Leu Lys Asp
145                 150                 155                 160

Ser Gly Leu Gln Val Asp Pro Asp Lys Glu Val Thr Val Thr Ser Gly
                165                 170                 175

Cys Thr Glu Ala Ile Ala Ala Thr Ile Leu Gly Leu Ile Asn Pro Gly
            180                 185                 190

Asp Glu Val Ile Leu Phe Ala Pro Phe Tyr Asp Ser Tyr Glu Ala Thr
        195                 200                 205

Leu Ser Met Ala Gly Ala Asn Val Lys Ala Ile Thr Leu Arg Ala Pro
    210                 215                 220
```

Asp Phe Ala Val Pro Leu Glu Glu Leu Glu Ala Ala Val Ser Lys Asp
225                 230                 235                 240

Thr Lys Ala Ile Met Ile Asn Thr Pro His Asn Pro Thr Gly Lys Met
            245                 250                 255

Phe Thr Arg Glu Glu Leu Glu Ser Ile Ala Ala Leu Cys Lys Glu Asn
        260                 265                 270

Asp Val Leu Leu Phe Ser Asp Glu Val Tyr Asp Lys Leu Val Phe Glu
    275                 280                 285

Ala Asp His Ile Ser Met Ala Ser Ile Pro Gly Met Tyr Glu Arg Thr
290                 295                 300

Val Thr Met Asn Ser Leu Gly Lys Thr Phe Ser Leu Thr Gly Trp Lys
305                 310                 315                 320

Ile Gly Trp Ala Ile Ala Pro Pro His Leu Thr Trp Gly Leu Arg Gln
                325                 330                 335

Ala His Ser Phe Leu Thr Phe Ala Thr Cys Thr Pro Met Gln Ala Ala
            340                 345                 350

Ala Ala Ala Ala Leu Arg Ala Pro Asp Ser Tyr Tyr Asp Glu Leu Lys
        355                 360                 365

Arg Asp Tyr Ser Ala Lys Lys Ala Ile Leu Leu Glu Gly Leu Glu Ala
370                 375                 380

Ala Gly Phe Ile Val Tyr Pro Ser Ser Gly Thr Tyr Tyr Ile Met Val
385                 390                 395                 400

Asp His Thr Pro Phe Gly Phe Asp Ser Asp Val Glu Phe Cys Glu Tyr
                405                 410                 415

Leu Ile Arg Glu Val Gly Val Cys Ala Ile Pro Pro Ser Val Phe Tyr
            420                 425                 430

Leu Asp Pro Glu Glu Gly Lys Lys Leu Val Arg Phe Thr Phe Ser Lys
        435                 440                 445

Asp Glu Gly Thr Leu Arg Ala Ala Val Glu Arg Leu Lys Ala Lys Leu
    450                 455                 460

Arg Arg Lys
465

<210> SEQ ID NO 48
<211> LENGTH: 392
<212> TYPE: PRT
<213> ORGANISM: Chlorella vulgaris

<400> SEQUENCE: 48

Met Ala Ala Ala Ala Gly Gly Asp Gly Pro Ser Ala Ala Arg Arg
1               5                   10                  15

Phe Asn Ser Thr Phe Ser Ser Leu Pro Thr Thr Ile Phe Glu Gln Met
            20                  25                  30

Ser Leu Leu Ala Ala Lys His Gln Ser Thr Asn Leu Gly Gln Gly Phe
        35                  40                  45

Pro Asp Asn Glu Leu Glu Gly Pro Glu Ser Met Lys Lys Val Met Ile
    50                  55                  60

Ser Leu Tyr Glu His Ser Asn Gln Tyr Pro Pro Leu Met Gly Leu Pro
65                  70                  75                  80

Glu Leu Arg Gln Ala Val Ala Ala His Ser Ala Arg His Ala Gly Ile
                85                  90                  95

Pro Val Asp Trp Gln Ala Glu Thr Leu Val Thr Val Gly Ala Thr Glu
            100                 105                 110

Ala Leu Ala Ala Ala Phe Leu Gly Leu Leu Asp Ala Gly Asp Glu Val
        115                 120                 125

-continued

```
Ile Phe Phe Glu Pro Leu Tyr Asp Ser Tyr Val Pro Met Ala Arg Arg
            130                 135                 140
Ala Gly Ala Ile Pro Arg Ile Val Gln Leu Tyr Pro Pro Ala Trp Ser
145             150                 155                 160
Ile Asp Ala Ala Glu Leu Glu Ala Ala Phe Ser Pro Gln Thr Lys Leu
                165                 170                 175
Leu Val Leu Asn Thr Pro His Asn Pro Thr Gly Lys Val Phe Gly Ala
            180                 185                 190
Glu Glu Leu Gln Leu Ile Ala Asp Leu Cys Gln Lys His Asp Cys Leu
            195                 200                 205
Cys Leu Leu Asp Glu Val Tyr Glu His Leu Val Phe Pro Gly Thr Arg
            210                 215                 220
His Thr Ser Leu Gln Ser Leu Pro Gly Met Arg Glu Arg Cys Leu Arg
225             230                 235                 240
Val Gly Trp Leu Ser Gly Pro His Asp Leu Leu Ala Ala Val Thr Lys
                245                 250                 255
Ala His Gln Phe Leu Ile Phe Thr Val Pro Ser Ala Leu Gln Arg Ala
                260                 265                 270
Val Ala Tyr Gly Leu Glu Gln Glu Glu Ala Phe Cys Cys Gly Leu Gly
            275                 280                 285
Ala Ala Leu Ser Lys Lys Arg Gln Leu Leu Glu Gly Gln Leu Ala Glu
            290                 295                 300
Ile Gly Phe Ala Val Leu Pro Ala Gln Gly Thr Tyr Phe Leu Val Ala
305                 310                 315                 320
Asp Phe Ala Gly Leu Leu Pro Ala Gly Ser Ser Glu Asp Asp Val Gln
                325                 330                 335
Phe Cys His Arg Leu Thr Val Glu Ala Gly Val Thr Leu Ile Pro Val
            340                 345                 350
Ser Ala Phe Tyr Ala Asp Arg Ala Ala Thr Pro Arg Thr Leu Val Arg
            355                 360                 365
Phe Val Phe Cys Lys Thr Asp Glu Lys Leu Asn Thr Ala Cys Gly Lys
    370                 375                 380
Leu Arg Thr Tyr Phe Gly Arg Gln
385                 390
```